United States Patent
Kim et al.

(10) Patent No.: US 10,406,216 B2
(45) Date of Patent: *Sep. 10, 2019

(54) IN SITU ANTIGEN-GENERATING CANCER VACCINE

(71) Applicant: President and Fellows of Harvard College, Cambridge, MA (US)

(72) Inventors: Jaeyun Kim, Gyeonggi-do (KR); David J. Mooney, Sudbury, MA (US); Weiwei Aileen Li, Norcross, GA (US); Praveen Arany, Cambridge, MA (US); Or Gadish, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,131

(22) Filed: Nov. 7, 2016

(65) Prior Publication Data

US 2017/0182138 A1     Jun. 29, 2017

Related U.S. Application Data

(63) Continuation of application No. 14/123,615, filed as application No. PCT/US2012/040687 on Jun. 4, 2012, now Pat. No. 9,486,512.

(60) Provisional application No. 61/493,398, filed on Jun. 3, 2011.

(51) Int. Cl.
| | | |
|---|---|---|
| *A61K 39/00* | (2006.01) | |
| *A61K 41/00* | (2006.01) | |
| *B82Y 5/00* | (2011.01) | |
| *A61K 38/19* | (2006.01) | |
| *A61K 45/06* | (2006.01) | |

(52) U.S. Cl.
CPC ........ *A61K 39/0011* (2013.01); *A61K 38/193* (2013.01); *A61K 41/0052* (2013.01); *A61K 45/06* (2013.01); *B82Y 5/00* (2013.01); *A61K 2039/5152* (2013.01); *A61K 2039/5154* (2013.01); *A61K 2039/54* (2013.01); *A61K 2039/545* (2013.01); *A61K 2039/55505* (2013.01); *A61K 2039/55511* (2013.01); *A61K 2039/55561* (2013.01); *A61K 2039/57* (2013.01); *A61K 2039/572* (2013.01); *A61K 2039/70* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,403,374 B1 | 6/2002 | Tsien et al. |
| 6,429,199 B1 | 8/2002 | Krieg et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 7,015,205 B1 | 3/2006 | Wallack et al. |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,427,602 B1 | 9/2008 | Shea et al. |
| 7,575,759 B2 | 8/2009 | Murphy et al. |
| 7,687,241 B2 | 3/2010 | Chen |
| 7,790,699 B2 | 9/2010 | Melvik et al. |
| 8,067,237 B2 | 11/2011 | Mooney et al. |
| 8,188,058 B2 | 5/2012 | Hackam et al. |
| 8,273,373 B2 | 9/2012 | Alsberg et al. |
| 8,709,464 B2 | 4/2014 | Ma et al. |
| 8,728,456 B2 | 5/2014 | Sands et al. |
| 8,932,583 B2 | 1/2015 | Mooney et al. |
| 9,012,399 B2 | 4/2015 | Cao et al. |
| 9,132,210 B2 | 9/2015 | Mooney et al. |

(Continued)

FOREIGN PATENT DOCUMENTS

| | | |
|---|---|---|
| CN | 101655611 A | 2/2010 |
| EP | 0562862 A1 | 9/1993 |

(Continued)

OTHER PUBLICATIONS

"Antigens and Receptors." Immunology. Doan et al., eds. Philadelphia: Wolters Kluwer/Lippincott Williams & Wilsons. (2008):11-23.

(Continued)

*Primary Examiner* — Sean E Aeder
(74) *Attorney, Agent, or Firm* — McCarter & English, LLP; Maria Laccotripe Zacharakis; Maneesh Gulati

(57) ABSTRACT

The invention provides compositions and methods for utilizing scaffolds in cancer vaccines.

38 Claims, 21 Drawing Sheets

(56) References Cited

U.S. PATENT DOCUMENTS

| | | |
|---|---|---|
| 9,370,558 B2 | 6/2016 | Ali et al. |
| 9,381,235 B2 | 7/2016 | Sands et al. |
| 9,446,107 B2 | 9/2016 | Mooney et al. |
| 9,486,512 B2 | 11/2016 | Kim et al. |
| 2002/0131853 A1 | 9/2002 | Nagasawa |
| 2002/0131953 A1 | 9/2002 | Takashima et al. |
| 2002/0150604 A1 | 10/2002 | Yi et al. |
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0194397 A1 | 10/2003 | Mishra |
| 2003/0232895 A1 | 12/2003 | Omidian et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0220111 A1 | 11/2004 | Kleinman et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0037330 A1 | 2/2005 | Fischer et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2005/0202394 A1 | 9/2005 | Dobson |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2006/0292134 A1 | 12/2006 | Stohs |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0138416 A1 | 6/2008 | Rauh et al. |
| 2008/0152624 A1 | 6/2008 | Paludan et al. |
| 2008/0206308 A1 | 8/2008 | Jabbari et al. |
| 2008/0268052 A1 | 10/2008 | Voytik-Harbin et al. |
| 2009/0017096 A1 | 1/2009 | Lowman et al. |
| 2009/0192079 A1 | 7/2009 | Santos et al. |
| 2009/0238853 A1 | 9/2009 | Liu et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0020216 A1 | 1/2011 | Mooney et al. |
| 2011/0117170 A1 | 5/2011 | Cao et al. |
| 2011/0223255 A1 | 9/2011 | Thiesen et al. |
| 2011/0300186 A1 | 12/2011 | Hellstrom et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0329791 A1 | 12/2012 | Ashwell et al. |
| 2013/0029030 A1 | 1/2013 | Larsen |
| 2013/0177536 A1 | 7/2013 | Mooney et al. |
| 2013/0202707 A1 | 8/2013 | Ali et al. |
| 2013/0302396 A1 | 11/2013 | Mooney et al. |
| 2013/0331343 A1 | 12/2013 | Cao et al. |
| 2014/0079752 A1 | 3/2014 | Huebsch et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0227327 A1 | 8/2014 | Bencherif et al. |
| 2014/0234423 A1 | 8/2014 | Sands et al. |
| 2015/0024026 A1 | 1/2015 | Mooney et al. |
| 2015/0072009 A1 | 3/2015 | Kim et al. |
| 2015/0366956 A1 | 12/2015 | Mooney et al. |
| 2016/0220667 A1 | 8/2016 | Mooney et al. |
| 2016/0220668 A1 | 8/2016 | Mooney et al. |
| 2016/0228543 A1 | 8/2016 | Mooney et al. |
| 2016/0271298 A1 | 9/2016 | Mooney et al. |
| 2016/0279219 A1 | 9/2016 | Mooney et al. |
| 2016/0279220 A1 | 9/2016 | Mooney et al. |
| 2016/0296611 A1 | 10/2016 | Ali et al. |
| 2017/0042995 A1 | 2/2017 | Ali et al. |

FOREIGN PATENT DOCUMENTS

| | | |
|---|---|---|
| EP | 1452191 A2 | 9/2004 |
| EP | 1561481 A2 | 8/2005 |
| EP | 1712238 A1 | 10/2006 |
| JP | 2000503884 A | 4/2000 |
| JP | 2003506401 A | 2/2003 |
| JP | 2003180815 A | 7/2003 |
| JP | 2004520043 A | 7/2004 |
| JP | 2005160669 A | 6/2005 |
| JP | 2005170816 A | 6/2005 |
| JP | 2005528401 A | 9/2005 |
| JP | 2007500673 A | 1/2007 |
| JP | 2007503881 A | 3/2007 |
| JP | 2007528848 A | 10/2007 |
| JP | 2008515503 A | 5/2008 |
| JP | 2008528114 A | 7/2008 |
| JP | 2009519042 A | 5/2009 |
| JP | 2009521406 A | 6/2009 |
| JP | 2009540921 A | 11/2009 |
| JP | 2010502824 A | 1/2010 |
| JP | 2010508976 A | 3/2010 |
| JP | 2010227012 A | 10/2010 |
| JP | 2011511684 A | 4/2011 |
| JP | 2011511834 A | 4/2011 |
| WO | WO-9616086 A1 | 5/1996 |
| WO | WO-98012228 A1 | 3/1998 |
| WO | WO-9816266 A1 | 4/1998 |
| WO | WO-9951259 A2 | 10/1999 |
| WO | WO-0050006 A2 | 8/2000 |
| WO | WO-01010421 A1 | 2/2001 |
| WO | WO-0135932 A2 | 5/2001 |
| WO | WO-0216557 A2 | 2/2002 |
| WO | WO-0240071 A1 | 5/2002 |
| WO | WO-02058723 A2 | 8/2002 |
| WO | WO-03020884 A2 | 3/2003 |
| WO | WO-04006990 A2 | 1/2004 |
| WO | WO-04030706 A2 | 4/2004 |
| WO | WO-2004029230 A2 | 4/2004 |
| WO | WO-2004031371 A2 | 4/2004 |
| WO | WO-04089413 A1 | 10/2004 |
| WO | WO-05013896 A2 | 2/2005 |
| WO | WO-05013933 A1 | 2/2005 |
| WO | WO-05026318 A2 | 3/2005 |
| WO | WO-05037190 A2 | 4/2005 |
| WO | WO-05037293 A1 | 4/2005 |
| WO | WO-05046748 A1 | 5/2005 |
| WO | WO-05072088 A2 | 8/2005 |
| WO | WO-2006040128 A1 | 4/2006 |
| WO | WO-2006078987 A2 | 7/2006 |
| WO | WO-06119619 A1 | 11/2006 |
| WO | WO-06136905 A2 | 12/2006 |
| WO | WO-07030901 A1 | 3/2007 |
| WO | WO-07063075 A1 | 6/2007 |
| WO | WO-07064152 A1 | 6/2007 |
| WO | WO-07070660 A2 | 6/2007 |
| WO | WO-07078196 A1 | 7/2007 |
| WO | WO-07107739 A1 | 9/2007 |
| WO | WO-07150020 A1 | 12/2007 |
| WO | WO-08018707 A1 | 2/2008 |

(56) References Cited

FOREIGN PATENT DOCUMENTS

| WO | WO-2008031525 A1 | 3/2008 |
|---|---|---|
| WO | WO-08109852 A2 | 9/2008 |
| WO | WO-08114149 A2 | 9/2008 |
| WO | WO-08148761 A1 | 12/2008 |
| WO | WO-08157394 A2 | 12/2008 |
| WO | WO-09002401 A2 | 12/2008 |
| WO | WO-09005769 A2 | 1/2009 |
| WO | WO-09018500 A1 | 2/2009 |
| WO | WO-09072767 A2 | 6/2009 |
| WO | WO-09074341 A1 | 6/2009 |
| WO | WO-09102465 A2 | 8/2009 |
| WO | WO-09146456 A1 | 12/2009 |
| WO | WO-09155583 A1 | 12/2009 |
| WO | WO-2010/78209 A2 | 7/2010 |
| WO | WO-10120749 A2 | 10/2010 |
| WO | WO-11014871 A1 | 2/2011 |
| WO | WO-11063336 A2 | 5/2011 |
| WO | WO-2011109834 A2 | 9/2011 |
| WO | WO-11130753 A2 | 10/2011 |
| WO | WO-11150240 A1 | 12/2011 |
| WO | WO-11151431 A1 | 12/2011 |
| WO | WO-11163669 A2 | 12/2011 |
| WO | WO-12009611 A2 | 1/2012 |
| WO | WO-12019049 A1 | 2/2012 |
| WO | WO-12048165 A2 | 4/2012 |
| WO | WO-12064697 A2 | 5/2012 |
| WO | WO-12148684 A1 | 11/2012 |
| WO | WO-2012149358 A1 | 11/2012 |
| WO | WO-12167230 A1 | 12/2012 |
| WO | WO-13106852 A1 | 7/2013 |
| WO | WO-13158673 A1 | 10/2013 |
| WO | WO-2015168379 A2 | 11/2015 |
| WO | WO-2016123573 A1 | 8/2016 |
| WO | WO-16161372 A1 | 10/2016 |

OTHER PUBLICATIONS

"Collagen: The Fibrous Proteins of the Matrix." Molecular Cell Biology. Lodish et al., eds. New York: W.H. Freeman. Section 22.3(2000):979-985.
"Transient." Merriam-Webster Dictionary. Web. Jul. 18, 2014. www.merriam-webster.com/dictionary/transient.
"Wound Management: Past, Present, and Future." Clinicians' Pocket Guide to Chronic Wound Repair. Mulder et al., eds. Springhouse, PA: Springhouse Corporation. (1998):85-90.
Abrahams et al. "Expression and Secretion of Antiviral Factors by Trophoblast Cells Following Stimulation by the TLF-3 Agonist, Poly (I:C)." Hum. Reprod. 21.9(2006):2432-2439.
Agache et al."Mechanical Properties and Young's Modulus of Human Skin in Vivo." Arch. Dermatol. Res. 269.3(1980):221-232.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." J. Immunol. 171.10(2003):4984-4989.
Aguado et al. "Improving Viability of Stem Cells During Syringe Needle Flow Through the Design of Hydrogel Cell Carriers." Tissue Eng. Part A. 18.7-8(2012):806-815.
Akira et al. "Pathogen Recognition and Innate Immunity." Cell. 124.4(2006):783-801.
Akira et al. "Toll-Like Receptors: Critical Proteins Linking Innate and Acquired Immunity." Nat. Immunol. 2.8(2001):675-680.
Akpalo et al. "Fibrin-Polyethylene Oxide Interpenetrating Polymer Networks: New Self-Supported Biomaterials Combining the Properties of Both Protein Gel and Synthetic Polymer." Acta Biomater. 7.6(2011):2418-2427.
Aldhous. "Print Me a Heart and a Set of Arteries." New Scientist. 2547(2006):19.
Ali et al. "Controlled Local Delivery of GM-CSF From Polymer-Based Vaccines Enhances Anti-Tumor Immune Responses by Priming Host Dendritic Cells." 2007 AACR Annual Meeting. 48(2007):652. (Abstract #2736).
Ali et al. "Converging Cell Therapy with Biomaterials." Cell Transplantation from Laboratory to Clinic. Burlington, MA: Elsevier, Inc. (2006):591-609.
Ali et al. "In situ Regulation of DC Subsets and T Cells Mediates Tumor Regression in Mice." Sci. Transl. Med. 1.8(2009):8-19.
Ali et al. "Infection-Mimicking Materials to Program Dendritic Cells in situ." Nat. Mater. 8.2(2009):151-158.
Ali et al. "Sustained GM-CSF and PEI Condensed pDNA Presentation Increases the Level and Duration of Gene Expression in Dendritic Cells." J. Control. Release. 132.3(2008):273-278.
Allen et al. "Regulation of Satellite Cells During Skeletal Muscle Growth and Development." Proc. Soc. Exp. Biol. Med. 194.2(1990):81-86.
Allen et al. "Regulation of Skeletal Muscle Satellite Cell Proliferation by Bovine Pituitary Fibroblast Growth Factor." Exp. Cell Res. 152.1(1984):154-160.
Almarza et al. "Evaluation of Three Growth Factors in Combination of Two for Temporomandibular Joint Disc Tissue Engineering." Arch. Oral Biol. 51.3(2006):215-221.
Alsberg et al. "Cell-Interactive Alginate Hydrogels for Bone Tissue Engineering." J. Dent. Res. 80.11(2001):2025-2029.
Alsberg et al. "Engineering Growing Tissues." PNAS. 99.18(2002):12025-12030.
Alsberg et al. "Regulating Bone Formation via Controlled Scaffold Design." J. Dent. Res. 82.11(2003):903-908.
American Diabetes Association. "Standards of Medical Care in Diabetes—2013." Diabetes Care. 36.S1(2013):S11-S66.
Anderson et al. "Biomaterial Microarrays: Rapid, Microscale Screening of Polymer-Cell Interaction." Biomaterials. 26.23(2005):4892-4897.
Anderson et al. "Nanoliter-Scale Synthesis of Arrayed Biomaterials and Application to Human Embryonic Stem Cells." Nat. Biotechnol. 22.7(2004):863-866.
Anderson et al. "The NOD Mouse: A Model of Immune Dysregulation." Annu. Rev. Immunol. 23(2005):447-485.
Anderson. "A Role for Nitric Oxide in Muscle Repair: Nitric Oxide-Mediated Activation of Muscle Satellite Cells." Mol. Biol. Cell. 11(2000):1859-1874.
Annaidh et al. "Characterization of the Anistropic Mechanical Properties of Excised Human Skin." J. Mech. Behav. Biomed. Mater. 5.1(2012):139-148.
Annual Review Meneki (Immunity). 2007;2008:122-31.
Arany et al. "At the Edge of Translation—Materials to Program Cells for Directed Differentiation." Oral Dis. 17.3(2011):241-251.
Aschner et al. "Metabolic Memory for Vascular Disease in Diabetes." Diabetes Technol. Ther. 14.S1(2012):S68-S74.
Atala et al. "Endoscopic Treatment of Vesicoureteral Reflux with a Chondrocyte-Alginate Suspension." J. Urol. 152(1994):641-643.
Aubin et al. "Directed 3D Cell Alignment and Elongation in Microengineered Hydrogels." Biomater. 31.27(2010):6941-6951.
Augst et al. "Alginate Hydrogels as Biomaterials." Macromol. Biosci. 6(2006):623-633.
Babensee et al. "Host Response to Tissue Engineered Device." Adv. Drug Deli. Rev. 33.1-2(1998):111-139.
Bachelder et al. "Acid-Degradable Polyurethane Particles for Protein-Based Vaccines: Biological Evaluation and in Vitro Analysis of Particle Degradation Products." Mol. Pharm. 5.5(2008):876-884.
Bachem et al. "Superior Antigen Cross-Presentation and XCR1 Expression Define Human CD11c+CD141+ Cells as Homologues of Mouse CD8+ Dendritic Cells." J. Exp. Med. 207.6(2010):1273-1281.
Badovinac et al. "Regulation of CD8 T+ Cells Undergoing Primary and Secondary Responses to Infection in the Same Host." J. Immunol. 170(2003):4933-4942.
Bakri et al. "Pharmacokinetics of Intravitreal Bevacizumab (Avastin)." Ophthalmology. 114.5(2007):855-859.
Balakrishna et al. "Structural Correlates of Antibacterial and Membrane-Permeabilizing Activities in Acylpolyamines." Antimicrob. Agents Chemother. 50.3(2006):852-861.
Banchereau et al. "Dendritic Cells and the Control of Immunity." Nature. 392.6673(1998):245-252.
Bar-Cohen et al. "Electroactive Polymer Actuators and Sensors." MRS Bullet. 33.3(2008):173-181.

(56) References Cited

OTHER PUBLICATIONS

Bar-Or et al. "Induction of Antigen-Specific Tolerance in Multiple Sclerosis after Immunization with DNA Encoding Myelin Basic Protein in a Randomized, Placebo-Controlled Phase 1/2 Trial." Arch. Neurol. 64.10(2007):1407-1415.
Barbero et al. "Growth Factor Supplemented Matrigel Improves Ectopic Skeletal Muscle Formation—A Cell Therapy Approach." J. Cell. Physiol. 186(2001):183-192.
Barrio et al. "A Two-Dimensional Numerical Study of Spatial Pattern Formation in Interacting Turing Systems." Bull. Math Biol. 61.3(1999):483-505.
Bates. "Improved Muscle Regeneration by Combining VEGF With IGF1." Regen. Med. 5.6(2010):853-854.
Beaucage et al. "The Functionalization of Oligonucleotides via Phosphoramidite Derivatives." Tetrahedron. 49.10(1993):1925-1963.
Beauchamp et al. "Dynamics of Myoblast Transplantation Reveal a Discrete Minority of Precursors with Stem Cell-Like Properties as the Myogenic Source." J. Cell Biol. 144.6(1999):1113-1122.
Becker et al. "Cytological Demonstration of the Clonal Nature of Spleen Colonies Derived from Transplanted Mouse Marrow Cells." Nature. 197(1963):452-454.
Beebe et al. "Functional Hydrogel Structures for Autonomous Flow Control Inside Microfluidic Channels." Nature. 404(2000):588-590.
Bekiari et al. "Study of Poly(N,N-dimethylacrylamide)/CdS Nanocomposite Organic/Inorganic Gels." Langmuir. 20.19(2004):7972-7975.
Bell. "Models for the Specific Adhesion of Cells to Cells." Science. 200.4342(1978):618-627.
Bencherif et al. "Influence of Cross-Linker Chemistry on Release Kinetics of PEG-co-PGA Hydrogels." J. Biomed. Mater. Res. A. 90.1(2009):142-153.
Bencherif et al. "End-Group Effects on the Properties of PEG-co-PGA Hydrogels." Acta Biomater. 5.6(2009):1872-1883.
Bencherif et al. "Influence of the Degree of Methacrylation of Hyaluronic Acid Hydrogels Properties." Biomater. 29.12(2008):1739-1749.
Bencherif et al. "Injectable Preformed Scaffolds with Shape-Memory Properties." PNAS. 109.48(2012):19590-19595.
Bencherif et al. "Nanostructured Hybrid Hydrogels Prepared by a Combination of Atom Transfer Radical Polymerization and Free Radical Polymerization." Biomater. 30.29(2009):5270-5278.
Bencherif et al. "Synthesis by AFET ATRP of Degradable Nanogel Precursors for in situ Formation of Nanostructured Hyaluronic Acid Hydrogel." Biomacromol. 10.9(2009):2499-2507.
Benton et al. "Photocrosslinking of Gelatin Macromers to Synthesize Porous Hydrogels that Promote Valvular Interstitial Cell Function." Tissue Eng. Part A. 15.11(2009):3221-3230.
Berg et al. "IL-10 is a Central Regulator of Cyclooxygenase-2 Expression and Prostaglandin Production." J. Immunol. 166.4(2001):2674-2680.
Bergstraesser et al. "Stimulation and Inhibition of Human Mammary Epithelial Cell Duct Morphogenesis In Vitro." Proc. Assoc. Am. Physicians. 108.2(1996):140-154.
Bianco et al. "The Meaning, the Sense and the Significance: Translating the Science of Mesenchymal Stem Cells into Medicine." Nat. Med. 19.1(2013):35-42.
Bilodeau. "Regular Pyramid Punch Problem." J. Appl. Mech. 59.3(1992):519-523.
Bischoff. "Proliferation of Muscle Satellite Cells on Intact Myofibers in Culture." Dev. Biol. 115.1(1986):129-139.
Blanas et al. "Induction of Autoimmune Diabetes by Oral Administration of Autoantigen." Science. 274.5293(1996):1707-1709.
Blumenthal et al. "Polyurethane Scaffolds Seeded with Genetically Engineered Skeletal Myoblasts: A Promising Tool to Regenerate Myocardial Function." Artificial Organs. 34.2(2010):E46-E54.
Boateng et al. "Wound Healing Dressings and Drug Delivery Systems: A Review." J. Pharm. Sci. 97.8(2008):2892-2923.
Boerckel et al. "Mechanical Regulation of Vascular Growth and Tissue Regeneration in vivo." PNAS. 108.37(2011):E674-E680.
Bohl et al. "Role of Synthetic Extracellular Matrix in Development of Engineered Dental Pulp." J. Biomater. Sci. Polym. Ed. 9.7(1998):749-764.
Bonauer et al. "MicroRNA-92a Controls Angiogenesis and Functional Recovery of Ischemic Tissues in Mice." Science. 324.5935(2009):1710-1713.
Boontheekul et al. "Controlling Alginate Gel Degradation Utilizing Partial Oxidation and Bimodal Molecular Weight Distribution." Biomaterials. 26.15(2005):2455-2465.
Boontheekul et al. "Regulating Myoblast Phenotype Through Controlled Gel Stiffness and Degradation." Tissue Engin. 13.7(2007):1431-1442.
Borselli et al. "Functional Muscle Regeneration with Combined Delivery of Angiogenesis and Myogenesis Factors." PNAS. 107.8(2010):3287-3292.
Bouhadir et al. "Degradation of Partially Oxidized Alginate and its Potential Application for Tissue Engineering." Biotechnol. Prog. 17.5(2001):945-950.
Bouhadir et al. "Synthesis of Cross-Linked Poly(aldehyde guluronate) Hydrogels." Polymer. 40(1999):3575-3584.
Bowne et al. "Injection of DNA Encoding Granulocyte-Macrophage Colony-Stimulating Factor Recruits Dendritic Cells for Immune Adjuvant Effects." Cytokines Cell Mol. Ther. 5.4(1999):217-225.
Brignone et al. "A Phase I Phamacokinetic and Biological Correlative Study of IMP321, a Novel MHC Class II Agonist, in Patients with Advanced Renal Cell Carcinoma." Clin. Cancer Res. 15.19(2009):6225-6231.
Brinkman et al. "Photo-Cross Linking of Type 1 Collagen Gels in the Presence of Smooth Muscle Cells: Mechanical Properties, Cell Viability, and Function." Biomacromolecules. 4.4(2003):890-895.
Brinkmann et al. "Neutrophil Extracellular Traps Kill Bacteria." Science. 303.5663(2004):1532-1535.
Brouwers et al. "Can the Growth Factors PTHrP, Ihh and VEGF, Together Regulate the Development of a Long Bone?" J. Biomech. 39.15(2006):2774-2782.
Broxmeyer et al. "Insights into the Biology of Cord Blood Stem/Progenitor Cells." Cell Prolif. 44.S1(2011):55-59.
Brunner et al. Enhanced dendritic cell maturation by TNF-alpha or cytidine-phosphate-guanosine DNA drives T cell activation in vitro and therapeutic anti-tumor immune responses in vivo. J Immunol. Dec. 1, 2000;165(11):6278-86.
Bryant et al. "Photo-Patterning of Porous Hydrogels for Tissue Engineering." Biomater. 28.19(2007):2978-2986.
Buckwalter et al. "Form of Antigen Dictates Immunity: Irradiated Cell vs. Whole Cell Lysate Vaccination." J. Immunol. 178(2007).
Bullard et al. "Fetal Wound Healing: Current Biology." World J. Surg. 27.1(2003):54-61.
Buonaguro et al. "Translating Tumor Antigens into Cancer Vaccines." Clin. Vaccine Immunol. 18.1(2011):23-34.
Burdick et al. "Controlled Degradation and Mechanical Behavior of Photopolymerized Hyaluronic Acid Networks." Biomacromol. 6.1(2005):386-391.
Burdick et al. "Photoencapsulation of Osteoblasts in Injectable RGD-Modified PEG Hydrogels for Bone Tissue Engineering." Biomater. 23.22(2002):4315-4323.
Burdick et al. "Stimulation of Neurite Outgrowth by Neurotrophins Delivered From Degradable Hydrogels." Biomater. 27.3(2006):452-459.
Bégué et al. "Vaccination Against Human Papillomavirus. Implementation and Efficacy Against Cervical Cancer Control." Bull. Acad. Natl. Med. 191.9(2007):1805-1816. (French original and English abstract).
Bürger et al. "Effect of VEGF and its Receptor Antagonist SU-5416, an Inhibitor of Angiogenesis, on Processing of the β-amyloid Precursor Protein in Primary Neuronal Cells Derived From Brain Tissue of Tg2576 Mice." Int. J. Dev. Neurosci. 28.7(2010):597-604.
Calvert. "Electroactive Polymer Gels." Electroactive Polymer (EAP) Acutators as Artificial Muscle: Reality, Potential, and Challenges. Bar-Cohen, ed. Bellingham, WA: Spie Press. (2004):151-170.
Calvert. "Gel Sensors and Actuators." MRS Bullet. 33.3(2008):207-212.

(56) References Cited

OTHER PUBLICATIONS

Cameron et al. "The Influence of Substrate Creep on Mesenchymal Stem Cell Behaviour and Phenotype." Biomater. 32.26(2011):5979-5993.
Cao et al. "Promoting Angiogenesis via Manipulation of VEGF Responsiveness with Notch Signaling." Biomater. 30.25(2009):4085-4093.
Carlson et al. "Notch Signaling Pathway and Tissue Engineering." Front. Biosci. 12(2007):5143-5156.
Carmeliet et al. "Angiogenesis in Cancer and Other Diseases." Nature. 407.6801(2000):249-257.
Carmeliet. "Mechanisms of Angiogenesis and Arteriogenesis." Nat. Med. 6.3(2000):389-395.
Caulfield et al. "Regulation of Major Histocompatibility Complex Class II Antigens on Human Alveolar Macrophages by Granulocyte-Macrophage Colony-Stimulating Factor in the Presence of Glucocorticoids." Immunol. 98.1(1999):104-110.
Ceriello et al. "Clinical Review 2: The 'Metabolic Meory': Is more than just Tight Glucose Control Necessary to Prevent Diabetic Complications?" J. Clin. Endocrinol. Metab. 94.2(2009):410-415.
Ceriello et al. "The Emerging Challenge in Diabetes: The 'Metabolic Memory.'" Vascular Pharmacol. 57.5-6(2012):133-138.
Chan et al. "Antifibrotic Effects of Suramin in Injured Skeletal Muscle After Laceration." J. Appl. Physiol. 95(2003):771-780.
Chan et al. "Helix Induction in Antimicrobial Peptides by Alginate in Biofilms." J. Biol. Chem. 279.37(2004):38749-38754.
Chan et al. "Traction Dynamics of Filopodia on Compliant Substrates." Science. 322.5908(2008):1687-1691.
Chang. "Mouse Models for Studies of Retinal Degeneration and Diseases." Methods Mol. Biol. 935(2013):27-39.
Chen et al. "Adipogenic Differentiation of Adipose Tissue-Derived Human Mesenchymal Stem Cells: Effects of Gastic Bypass Surgery." Surg. Endosc. 26(2012):3449-3456.
Chen et al. "Functional Human Vascular Network Generated in Photocrosslinkable Gelatin Methacrylate Hydrogels." Adv. Funct. Mater. 22.10(2012):2027-2039.
Chen et al. "Integrated Approach to Designing Growth Factor Delivery Systems." FASEB J. 21.14(2007):3896-3903.
Chen et al. "Polymeric Growth Factor Delivery Strategies for Tissue Engineering." Pharm. Res. 20.8(2003):1103-1112.
Chen et al. "Skeletal Muscle Stem Cells." Reprod. Biol. Endocrinol. 1(2003):101.
Chen et al. "Spatio-Temporal VEGF and PDGF Delivery Patterns Blood Vessel Formation and Maturation." Pharm. Res. 24.2(2007):258-264.
Chiang et al. "Whole Tumor Antigen Vaccines." Semin. Immunol. 22.3(2010):132-143.
Choi et al. "In Vitro Mineralization by Preosteoblasts in Poly(DL-lactide-co-glycolide) Inverse Opal Scaffolds Reinforced with Hydrozyapatite Nanoparticles." Langmuir. 26.14(2010):12126-12131.
Choi et al. "Three-Dimentional Scaffolds for Tissue Engineering: The Importance of Uniformity in Pore Size and Structure." Langmuir. 26.24(2010):19001-19006.
Choi. "Replacement Organs, Hot Off the Press." New Scientist. 177.2379(2003):16.
Chou et al. "Characterization of Photocross Linked Alginate Hydrogels for Nucleus Pulposus Cell Encapsulation." J. Biomed. Mater. Res. A. 91A.1(2009):187-194.
Chromiak et al. "Bioreactor Perfusion System for the Long-Term Maintenance of Tissue-Engingeered Skeletal Muscle Organoids." In Vitro Cell Dev. Biol. Anim. 34.9(1998):694-703.
Clark et al. "Myosin II and Mechanotransduction: A Balancing Act." Trends Cell Biol. 17.4(2007):178-186.
Clauss et al. "Interstitial Transport of Rabbit and Sheep Antibodies in Normal and Neoplastic Tissues." Cancer Res. 50.12(1990):3487-3492.
Cohen et al. "Controlled Delivery Systems for Proteins Based on Poly(Lactic/Glycolic Acid) Microspheres." Pharm. Res. 8.6(1991):713-720.
Comisar et al. "Engineering RGD Nanopatterned Hydrogels to Control Preosteoblast Behavior: A Combined Computational and Experimental Approach." Biomaterials. 28(2007):4409-4417.
Conboy et al. "The Regulation of Notch Signaling Controls Satellite Cell Activation and Cell Fate Determination in Postnatal Myogenesis." Dev. Cell. 3.3(2002):397-409.
Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." J. Biomed. Mater. Res. 89A.2(2009):304-316.
Conn et al. "Purification of a Glycoprotein Vascular Endothelial Cell Mitogen From a Rat Glioma-Derived Cell Line." PNAS. 87.4(1990):1323-1327.
Cook et al. "A Sialomucopeptide Liberated by Trypsin from the Human Erythrocyte." Nature. 188(1960):1011-1012.
Cooper et al. "Extended Amplification In Vitro and Replicative Senescence: Key Factors Implicated in the Success of Human Myoblast Transplantation." Hum. Gene Ther. 14(2003):1169-1179.
Cooper, "Metabolic Memory: Implications for Diabetic Vascular Complications." Pediatr. Diabetes. 10.5(2009):343-346.
Corcione et al. "CCL19 and CXCL12 trigger in vitro chemotaxis of human mantle cell lymphoma B cells." Clin CancerRes. Feb. 1, 2004;10(3):964-71.
Cornelison et al. "Single-Cell Analysis of Regulatory Gene Expression in Quiescent and Activated Mouse Skeletal Muscle Satellite Cells." Dev. Biol. 191.2(1997):270-283.
Cornelison et al. "Syndecan-3 and Syndecan-4 Specifically Mark Skeletal Muscle Satellite Cells and Are Implicated in Satellite Cell Maintenance and Muscle Regeneration." Dev. Biol. 239.1(2001):79-94.
Coulson et al. "Flow of Fluids through Granular Beds and Packed Columns." Chemical Engineering. New York: Pergamon Press. 2(1978):125-171.
Crameri et al. "Improved Green Fluorescent Protein by Molecular Evolution Using DNA Shuffling." Nat. Biotechnol. 14.3(1996):315-319.
Cuda et al. "In Vitro Actin Filament Sliding Velocities Produced by Mixtures of Different Types of Myosin." Biophys. J. 72.4(1997):1767-1779.
Cukierman et al. "Taking Cell-Matrix Adhesions to the Third Dimension." Science. 294.5547(2001):1708-1712.
Cullen et al. "Investigation of Vascular Endothelial Growth Factor Effects on Pulmonary Endothelial Monolayer Permeability and Neutrophil Transmigration." Gen. Pharmacol. 35.3(2000):149-157.
Curiel et al. "Tumor Immunotherapy: Inching Toward the Finish Line." J. Clin. Invest. 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." J. Exp. Med. 198.2(2003):293-303.
Dar et al. "Optimization of Cardiac Cell Seeding and Distribution in 3D Porous Alginate Scaffolds." Biotechnol. Bioeng. 80(2002):305-312.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." J. Immunol. 165.1(2000):49-58.
David et al. "The in vitro Desensitization of Sensitive Cells by Trypsin." J. Exp. Med. 120(1964):1189-1200.
Davies et al. "Antibody-Antigen Complexes." Annu. Rev. Biochem. 59(1990):439-473.
de Jong et al. "Regulation of Notch Signaling Genes During BMP2-Induced Differentiation of Osteoblast Precursor Cells." Biochem. Biophys. Res. Commun.320(2004):100-107.
De Temmerman et al. "Particulate Vaccines: On the Quest for Optimal Delivery and Immune Response." Drug Disc. Today. 16.13&14(2011):569-582.
Dembo et al. "Stresses at the Cell-to-Substrate Interface During Locomotion of Fibroblasts." Biophys. J. 76.4(1999):2307-2316.
den Haan et al. "CD8+ by not CD8− Dendritic Cells Cross-Prime Cytotoxic T Cells In Vivo." J. Exp. Med. 192.12(2000):1685-1696.

(56) References Cited

OTHER PUBLICATIONS

Dennis et al. "Excitability and Contractility of Skeletal Muscle Engineered From Primary Cultures and Cell Lines." Am. J. Physiol. Cell Physiol. 280(2001):C288-C295.
Dennis et al. "Excitability and Isometric Contractile Properties of Mammalian Skeletal Muscle Constructs Engineered in vitro." In Vitro Cell Dev. Biol. Anim. 36.5(2000):327-335.
Dexter et al. "Conditions Controlling the Proliferation of Haemopoietic Stem Cells In Vitro." J. Cell. Physiol. 91.3(1977):335-344.
Di Nicola et al. "Human Bone Marrow Stromal Cells Suppress T-Lymphocyte Proliferation Induced by Cellular or Nonspecific Mitogenic Stimuli." Blood. 99.10(2002):3838-3843.
Diduch et al. "Two Cell Lines from Bone Marrow tht Differ in Terms of Collagen Synthesis, Osteogenic Characteristics, and Matrix Mineralization." J. Bone Joint Surg. Am. 75.1(1993):92-105.
Dieu et al. "Selective Recruitment of Immature and Mature Dendritic Cells by Distinct Chemokines Expressed in Different Anatomic Sites." J. Exp. Med. 188(1988):373-386.
Diridollou et al. "Skin Ageing: Changes of Physical Properties of Human Skin in vivo." J. Cosmet. Sci. 23.6(2001):353-362.
Discher et al. "Tissue Cells Feel and Respond to the Stiffness of their Substrate." Science. 310.5751(2005):1139-1143.
Disis et al. "Granulocyte-Macrophage Colony-Stimulating Factor: An Effective Adjuvant for Protein and Peptide-Based Vaccines." Blood. 88.1(1996):202-210.
Doan et al. "Subcellular Localization of a Sporulation Membrane Protein is Achieved Through a Network of Interactions Along and Across the Septum." Mol. Microbiol. 55.6(2005):1767-1781.
Donati et al. "New Hypothesis on the Role of Alternating Sequences in Calcium-Alginate Gels." Biomacromol. 6.2(2005):1031-1040.
Dor et al. "Making Vascular Networks in the Adult: Branching Morphogenesis Without a Roadmap." Trends Cell Biol. 13.3(2003):131-136.
Douay et al. "Ex vivo Production of Human Red Blood Cells from Hematopoietic Stem Cells: What is the Future in Transfusion?" Transfus. Med. Rev. 21.2(2007):91-100.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." PNAS. 90.8(1993):3539-3543.
Dranoff. "Cyotkines in Cancer Pathogenesis and Cancer Therapy." Nat. Rev. Cancer. 4.1(2004):11-22.
Dranoff. "GM-CSF-Based Cancer Vaccines." Immunol. Rev. 188(2002):147-154.
Dudley et al. "Adoptive Cell Transfer Therapy Following Non-Myeloablative by Lymphodepleting Chemotherapy for the Treatment of Patients with Refractory Metastatic Melanoma." J. Clin. Oncol. 23.10(2005):2346-2357.
DuFort et al. "Balancing Forces: Architectural Control of Mechanotransduction." Nat. Rev. Mol. Cell Biol. 12.5(2011):308-319.
Dupont et al. "Role of YAP/TAZ in Mechanotransduction." Nature. 474.7350(2011):179-183.
Edwards et al. "Evaluation of Biomechanical Properties of Human Skin." Clin. Dermatol. 13.4(1995):375-380.
Egholm et al. "Peptide Nucleic Acids (PNA). Oligonucleotide Analogues with an Achiral Peptide Backbone." J. Am. Chem. Soc. 114.5(1992):1895-1897.
Egholm et al. "PNA Hybridizes to Complementary Oligonucleotides Obeying the Watson-Crick Hydrogen-Bonding Rules." Nature. 365.6446(1993):566-568.
Ehrbar et al. "Endothelial Cell Proliferation and Progenitor Maturation by Fibrin-Bound VEGF Variants with Differential Susceptibilities to Local Cellular Activity." J. Control. Release. 101(2004):93-109.
Eiselt et al. "Porous Carriers for Biomedical Applications Based on Alginate Hydrogels." Biomat. 21.19(2000):1921-1927.
El-Backly et al. "Regeneration of Dentine/Pulp-Like Tissue Using a Dental Pulp Stem Cell/Poly(Lactic-Co-Glycolic) Acid Scaffold Construct in New Zealand White Rabbits." Aust. Endod. J. 34.2(2008):52-67.
Eldar et al. "Elucidating Mechanisms Underlying Robustness of Morphogen Gradients." Curr. Opin. Genet. Dev. 14.4(2004):435-439.
Eldar et al. "Robustness of the BMP Morphogen Gradient in *Drosophila* Embryonic Patterning." Nature. 419.6904(2002):304-308.
Eldar et al. "Self-Enhanced Ligand Degradation Underlies Robustness of Morphogen Gradients." Dev. Cell. 5.4(2003):635-646.
Eming et al. "Inflammation in Wound Repair: Molecular and Cellular Mechanisms." J. Invest. Dermatol. 127.3(2007):514-525.
Engler et al. "Matrix Elasticity Directs Stem Cell Lingeage Specification." Cell. 126.4(2006):677-689.
Engler et al. "Microtissue Elasticity: Measurements by Atomic Force Microscopy and its Influence on Cell Differentiation." Methods Cell. Biol. 83(2007):521-545.
Engler et al. "Substrate Compliance Versus Ligand Density in Cell on Gel Response." Biophys. J. 86.1Pt1(2004):617-628.
Ennett et al. "Temporally Regulated Delivery of VEGF in vitro and in vivo." J. Biomed. Mater. Res. A. 79.1(2006):176-184.
Exposito et al. "The Fibrallar Collagen Family." Int. J. Mol. Sci. 11.2(2010):407-426.
Faissner et al. "Boundaries and Inhibitory Molecules in Developing Neural Tissues." Glia. 13.4(1995):233-254.
Falanga. "Wound Healing and its Impairment in the Diabetic Foot." Lancet. 366.9498(2005):1736-1743.
Falsey et al. "Peptide and Small Molecule Microarray for High Throughput Cell Adhesion and Functional Assays." Bioconjug. Chem. 12.3(2001):346-353.
Farrar et al. "T Helper Subset Development: Roles of Instruction, Selection, and Transcription." J. Clin. Invest. 109.4(2002):431-435.
Fauquemberque et al. "HLA-A*0201-Restricted CEA-Derived Peptide CAP1 is not a Suitable Target for T-Cell-Based Immunotherapy." J. Immunother. 33.4(2010):402-413.
Ferrara et al. "Angiogenesis as a Therapeutic Target." Nature. 438.7070(2005):967-974.
Ferrara et al. "Discovery and Development of Bevacizumab, an Anti-VEGF Antibody for Treating Cancer." Nat. Rev. Drug Discov. 3.5(2004):391-400.
Fischer et al. "A Brilliant Monomeric Red Fluorescent Protein to Visualize Cytoskeleton Dynamics in Dictyostelium." FEBS Lett. 577.1-2(2004):227-232.
Fischer et al. "Visualizing Cytoskeleton Dynamics in Mammalian Cells Using a Humanized Variant of Monomeric Red Fluorescent Protein." FEBS Lett. 580.10(2006):2495-2502.
Fisher et al. "The Study of Protein Mechanics with the Atomic Force Microscope." Trends Biochem. Sci. 24.10(1999):379-384.
Folkman. "Angiogenesis." Annu. Rev. Med. 57(2006):1-18.
Fonseca et al. "Capitalizing on the Immunogenicity of Dying Tumor Cells." Clin. Cancer Res. 14.16(2008):1603-1608.
Fontaine et al. "Surgical Treatment of Peripheral Circulation Disorders." Helv. Chir. Acta. 21.56(1954):499-533.
Fox. "Management of Worsening Multiple Sclerosis with Mitoxantrone: A Review." Clin. Ther. 28(2006):461-474.
Fransen et al. "Local immunomodulation for cancer therapy: Providing treatment where needed." Oncoimmunology. Nov. 1, 2013;2(11):e26493.
Friedenstein et al. "Fibroblast Precursors in Normal and Irradiated Mouse Hematopoietic Organs." Exp. Hematol. 4.5(1976):267-274.
Friedrich et al. "Promoter Traps in Embryonic Stem Cells: A Genetic Screen to Identify and Mutate Developmental Genes in Mice." Genes Dev. 5(1991):1513-1523.
Fukushima et al. "The Use of an Antifibrosis Agent to Improve Muscle Recovery After Laceration." Am. J. Sports Med. 29.4(2001):394-402.
Furqan et al. STAT inhibitors for cancer therapy. J Hematol Oncol. Dec. 5, 2013;6:90.
Gamvrellis et al. "Vaccines that Facilitate Antigen Entry into Dendritic Cells." Immunol. Cell Biol. 82(2004):506-516.

(56) References Cited

OTHER PUBLICATIONS

Gardel et al. "Traction Stress in Focal Adhesions Correlates Biphasically with Actin Retrograde Flow Speed." J. Cell Biol. 183.6(2008):999-1005.
Gasic et al. "Removal and Regeneration of the Cell Coating in Tumour Cells." Nature. 196(1962):170.
Gauthier et al. "Temporary Increase in Plasma Membrane Tension Coordinates the Activation of Exocytosis and Contraction During Cell Spreading." PNAS. 108.35(2011):14467-14472.
Geerligs et al. "Linear Viscoelastic Behavior of Subcutaneous Adipose Tissue." Biorheol. 45.6(2008):677-688.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000230.2, Dec. 17, 2012.
GenBank Accession No. NM_000514.3, Aug. 19, 2012.
GenBank Accession No. NM_000572.2, May 18, 2014.
GenBank Accession No. NM_000601.4, Nov. 25, 2012.
GenBank Accession No. NM_000614.3, Sep. 9, 2012.
GenBank Accession No. NM_000638.3, May 4, 2014.
GenBank Accession No. NM_000660.4, Dec. 9, 2012.
GenBank Accession No. NM_000758.3, May 4, 2014.
GenBank Accession No. NM_000800.3, Mar. 4, 2012.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_001845.4, May 3, 2014.
GenBank Accession No. NM_001901.2, May 18, 2014.
GenBank Accession No. NM_002421.3_05112014.
GenBank Accession No. NM_002506.2, Dec. 9, 2012.
GenBank Accession No. NM_002632.4, May 4, 2011.
GenBank Accession No. NM_002982.3, May 3, 2014.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_003377.4, May 5, 2014.
GenBank Accession No. NM_003392.4, May 5, 2014.
GenBank Accession No. NM_004469.4, May 25, 2014.
GenBank Accession No. NM_005429.3, Mar. 31, 2014.
GenBank Accession No. NM_006068.4, Oct. 28, 2012.
GenBank Accession No. NM_015719.3, Feb. 26, 2014.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001096124.1, Dec. 16, 2012.
GenBank Accession No. NP_001836.2, May 3, 2014.
GenBank Accession No. NP_001892.1, May 18, 2014.
GenBank Accession No. NP_002010.2, Dec. 9, 2012.
GenBank Accession No. NP_002973.1, May 3, 2014.
GenBank Accession No. NP_003239.2, Feb. 18, 2014.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_003368.1, May 5, 2014.
GenBank Accession No. NP_003383.2, May 5, 2014.
GenBank Accession No. NP_004460.1, May 25, 2014.
GenBank Accession No. NP_005420.1, May 11, 2014.
GenBank Accession No. NP_006059.2, Oct. 28, 2012.
GenBank Accession No. NP_056534.2, Feb. 26, 2014.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
GenBank Accession No. U76381.2, Jul. 12, 1999.
Genes et al. "Effect of Substrate Mechanics on Chondrocyte Adhesion to Modified Alginate Surfaces." Arch. Biochem. Biophys. 422.2(2004):161-167.
Gerhardt et al. "VEGF Guides Angiogenic Sprouting Utilizing Endothelial Tip Cell Filopodia." J. Cell Biol. 161.6(2003):1163-1177.
Gilboa. "Dendritic-Cell Based Cancer Vaccines." J. Clin. Invest. 117.5(2007):1195-1203.
Glasbey et al. "Image Analysis and Three-Dimensional Modelling of Pores in Soil Aggregates." Eur. J. Soil Sci. 42.2(1991):479-486.
Gnjatic et al. "Toll-Like Receptor Agonists: Are They Good Adjuvants?" Cancer J. 16.4(2010):382-391.
Godbey et al. "Size Matters: Molecular Weight Affects the Efficiency of Poly(ethylenimine) as a Gene Delivery Vehicle." J. Biomed. Mater. Res. 45.3(1999):268-275.

(56) References Cited

OTHER PUBLICATIONS

Godbey et al. "Tracking the Intracellular Path of Poly(ethylenimine)/DNA Complexes for Gene Delivery." PNAS. 96.9(1999):5177-5181.
Gospodarowicz et al. "Effect of Fibroblast Growth Factor on the Division and Fusion of Bovine Myoblasts." J. Cell Biol. 70.2(1976):395-405.
Graessley. "Entangled Linear, Branched and Network Polymer Systems—Molecular Theories." Adv. Poly. Sci. 47(1982):67-117.
Griffith et al. "Tissue Engineering—Current Challenges and Expanding Opportunities." Science. 295(2002):1009-1014.
Grimmer et al. "Tracheal Reconstruction Using Tissue-Engineered Cartilage." Arch. Otolaryngol. Head Neck Surg.130.10(2004):1191-1196.
Gros et al. "A Common Somitic Origin for Embryonic Muscle Progenitors and Satellite Cells." Nature. 435(2005):954-958.
Guillaume et al. "Two Abundant Proteasome Subtypes that Uniquely Process Some Antigens Presented by HLA Class I Molecules." PNAS. 107.43(2010):18599-18604.
Gullberg et al. "Extracellular Matrix and Its Receptors During Development." Int. J. Dev. Biol. 39(1995):845-854.
Guo et al. "Droplet Microfluidics for High-Throughput Biological Assays." Lab Chip. 12.12(2012):2146-2155.
Gupta et al. "Magnetically Controlled Targeted Micro-Carrier Systems." Life Sci. 44.3(1989):175-186.
Gurkan et al. "The Mechanical Environment of Bone Marrow: A Review." Ann. Biomed. Eng. 36.12(2008):1978-1991.
Gussoni et al. "Dystophin Expression and in the mdx Mouse Restored by Stem Cell Transplantation." Nature. 401(1999):390-394.
Halim et al. "Biologic and Synthetic Skin Substitutes: An Overview." Indian J. Plast. Surg. 43(2010):S23-S28.
Hamby et al. "Small Molecule Inhibitors of Tumor-Promoted Angiogenesis, Including Protein Tyrosine Kinase Inhibitors." Pharmacol. Ther. 82.2-3(1999):169-193.
Hamdy et al. "Targeting Dendritic Cells with Nano-Particulate PLGA Cancer Vaccine Formulations." Adv. Drug Deliv. Rev. 63.10(2011):943-955.
Hamilton et al. "GM-CSF Biology." Growth Factors. 22.4(2004):225-231.
Hamilton. "GM-CSF in Inflammation and Autoimmunity." Trends Immunol. 23.8(2002):403-408.
Hanada. "Efficacy of Rehabilitative Therapy in Regional Musculoskeletal Conditions." Best Pract. Res. Clin. Rheumatol. 17.1(2003):151-166.
Hansen et al. "Comparison of Clinical Grade Type 1 Polarized and Standard Matured Dendritic Cells for Cancer Immunotherapy." Vaccine. 31.4(2013):639-646.
Hansen et al. "Integrin Binding and Cell Spreading on Extracellular Matrix Act at Different Points in the Cell Cycle to Promote Hepatocyte Growth." Mol. Biol. Cell. 5(1994):967-975.
Harris et al. "Open Pore Biodegradable Matrices Formed with Gas Foaming." J. Biomed. Mater. Res. 42.3(1998):396-402.
Harris. "Classification, Diagnostic Criteria, and Screening for Diabetes." Diabetes in America. NIH Publication No. 95-1468. Chapter 2. (1995):15-36.
Harrison. "What is the Status of Reaction-Diffusion Theory Thirty-Four Years After Turing?" J. Theor. Biol. 125.4(1987):369-384.
Hartgerink et al. "Peptide-Amphiphile Nanofibers: A Versatile Scaffold for the Preparation of Self-Assembling Materials." PNAS. 99.8(2002):5133-5138.
Hartmann et al. "CpG DNA: A Potent Signal for Growth, Activation, and Maturation of Human Dendritic Cells." PNAS. 96(1999):9305-9310.
Hashimoto et al. "Development of Alginate Wound Dressings Linked with Hybrid Peptides Derived from Laminin and Elastin." Biomaterials. 25.7-8(2004):1407-1414.
Hawke et al. "Myogenic Satellite Cells: Physiology to Molecular Biology." J. Appl. Physiol. 91(2001):534-551.
Heath. "Cells for Tissue Engineering." Trends Biotechnol. 18.1(2006):17-19.
Helm et al. "Synergy Between Interstitial Flow and VEGF Directs Capillary Morphogenesis in vitro Through a Gradient Amplification Mechanism." PNAS. 102.44(2005):15779-15784.
Henry et al. "The VIVA Trial: Vascular Endothelial Growth Factor in Ischemia for Vascular Angiogenesis." Circulation. 107.10(2003):1359-1365.
Hermanson. Bioconjugate Techniques. New York: Academic Press. (1996):152-185.
Heslop et al. "Transplanted Primary Neonatal Myoblasts can Give Rise to Functional Satellite Cells as Identified Using the Myf5nlacZl+ Mouse." Gene Ther. 8(2001):778-783.
Hildner et al. "Batf3 Deficiency Reveals a Critical Role for CD8α+ Dendritic Cells in Cytotoxic T Cell Immunity." Science. 322.5904(2008):1097-1100.
Hill et al. "Designing Scaffolds to Enhance Transplanted Myoblast Survival and Migration." Tissue Engin. 12.5(2006):1295-1304.
Hill et al. "Muscle Satellite (Stem) Cell Activation During Local Tissue Injury and Repair." J. Anat. 203.1(2003):89-99.
Hill. "Macroporous Scaffold Architecture, Peptide, HGF/FGF and Myoblast Incorporation Enhance Myogenesis." IADR/AADR/CADR 83rd General Session. (Mar. 9-12, 2005). Poster #2829.
Hirano et al. "Peptide and Protein Presenting Materials for Tissue Engineering." Adv. Mat. 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." PNAS. 95.23(1998):13806-13811.
Hodi et al. "Immunologic and Clinical Effects of Antibody Blockade of Cytotoxic T Lymphocyte-Associated Antigen 4 in Previously Vaccinated Cancer Patients." PNAS. 105.8(2008):3005-3010.
Holland et al. "Transforming Growth Factor-β1 Release from Oligo(poly(ethylene glycol) Fumarate) Hydrogels in Conditions that Model the Cartilage Wound Healing Environment." J. Control. Release. 94(2004):101-114.
Horsley et al. "IL-4 Acts as a Myoblast Recruitment Factor During Mammalian Muscle Growth." Cell. 113.4(2003):483-494.
Hsiong et al. "Differentiation Stage Alters Matrix Control of Stem Cells." J. Biomed. Mater. Res. Part A. 8(2007):145-156.
Huang et al. "Fabrication and in vitro Testing of Polymeric Delivery Systems for Condensed DNA." J. Biomed. Mater. Res. 67(2003):1384-1392.
Huang et al. "Long-Term In Vivo Gene Expression via Delivery of PEI-DNA Condensates From Porous Polymer Scaffolds." Hum. Gene Ther. 16.5(2005):609-617.
Hubbell et al. "Materials Engineering for Immunomodulation." Nature. 462(2009):449-460.
Hubbell. "Biomaterials in Tissue Engineering." Bio/Tech. 13(1995):565-576.
Huebsch et al. "Harnessing Traction-Mediated Manipulation of the Cell/Matrix Interface to Control Stem-Cell Fate." Nat. Mater. 9.6(2010):518-526.
Humphries et al. "Integrin Ligands at a Glance." J. Cell. Sci. 119.Pt19(2006):3901-3903.
Huston et al. "Protein Engineering of Antibody Binding Sites: Recovery of Specific Activity in an Anti-Digoxin Single-Chain Fv Analogue Produced in *Escherichia coli*." PNAS. 85.16(1988):5879-5883.
Hutson et al. "Synthesis and Characterization of Tunable Poly(ethylene Glycol): Gelatin Methacrylate Composite Hydrogels." Tissue Eng. Part A. 17.13-14(2011):1713-1723.
Hwang et al. "Fabrication of Three-Dimensional Porous Cell-Laden Hydrogel for Tissue Engineering." Biofabrication. 2.3(2010):035003.
Ichida et al. A small-molecule inhibitor of tgf-Beta signaling replaces sox2 in reprogramming by inducing nanog. Cell Stem Cell. Nov. 6, 2009;5(5):491-503.
Ihnat et al. "Hypothesis: The 'Metabolic Memory', the New Challenge of Diabetes." Diabet. Med. 24.6(2007)582-586.
Isern et al. "Self-Renewing Human Bone Marrow Mesenspheres Promote Hematopoietic Stem Cell Expansion." Cell Rep. 3.5(2013):1714-1724.

(56) References Cited

OTHER PUBLICATIONS

Ishihara et al. "Roles of Bradykinin in Vascular Permeability and Angiogenesis in Solid Tumor." Int. Immunopharmacol. 2.4(2002):499-509.
Iwamoto et al. "Preparation of an Ionic Polymer Gel Microactuator and Measurement of its Periodic Motions." Nippon Kagaku Kaishi. 9(1997):609-614. (Japanese Original and English Abstract).
Jain. "Molecular Regeneration of Vessel Maturation." Nat. Med. 9.6(2003):685-693.
Jain. "The Manufacturing Techniques of Various Drug Loaded Biodegradable Poly(lactide-co-glycolide) (PLGA) Devices." Biomater. 21.23(2000):2475-2490.
Jankovic et al. "In the Absence of IL-12, CD4+ T Cell Responses to Intracellular Pathogens Fail to Default to a Th2 Pattern and are Host Protective in an IL-10-/- Setting." Immunity. 16.3(2002):429-439.
Janmey et al. "From Tissue Mechanics to Transcription Factors." Differentiation. 86.3(2013):112-120.
Jego et al. "Plasmacytoid Dendritic Cells Induce Plasma Cell Differenetiation Through Type I Interferon and Interleukin 6." Immunity. 19.2(2003):225-234.
Jiang et al. "Self-Organization of Periodic Patterns by Dissociated Feather Mesenchymal Cells and the Regulation of Size, Number and Spacing of Primorida." Development. 126.22(1999):4997-5009.
Jiang et al. "Two-Piconewton Slip Bond Between Fibronectin and the Cytoskeleton Depends on Talin." Nature. 424.6946(2003):334-337.
Jinushi et al. "Enhancing the Clinical Activity of Granulocyte-Macrophage Colony-Stimulating Factor-Secreting Tumor Cell Vaccines." Immunol. Rev. 222(2008):287-298.
Jinushi et al. "MFG-E8-Mediated Uptake of Apoptotic Cells by APCs Links the Pro- and Antiinflammatory Activities of GM-CSF." J. Clin. Invest. 117.7(2007):1902-1913.
Johnson et al. "Activation of Skeletal Muscle Satellite Cells and the Role of Fibroblast Growth Factor Receptors." Exp. Cell Res. 219.2(1995):449-453.
Jokinen et al. "Integrin-Mediated Cell Adhesion to Type I Collagen Fibrils." J. Biol. Chem. 279.30(2004):31956-31963.
Jugdutt et al. "Aging and Defective Healing, Adverse Remodeling, and Blunted Post-Conditioning in the Reperfused Wounded Heart." J. Am. Coll. Cardiol. 51.14(2008):1399-1403.
Juntanon et al. "Electrically Controlled Release of Sulfosalicylic Acid from Crosslinked Poly(Vinyl Alcohol) Hydrogel." Int. J. Pharm. 356(2008):1-11.
Kang et al. "Effect of Porous Structure on the Degradation of Freeze-Dried Gelatin Hydrogels." J. Bioact. Compat. Poly. 14.4(1999):331-343.
Kanzler et al. "Therapeutic Targeting of Innate Immunity with Toll-Like Receptor Agaonists and Antagonists." Nat. Med. 13.5(2007):552-559.
Katayama et al. "Integrated Analysis of the Genome and the Transcriptome by FANTOM." Brief Bioinform. 5.3(2004):249-258.
Kathuria et al. "Synthesis and characterization of elastic and macroporous chitosan-gelatin cryogels for tissue engineerin" Act Abiomaterialia 5 (2009) 406-418.
Kawai et al. "Innate Immune Recognition of Viral Infection." Nat. Immunol. 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." J. Control. Release. 62.1-2(1999):279-287.
Kearney et al. "Macroscale Delivery Systems for Molecular and Cellular Payloads." Nat. Mater. 12.11(2013):1004-10017.
Kennedy et al. "Rapid and Extensive Collapse from Electrically Responsive Macroporous Hydrogels." Adv. Healthc. Mater. 3.4(2014):500-507.
Khetan et al. "Degradation-Mediated Cellular Traction Directs Stem Cell Fate in Covalently Crosslinked Three-Dimensional Hydrogels." Nat. Mater. 12.5(2013):458-465.
Khownium et al. "Novel Endotoxin-Compounds with Terephthalaldehyde-bis-guanyllhydrazone Scaffolds." Bioorg. Med. Chem. Lett. 16(2006):1305-1308.
Kim et al. "An Overview of Cartilage Tissue Engineering." Yonsei Med. J. 41.6(2000):766-773.
Kim et al. "Multifunctional Capsule-in-Capsules for Immunoprotection and Trimodal Imaging." Angew. Chem. Int. Ed. 50.10(2011):2317-2321.
Kim et al. "The Effect of VEGF on the Myogenic Differentiation of Adipose Tissue Derived Stem Cells Within Thermosensitive Hydrogel Matrices." Biomaterials. 31.6(2010):1213-1218.
Kinoshita et al. "Successive Injections in MDX Mice of Myoblasts Grown with bFGF." Neuromusc. Disord. 6.3(1996):187-193.
Kisak et al. "The Vesosome—A Multicompartment Drug Delivery Vehicle." Curr. Med. Chem. 11.2(2004):199-219.
Klebanoff et al. "CD8+ T-Cell Memory in Tumor Immunology and Immunotherapy." Immunol. Rev. 211(2006):214-224.
Klein et al. "Cell-Cycle Control by Physiological Matrix Elasticity and In Vivo Tissue Stiffening." Curr. Biol. 19.18(2009):1511-1518.
Klinman. "Immunotherapeutic Uses of CpG Oligodeoxynucleotides." Nat. Rev. Immunol. 4.4(2004):249-258.
Kohane. "Microparticles and Nanoparticles for Drug Delivery." Biotechnol. Bioeng. 96.2(2007):203-209.
Kondo et al. "A Reaction-Diffusion Wave on the Skin of the Marine Angelfish Pomacanthus." Nature. 376(2002):765-768.
Kong et al. "Controlling Degradation of Hydrogels via the Size of Crosslinked Junctions." Adv. Mater. 16.21(2004):1917-1921.
Kong et al. "Controlling Rigidity and Degradation of Alginate Hydrogels via Molecular Weight Distribution." Biomacromolec. 5.5(2004):1720-1727.
Kong et al. "Decoupling the Dependence of Rheological/Mechanical Properties of Hydrogels from Solids Concentration." Polymer. 43(2002):6239-6246.
Kong et al. "Design of Biodegradable Hydrogel for the Local and Sustained Delivery of Angiogenic Plasmid DNA." Pharma. Res. 25.5(2008):1230-1238.
Kong et al. "Designing Alginate Hydrogels to Maintain Viability of Immobilized Cells." Biomat. 24.22(2003):4023-4029.
Kong et al. "FRET Measurements of Cell-Traction Forces and Nano-Scale Clustering of Adhesion Ligands Varied by Substrate Stiffness." PNAS. 102.12(2005):4300-4305.
Kong et al. "Non-Viral Gene Delivery Regulated by Stiffness of Cell Adhesion Substrates." Nat. Mater. 4(2005):460-465.
Kratky et al. "Direct Activation of Antigen-Presenting Cells is Required for CD8+ T-Cell Priming and Tumor Vaccination." PNAS. 108.42(2011):17414-17419.
Krieg. "Development of TLR9 Agonists for Cancer Therapy." J. Clin. Invest. 117.5(2007):1184-1194.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kumamoto et al. "Induction of Tumor-Specific Protective Immunity by in situ Langerhans Cell Vaccine." Nat. BioTechnol. 20.1(2002):64-69.
Kumar et al. "Toll-Like Receptors and Innate Immunity." Biochem. Biophys. Res. Commun. 388.4(2009):621-625.
Kurts et al. "CD8 T Cell Ignorance or Tolerance to Islet Antigens Depends on Antigen Dose." PNAS. 96.22(1999):12703-12707.
Kuwahara et al. "Cell Delivery Using an Injectable and Adhesive Transglutaminase-Gelatin Gel." Tissue Eng. Part C Methods. 16.4(2010):609-618.
Kwon et al. "Electrically Erodible Polymer Gel for Controlled Release of Drugs." Nature. 354(1991):291-293.
Kwon et al. "In vivo Targeting Dendritic Cells for Activation of Cellular Immunity Using Vaccine Carriers Based on pH-Responsive Microparticles." PNAS. 102.51(2005):18264-18268.
Kyi C. Checkpoint blocking antibodies in cancer immunotherapy. FEBS Lett. Jan. 21, 2014;588(2):368-76.

(56) References Cited

OTHER PUBLICATIONS

Langenkamp et al. "Kinetics of Dendritic Cell Activation: Impact on Priming of TH1, TH2 and Nonpolarized T Cells." Nat. Immunol. 1.4(2000):311-316.
Langer et al. "Tissue Engineering." Science. 260(1993):920-926.
Lanzavecchia et al. "Regulation of T Cell Immunity by Dendritic Cells." Cell. 106.3(2001):263-266.
Lao et al. "Magnetic and Hydrogel Composite Materials for Hyperthermia Applications." J. Mater. Sci. Mater. Med. 15.10(2004):1061-1064.
Latorre et al. "Applications of magnetic nanoparticles in medicine: magnetic fluid hyperthermia." P R Health Sci J. Sep. 2009;28(3):227-38.
Lauterbach et al. "Mouse CD8α+ DCs and Human BDCA3+DCs are Major Producers of IFN-λ in Response to Poly IC." J. Exp. Med. 207.12(2010):2703-2717.
Leach et al. "Coating of VEGF-Releasing Scaffolds with Bioactive Glass for Angiogenesis and Bone Regeneration." Biomater. 27.17(2006):3249-3255.
Lee et al. "Engineering Liver Tissue Spheroids with Inverted Colloidal Crystal Scaffolds." Biomater. 30.27(2009):4687-4694.
Lee et al. "Hydrogel Formation via Vell Crosslinking." Adv. Mat. 15.21(2003):1828-1832.
Lee et al. "Hydrogels for Tissue Engineering." Chem. Rev. 101.7(2001):1869-1879.
Lee et la. "Intravenous hMSCs Improve Myocardial Infarction in Mice because Cells Embolized in Lung are Activated to Secrete the Anti-Inflammatory Protein TSG-6." Cell Stem Cell. 5.1(2009):54-63.
Lefaucheur et al. "The Cellular Events of Injured Muscle Regeneration Depend on the Nature of the Injury." Neuromusc. Disorders. 5.6(1995):501-509.
Lele et al. "Investigating Complexity of Protein-Protein Interactions in Focal Adhesions." Biochem. Biophys. Res. Commun. 369.3(2008):929-934.
Lensch et al. "Scientific and Clinical Opportunities for Modeling Blood Disorders With Embyronic Stem Cells." Blood. 107.7(2006):2605-2612.
Leor et al. "Cells, Scaffolds, and Molecules for Myocardial Tissue Engineering." Pharmacol. Therapeutics. 105(2005):151-163.
Leshem et al. "Hepatocyte Growth Factor (HGF) Inhibits Skeletal Muscle Cell Differentiation: A Role for the bHLH Protein Twist and the cdk Inhibitor p27." J. Cell. Physiol. 184(2000):101-109.
Letsinger et al. "Phosphoramidate Analogs of Oligonucleotides." J. Org. Chem. 35.11(1970):3800-3803.
Leventhal et al. "Soft Biological Materials and their Impact on Cell Function." Soft Matter. 3(2007):299-306.
Li et al. "A Novel Cyclohexene Derivate, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." Mol. Pharmacol. 69.4(2006):1288-1295.
Li et al. "Effect of Growth Factors and Extracellular Matrix Materials on the Proliferation and Differentiation of Microencapsulated Myoblasts." J. Biomater. Sci. Polym. Ed. 14.6(2003):533-549.
Li et al. "Effects of Three-Dimensional Scaffolds on Cell Organization and Tissue Development." Biotech. Bioprocess Eng. 6.5(2001):311-325.
Li et al. "Purified Hybrid Cells from Dendritic Cell and Tumor Cell Fusions are Superior Activators of Antitumor Immunity." Cancer Immunol. 50.9(2001):456-462.
Li et al. PH sensitive Laponite/Alginate Hybrid Hydrogels: Swelling Behaviour and Relase Mechanism. Soft Matter. Jun. 2, 2011; 7(13):6231-6238.
Li. "TNF-α is a Mitogen is Skeletal Muscle." Am. J. Physiol. Cell Physiol. 285(2003):C370-C376.
Lin et al. "Transdermal Regulation of Vascular Network Bioengineering Using a Photopolymerizable Methacrylated Gelatin Hydrogel." Biomater. 34.28(2013):6785-6796.

Lipton et al. "Developmental Fate of Skeletal Satellite Cells." Science. 205(1979):1292-1294.
Liu et al. "Heterobifunctional Poly(Ethylene Glycol)-Tethered Bone Morphogenetic Protein-2-Stimulated Bone Marrow Mesenchymal Stromal Cell Differentiation and Osteogenesis." Tissue Eng. 13.5(2007):1113-1124.
Liu et al. "Nanostructured Materials Designed for Cell Binding and Transduction." Biomacromolecules. 2.2(2001):362-368.
Liu et al. "On the Viscoelastic Character of Liver Tissue: Experiments and Modelling of the Linear Behaviour." Biorheol. 37.3(2000):191-201.
Liu et al. Immunostimulatory CpG oligodeoxynucleotides enhance the immune response to; vaccine strategies involving granulocyte-macrophage colony-stimulating factor.; Blood. Nov. 15, 1998;92(10):3730-6;.
Liu et al. Selective inhibition of IDO1 effectively regulates mediators of antitumor immunity. Blood. Apr. 29, 2010;115(17):3520-30.
Liu. "Dendritic Cell Subsets and Lineages, and Their Functions in Innate and Adaptive Immunity." Cell. 106.3(2001):259-262.
Lo et al. "Cell Movement is Guided by the Rigidity of the Substrate." Biophys. J. 79.1(2000):144-152.
Lu et al. "Muscle-Derived Stem Cells Seeded Into Acellular Scaffolds Develop Calcium-Dependent Contractile Activity That is Modulated by Nicotinic Receptors." Urology. 61.6(2003):1285-1291.
Lubeck. "The Costs of Musculoskeletal Disease: Health Needs Assessment and Health Economics." Best Pract. Res. Clin. Rheumatol. 17.3(2003):529-539.
Ludewig et al. "Immunotherapy with Dendritic Cells Directed Against Tumor Antigens Shared with Normal Host Cells Results in Severe Autoimmune Disease." J. Exp. Med. 191.5(2000):795-804.
Lumelsky et al. "Differentiation of Embryonic Stem Cells to Insulin-Secreting Structures Similar to Pancreatic Islets." Science. 292.5520(2001):1389-1394.
Lutolf et al. "Repair of Bone Defects Using Synthetic Mimetics of Collagenous Extracellular Matrices." Nat. Biotechnol. 21.5(2003):513-518.
López et al. "Magnetic Applications of Polymer Gels." Macromol. Symp. 166.1(2001):173-178.
Mach et al. "Differences in Dendritic Cells Stimulated in Vivo by Tumors Engineered to Secrete Granulocyte-Macrophage Colony-Stimulating Factor or Flt3-Ligand." Cancer Res. 60.12(2000):3239-3246.
Magram et al. "IL-12-Deficient Mice are Defective but not Devoid of Type 1 Cytokine Responses." Ann. N.Y. Acad. Sci. 795(1996):60-70.
Maini. "Spatial and Spatio-Temporal Patterns in a Cell-Haptotaxis Model." J. Math. Biol. 27.5(1989):507-522.
Majeti et al. "Identification of a Hierarchy of Multipotent Hematopoietic Progenitors in Human Cord Blood." Cell Stem Cell. 1.6(2007):635-645.
Maley et al. "Extracellular Matrix, Growth Factors, Genetics: Their Influence on Cell Proliferation and Myotube Formation in Primary Cultures of Adult Mouse Skeletal Muscle." Exp. Cell Res. 219.1(1995):169-179.
Malhotra et al. "Use of an oncolytic virus secreting GM-CSF as combined oncolytic and immunotherapy for treatment of colorectal and hepatic adenocarcinomas." Surgery. Apr. 2007;141(4):520-9.
Malmqvist. "Biospecific Interaction Analysis Using Biosensor Technology." Nature. 361.6408(1993):186-187.
Mammoto et al. "Mechanical Control of Tissue and Organ Development." Development. 137.9(2010):1407-1420.
Manavski et al. "Vascular Niche Controls Organ Regeneration." Circ. Res. 114.17(2014):1077-1079.
Mansoor et al. "Engineering T Cells for Cancer Therapy." Br. J. Cancer. 93.10(2005):1085-1091.
Martinsen et al. "Alginate as Immobilization Material." Biotech. Bioeng. 33.1(1989):79-89.
Marui et al. "Simultaneous Application of Basic Fibroblast Growth Factor and Hepatocyte Growth Factor to Enhance the Blood Vessels Formation." J. Vasc. Surg. 41.1(2005):82-90.

(56) References Cited

OTHER PUBLICATIONS

Masedunskas et al. "Role for the Actomyosin Complex in Regulated Exocytosis Revealed by Intravital Microscopy." PNAS. 108.33(2011):13552-13557.
Massia et al. "An RGD Spacing of 440 nm is Sufficient for Integrin αvβ3-Mediated Fibroblast Spreading and 140 nm for Focal Contact and Stress Fiber Formation." J. Cell Biol. 114.5(1991):1089-1100.
Matthew et al. "Subperiosteal Behaviour of Alginate and Cellulose Wound Dressing Materials." Biomaterials. 16.4(1995):275-278.
McDonald et al. "Early Fracture Callus Displays a Smooth Muscle-Like Viscoelastic Properties Ex Vivo: Implications for Fracture Healing." J. Orthop. Res. 27.11(2009):1508-1513.
McKinney-Freeman et al. "Muscle-Derived Hematopoietic Stem Cells are Hematopoietic in Origin." PNAS. 99.3(2002):1341-1346.
McKinnon et al. "Biophysically Defined and Cytocompatible Covalently Adaptable Networks as Viscoelastic 3D Cell Culture Systems." Adv. Mater. 26.6(2014):865-872.
McPherron et al. "Regulation of Skeletal Muscle Mass in Mice by a New TGF-β Superfamily Member." Nature. 387(1997):83-90.
McWhorter et al. "Modulation of Macrophage Phenotype by Cell Shape." PNAS. 110.43(2013):17253-17258.
Meier et al. "Peptide Nucleic Acids (PNAs)—Unusual Properties of Noionic Oligonucleotide Analogues." Angew. Chem. Int. Ed. 31.8(1992):1008-1010.
Melero-Martin et al. "Engineering Robust and Functional Vascular Networks In Vivo With Human Adult and Cord Blood-Derived Progenitor Cells." Circ. Res. 103.2(2008):194-202.
Melief et al. "Immunotherapy of Established (Pre)Malignant Disease by Synthetic Long Peptide Vaccines." Nat. Rev. Cancer. 8(2008):351-360.
Mellman et al. "Dendritic Cells: Specialized and Regulated Antigen Processing Machines." Cell. 106.3(2001):255-258.
Menetrey et al. "Suturing Versus Immobilization of a Muscle Laceration: A Morphological and Functional Study in a Mouse Model." Am. J. Sports Med. 27.2(1999):222-229.
Meraz et al. "Mesoporous Silicon Particles for the Presentation of Tumor Antigens and Adjuvant for Anti-Cancer Immunity." Cancer Res. 71.S24(2011):159s-160s. (Abstract #P1-01-12).
Merkel et al. "Using Mechanobiological Mimicry of Red Blood Cells to Extend Circulation Times of Hydrogel Microparticles." PNAS. 108.2(2011):586-591.
Metters et al. "Fundamental Studies of Biodegradable Hydrogels as Cartilage Replacement Materials." Biomed. Sci. Instrum. 35(1999):33-38.
Meyer et al. "Clinical Investigations of Toll-Like Receptor Agonists." Expert Opin. Investig. Drugs. 17.7(2008):1051-1065.
Meylan et al. "Intracellular Pattern Recognition Receptors in the Host Response." Nature. 442.7098(2006):39-44.
Miljkovic et al. "Chondrogenesis, Bone Morphogenetic Protein-4 and Mesenchymal Stem Cells." Osteoarthritis Cartilage. 16(2008):1121-1130.
Miller et al. "Hepatocyte Growth Factor Affects Satellite Cell Activation and Differentiation in Regenerating Skeletal Muscle." Am. J. Physiol. Cell Physiol. 278(2000):C174-C181.
Miller et al. "Lipopolysaccharide Sequestrants: Structural Correlates of Activity and Toxicity in Novel Acylhomospermines." J. Med. Chem. 48(2005):2589-2599.
Miller et al. "Melanoma." N. Engl. J. Med. 355.1(2006):51-65.
Miralles et al. "Actin Dynamics Control SRF Activity by Regulation of its Coactivator MAL." Cell. 113.3(2003):329-342.
Mitchell et al. "The Exogenous Administration of Basic Fibroblast Growth Factor to Regenerating Skeletal Muscle in Mice Does Not Enhance the Process of Regeneration." Growth Factors. 13.1-2(1996):37-55.
Miyata et al. "Biomolecule-Sensitive Hydrogels." Adv. Drug Deliv. Rev. 54.1(2002):79-98.
Mohan et al. "Novel Porous, Polysaccharide Scaffolds for Tissue Engineering Applications." Trends Biomater. Artif. Organs. 18.2(2005):219-224.
Moioli et al. "Matrices and Scaffolds for Drug Delivery in Dental, Oral and Craniofacial Tissue Engineering." Adv. Drug Deliv. Rev. 59.4-5(2007):308-324.
Molinari et al. "Modification of Surface Membrane Antigens by Trypsin." Proc. Soc. Exp. Biol. Med. 148.4(1975):991-994.
Molloy et al. "Movement and Force Produced by a Single Myosin Head." Nature. 378.6553(1995):209-212.
Mooney et al. "Cytoskeletal Filament Assembly and the Control of Cell Spreading and Function by Extracellular Matrix." J. Cell Sci. 108.Pt6(1995):2311-2320.
Mooney et al. "Switching From Differentiation to Growth in Hepatocytes: Control by Extracellular Matrix." J. Cell. Phys. 151.3(1992):497-505.
Moser et al. "Dendritic Cell Regulation of TH1-TH2 Regulation." Nat. Immunol. 1.3(2000):199-205.
Muralidharan-Chari et al. "ARF6-Regulated Shedding of Tumor Cell-Derived Plasma Membrane Microvesicles." Curr. Biol. 19.22(2009):1875-1885.
Murdan. "Electro-Responsive Drug Delivery from Hydrogels." J. Control. Release. 92(2003):1-17.
Nagai et al. "A Variant of Yellow Fluorescent Protein with Fast and Efficient Maturation for Cell-Biological Applications." Nat. Biotechnol. 20.1(2002):87-90.
Naik et al. "Development of Plasmacytoid and Conventional Dendritic Cell Subtypes From Single Precursor Cells Derived in vitro and in vivo." Nat. Immunol. 8.11(2007):1217-1226.
Nair et al. "Polymers as Biomaterials for Tissue Engineering and Controlled Drug Delivery." Adv. Biochem. Eng. Biotechnol. 102(2006):47-90.
NCBI Accession No. NM_000758, Apr. 1, 2012.
NCBI Accession No. NM_001561.5, Mar. 16, 2014.
NCBI Accession No. NM_003265, Dec. 30, 2012.
NCBI Accession No. NM_004119, Apr. 14, 2013.
NCBI Accession No. NM_004448.3, Apr. 23, 2014.
NCBI Accession No. NM_005018.2, Apr. 27, 2014.
NCBI Accession No. NM_006274.2, Mar. 31, 2013.
NCBI Accession No. NM_017442, Apr. 14, 2012.
NCBI Accession No. NM_181780.3, Jan. 27, 2014.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_001193, May 3, 2014.
NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_003367, Jan. 30, 2011.
NCBI Accession No. NP_005009.2, Apr. 27, 2014.
NCBI Accession No. NP_059138, Apr. 14, 2012.
NCBI Accession No. NP_861445.3, Jan. 27, 2014.
Nehls et al. "A Novel, Microcarrier-Based in Vitro Assay for Rapid and Reliable Quantification of Three-Dimensional Cell Migration and Angiogenesis." Microvasc. Res. 50.3(1995):311-322.
Nestle et al. "Vaccination of melanoma patients with peptide- or tumor lysate-pulsed dendritic cells." Nat Med. Mar. 1998;4(3):328-32.
Niamlang et al. "Electrically Controlled Release of Salicylic Acid from poly(p-phenylene vinylene) Polyacrylamide Hydrogels." Int. J. Pharm. 371(2009):126-133.
Nichol et al. "Cell-Laden Microengineered Gelatin Methacrylate Hydrogels." Biomater. 31.21(2010):5536-5544.
Nicodemus et al. "Cell Encapsulation in Biodegradable Hydrogels for Tissue Engineering Applications." Tissue Eng. Part B Rev. 14.2(2008):149-165.
Niessen et al. "The α6β4 Integrin is a Receptor for Both Lamin and Kalinin." Exp. Cell Res. 211.2(1994):360-367.
Noguera-Troise et al. "Blockade of Dll4 Inhibits Tumour Growth by Promoting Non-Productive Angiogenesis." Nature. 444.7122(2006):1032-1037.

(56) References Cited

OTHER PUBLICATIONS

O'Garra et al. "Are Dendritic Cells Afraid of Commitment?" Nat. Immunol. 5.12(2004):1206-1208.
O'Shea et al. "Type 1 IFNs and Regulation of TH1 Responses: Enigmas Both Resolved and Emerge." Nat. Immunol. 1.1(2000):17-19.
Ohashi et al. "Surgical Excision Combined with Autologous Whole Tumor Cell Vaccination is an Effective Therapy for Murine Neuroblastoma." J. Ped. Surg. 41(2006):1361-1368.
Ohlstein et al. "The Stem Cell Niche: Theme and Variations." Curr. Opin. Cell Biol. 16.6(2004):693-699.
Oldenburg et al. "TLR13 Recognizes Bacterial 23S rRNA Devoid of Erythromycin Resistance-Forming Modification." Science. 337. 6098(2012):1111-1115.
Oldenhove et al. "Decrease of Foxp3+ Treg Cell Number And Acquisition of Effector Cell Phenotype During Lethal Infection." Immunity. 31.5(2009):772-786.
Orner et al. "Arrays for the Combinatorial Exploration of Cell Adhesion." J. Am. Chem. Soc. 126.35(2004):10808-10809.
Osunkoya et al. "Synthesis and Fate of Immunological Surface Receptors on Cultured Burkitt Lymphoma Cells." Int. J. Cancer. 4.2(1969):159-165.
Ota et al. "Percutaneous Subxiphoid Access to the Epicardium Using a Miniature Crawling Robotic Device." Innovations. 1.5(2006):227-231.
Overwijk et al. "Tumor Regression and Autoimmunity After Reversal of a Functionally Tolerant State of Self-Reactive CD8+ T Cells." J. Exp. Med. 198.4(2003):569-580.
Ozawa et al. "Microenvironmental VEGF Concentration, Not Total Dose, Determines a Threshold Between Normal and Aberrant Angiogenesis." J. Clin. Invest. 113.4(2004):516-527.
Padilla et al. "Insufficient TLR Activation Contributes to the Slow Development of CD8+ T Cell Responses in Trypanosoma cruzi Infection." J. Immunol. 183(2009):1245-1252.
Page-McCaw et al. "Matrix Metalloproteinases and the Regulation of Tissue Remodelling." Nat. Rev. Mol. Cell Biol. 8.3(2007):221-233.
Pailler-Mattei et al. "In vivo Measurements of the Elastic Mechanical Properties of Human Skin by Indentation Tests." Med. Eng. Phys. 30.5(2008):599-606.
Palacio et al. "Interleukin 10 and Tumor Necrosis Factor α Gene Expression in Respiratory and Peripheral Muscles." Arch. Bronconeumol. 38.7(2002):311-316. (Spanish Original and English Abstract).
Paradee et al. "Effects of Crosslinking Ratio, Model Drugs, and Electric Field Strength on Electrically Controlled Release for Alginate-Based Hydrogels." J. Mater. Sci. Mater. Med. 23(2012):999-1010.
Pardoll. "The Blockade of Immune Checkpoints in Cancer Immunotherapy." Nat. Rev. Cancer. 12.4(2012):252-264.
Parekh et al. "Modulus-Driven Differentiation of Marrow Stromal Cells in 3D Scaffolds that is Independent of Myosin-Based Cytoskeletal Tension." Biomater. 32.9(2011):2256-2264.
Parekkadan et al. "Mesenchymal Stem Cell-Derived Molecules Reverse Fulminant Hepatic Failure." PLoS One. 2.9(2007):e941.
Park et al. "Photopolymerized Hyaluronic Acid-Based Hydrogels and Interpenetrating Networks." Biomater. 24.6(2003):893-900.
Parker et al. "Effect of Mitoxantrone on Outcome of Children with First Relapse of Acute Lymphoblastic Leukemia (ALL R3): An Open-Label Radomised Trial." Lancet. 376(2010):2009-2017.
Partridge et al. "Conversion of mdx Myofibres from Dystrophin-Negative to-Positive by Injection of Normal Myoblasts." Nature. 337(1989):176-179.
Pawlaczyk et al. "Age-Dependent Biomechanical Properties of the Skin." Postepy. Dermatol. Alergol. 30.5(2013):302-306.
Pedersen et al. "Induction of Regulatory Dendritic Cells by Desamethasone and 1α,25-Dihydroxyvitamin D3." Immunol. Lett. 91(2004):63-69.
Pek et al. "The Effect of Matrix Stiffness on Mesenchymal Stem Cell Differentiation in a 3D Thixotropic Gel." Biomater. 31.3(2010):385-391.

Pelinkovic et al. "Tissue Engineering and Gene Therapy of the Muscoskeletal System with Muscle Cells." Z. Orthop. Ihre Grenzgeb. 138.5(2000):402-406. (German Original and English Abstract).
Pena et al. "Effects of TGF-β and TGF-β Neutralizing Antibodies on Fibroblast-Induced Collagen Gel Contraction: Implications for Proliferative Vitroretinpathy." Invest. Ophthalmol. Vis. Sci. 35.6(1994):2804-2808.
Peters et al. "Engineering Vascular Networks in Porous Polymer Matrices." J. Biomed. Mater. Res. 60.4(2002):668-678.
Peyton et al. "The Use of Poly(ethylene glycol) Hydrogels to Investigate the Impact of ECM Chemistry and Mechanics on Smooth Muscle Cells." Biomater. 27.28(2006):4881-4893.
Phillippi. "Patterning of Multiple Cell Lineages from a Single Stem Cell Population." Annual Meeting of the American Society for Cell Biology. (Dec. 10, 2006).
Pinho et al. "PDGFRα and CD51 Mark Human Nestin+ Sphere-Forming Mesenchymal Stem Cells Capable of Hematopoietic Progenitor Cell Expansion." J. Exp. Med. 210.7(2013):1351-1367.
Platten et al. Cancer Immunotherapy by Targeting IDO1/TDO and Their Downstream Effectors. Front Immunol. Jan. 12, 2015;5:673.
Pluen et al. "Role of Tumor-Host Interactions in Interstitial Diffusion of Macromolecules: Cranial vs. Subcutaneous Tumors." PNAS. 98.8(2001):4628-4633.
Pooyan et al. "Conjugates Beating Multiple Formyl-Methionyl Peptides Display Enhanced Binding to, but not Activation of Phagocytic Cells." Bioconjugate Chem. 13.2(2002):216-223.
Pope et al. "Organ-Specific Regulation of the CD8 T Cell Response to Listeria monocytogenes Infection." J. Immunol. 166(2001):3402-3409.
Porter et al. "Separation of Natural Populations of Coliform Bacteria from Freshwater and Sewage by Magnetic-Bead Cell Sorting." J. Microbiol. Meth. 33.3(1998):221-226.
Pouzet et al. "Factors Affecting Functional Outcome After Autologous Skeletal Myoblast Transplantation." Ann. Thorac. Surg. 71(2001):844-851.
Pulendran et al. "Flt3-Ligand and Granulocyte Colony-Stimulating Factor Mobilize Distinct Human Dendritic Cell Subsets In Vivo." J. Immunol. 165(2000):566-572.
Qi et al. "Patterned Differentiation of Individual Embryoid Bodies in Spatially Organized 3D Hybrid Microgels." Adv. Mater. 22.46(2010):5276-5281.
Qin et al. "Soft Lithography for Micro- and Nanoscale Patterning." Nat. Protoc. 5.3(2010):491-502.
Qu et al. "Development of Approaches to Improve Cell Survival in Myoblast Transfer Therapy." J. Cell Biol. 142.5(1998):1257-1267.
Qu-Petersen et al. "Identification of a Novel Population of Muscle Stem Cells in Mice: Potential for Muscle Regeneration." J. Cell Biol. 157.5(2002):851-864.
Quezada et al. "CTLA4 Blockade and GM-CSF Combination Immunotherapy Alters the Intratumor Balance of Effector and Regulatory T Cells." J. Clin. Invest. 116.7(2006):1935-1945.
Qui et al. "Environment-Sensitive Hydrogels for Drug Delivery." Adv. Drug Deliv. Rev. 53.3(2001):321-339.
Raeber et al. "Molecularly Engineered PEG Hydrogels: A Novel Model System for Proteolyrically Mediated Cell Migration." Biophys. J. 89.2(2005):1374-1388.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." Circulation. 108.16(2003):1933-1938.
Ramón-Azcón et al. "Gelatin Methacrylate as a Promising Hydrogel for 3D Microscale Organization and Proliferation of Dielectroretically Patterned Cells." Lab on a Chip. 12.16(2012):2959-2969.
Randolph et al. "Migration of Dendritic Cell Subsets and Their Precursors." Annu. Rev. Immunol. 26(2008):293-316.
Ranganath et al. "Harnessing the Mesenchymal Stem Cell Secretome for the Treatment of Cardiovascular Disease." Cell Stem Cell. 10.3(2012):244-258.
Raposo et al. "Extracellular Vesicles: Exosomes, Microvesicles, and Friends." J. Cell. Biol. 200.4(2013):373-383.
Rappolee et al. "Macrophage-Derived Growth Factors." Curr. Top. Microbiol. Immunol. 181(1992):87-140.

(56) References Cited

OTHER PUBLICATIONS

Rapraeger. "Syndecan-Regulated Receptor Signaling." J. Cell. Biol. 149.5(2000):995-998.
Reddy et al. "Exploiting Lymphatic Transport and Complement Activation in Nanoparticle Vaccines." Nat. Biotechnol. 25.10(2007):1159-1164.
Reimann et al. "Satellite Cells in Normal and Regenerated Soleus Muscles of mdx and Control Mice." Eur. J. Neurosci.10(1998):366. (Abstract #153.07).
Reis e Sousa. "Activation of Dendritic Cells: Translating Innate into Adaptive Immunity." Curr. Opin. Immunol. 16.1(3005):21-25.
Rhoads et al. "Satellite Cell-Mediated Angiogenesis in vitro Coincides with a Functional Hypoxia-Inducible Factor Pathway." Am. J. Physiol. Cell Physiol. 296.6(2009):C1321-C1328.
Richards Grayson et al. "Multi-Pulse Drug Delivery From a Resorbable Polymeric Microchip Device." Nat. Mater. 2.11(2003):767-772.
Richardson et al. "Polymeric System for Dual Growth Factor Delivery." Nat. Biotech. 19.11(2001):1029-1034.
Riddle et al. "Role of Poly(lactide-co-glycolide) Particle Size on Gas-Foamed Scaffolds." J. Biomater. Sci. Polym. Ed. 15.12(2004):1561-1570.
Ridgway et al. "Inhibition of Dll4 Signalling Inhibits Tumour Growth by Deregulating Angiogenesis." Nature. 444.7122(2006):1083-1087.
Rinderknecht et al. "The Amino Acid Sequence of Human Insulin-Like Growth Factor I and its Structural Homology with Proinsulin." J. Biol. Chem. 253.8(1978):2769-2776.
Rizzo et al. "An Improved Cyan Fluorescent Protein Variant Useful for FRET." Nat. Biotechnol. 22.4(2004):445-449.
Roccaro et al. "BM Mesenchymal Stromal Cell-Derived Exosomes Facilitate Multiple Myeloma Progression." J. Clin. Invest. 123. 4(2013):1542-1555.
Rodriguez et al. "Minimal "Self" Peptides that Inhibit Phagocytic Clearance and Enhance Delivery of Nanoparticles." Science. 339. 6122(2013):971-975.
Rosenberg et al. "Cancer Immunotherapy: Moving Beyond Current Vaccines." Nat. Med. 10.9(2004):909-915.
Roth et al. "SC68896, a Novel Small Molecule Proteasome Inhibitor, Exerts Antiglioma Activity In vitro and In vivo." Clin. Cancer Res.15.21(2009):6609-6618.
Rowlands et al. "Directing Osteogenic and Myogenic Differentiation of MSCs: Interplay of Stiffness and Adhesive Ligand Presentation." Am. J. Physiol Cell Physiol. 295(2008):1037-1044.
Rowley et al. "Alginate Type and RGD Density Control Myoblast Phenotype." J. Biomed. Mater. Res. 60.2(2002):217-233.
Rowley et al. "Biomaterials to Spatially Regulate Cell Fate." Adv. Mater. 14.12(2002):886-889.
Rowley. "Alginate Hydogels as Synthetic Extracellular Matrix Materials." Biomaterials. 20.1(1999):45-53.
Rubin et al. "Dissociation of Heparan Sulfate and Receptor Binding Domains of Hepatocyte Growth Factor Reveals That Heparan Sulfate-c-Met Interaction Factilitates Signaling." J. Biol. Chem. 276.35(2001):32977-32983.
Ryten et al. "ATP Regulates the Differentiation of Mammalian Skeletal Muscle by Activation of a P2X5 Receptor on Satellite Cells." J. Cell. Biol. 158.2(2002):345-355.
Ryu et al. "The Construction of Three-Dimensional Micro-Fluidic Scaffolds of Biodegradable Polymers by Solvent Vapor Based Bonding of Micro-Molded Layers." Biomaterials. 28.6(2007):1174-1184.
Sacchetti et al. "Self-Renewing Osteoprogenitors in Bone Marrow Sinusoids can Organize a Hematopoietic Microenvironment." Cell. 131.2(2007):324-336.
Sakai et al. "An Injectable, in situ Enzymatically Gellable, Gelatin Derivative for Drug Delivery and Tissue Engineering." Biomater. 30.20(2009):3371-3377.
Salem et al. "Defining the Antigen-Specific T-Cell Response to Vaccination and Poly(I:C)/TLR3 Signaling." J. Immunother. 28.3(2005):220-228.

Salvador et al. "Combination of Immune Stimulating Adjuvants With Poly(lactide-co-glycolide) Microspheres Enhances the Immune Response of Vaccines." Vaccine. 30.3(2011):589-596.
Salvay et al. "Inductive Tissue Engineering with Protein and DNA-Releasing Scaffolds." Mol. Biosyst. 2.1(2006):36-48.
Sano et al. "Swift Development of Protective Effector Functions in Naive CD8+ T Cells Against Malaria Liver Stages." J. Exp. Med. 194.2(2001):173-179.
Sansonetti. "The Innate Signaling of Dangers and the Dangers of Innate Signaling." Nat. Immunol. 7.12(2006):1237-1242.
Sarkar et al. "Condensation of Oligonucleotides Assembled into Nicked and Gapped Duplexes: Potential Structures for Oligonucleotide Delivery." Nucleic Acids Res. 33.1(2005):143-151.
Sato, "Human dendritic cells." Biotherapy. Nov. 2004;18(6):467-77.
Saxena et al. "Skeletal Muscle Tissue Engineering Using Isolated Myoblasts on Synthetic Biodegradable Polymers: Preliminary Studies." Tissue Eng. 5.6(1999):525-532.
Schaefer et al. "Innate Immunity in the Human Female Reproductive Tract: Antiviral Response of Uterine Epithelial Cells to TLR3 Agonist Poly (I:C)." J. Immunol. 174(2005):992-1002.
Scheel et al. "Toll-Like Receptor-Dependent Activation of Several Human Blood Cell Types by Protamine Condensed mRNA." Eur. J. Immunol. 35(2005):1557-1566.
Schijns et al. "Mice Lacking IL-12 Develop Polarized Th1 Cells During Viral Infection." J. Immunol. 160(1998):3958-3964.
Schnorrer et al. "The Dominant Role of CD8+ Dendritic Cells in Cross-Presentation is not Dictated by Antigen Capture." PNAS. 103.28(2006):10729-10734.
Schofield. "The Relationship Between the Spleen Colony-Forming Cell and the Haemopoietic Stem Cell." Blood. Cells. 4.1-2(1978):7-25.
Schuler et al. "The Use of Dendritic Cells in Cancer Immunotherapy." Curr. Opin. Immunol. 15.2(2003):138-147.
Schwartz. "Integrins and Extracellular Matrix in Mechanotransduction." Cold Spring Harb. Perspect. Biol. 2.12(2010):a005066.
Seale et al. "Pax7 Is Required for the Specification of Myogenic Satellite Cells." Cell. 102.6(2000):777-786.
Sensi et al. "Unique Tumor Antigens: Evidence for Immune Control of Genome Integrity and Immunogenic Targets for T Cell-Mediated Patient-Specific Immunotherapy." Clin. Cancer Res. 12.17(2006):5023-5032.
Shakweh et al. "Design and Characterisation of Poly(lactide-co-glycolide) Small Particulate Systems for the Delivery of Immunostimulant CpG Oligonucleotide." J. Nanosci. Nanotechnol. 6.9-10(2006):2811-2820.
Shaner et al. "Improved Monomeric Red, Orange and Yellow Fluorescent Proteins Derived from Discosoma sp. Red Fluorescent Protein." Nat. Biotechnol. 22.12(2004):1567-1572.
Shansky et al. "Letter to the Editor: A Simplified Method for Tissue Engineering Skeletal Muscle Organoids In Vitro." In Vitro Cell. Dev. Biol. 33(1997):659-661.
Sheehan et al. "Skeletal Muscle Satellite Cell Proliferation in Response to Members of the Fibroblast Growth Factor Family and Hepatocyte Growth Factor." J. Cell. Physiol. 181.3(1999):499-506.
Sheridan et al. "Bioabsorbable Polymer Scaffolds for Tissue Engineering Capable of Sustained Growth Factor Delivery." J. Control. Release. 64.1-3(2000):91-102.
Shi et al. "A Novel Toll-Like Receptor that Recognizes Vascular Stomatitis Virus." J. Biol. Chem. 286.6(2011):4517-4524.
Shi et al. "Granulocyte-Macrophage Colony-Stimulating Factor (GM-CSF) and T-Cell Responses: What we do and don't know." Cell Res. 16.2(2006):126-133.
Shin et al. "Contractile Forces Sustain and Polarize Hematopoiesis from Stem and Progenitor Cells." Cell Stem Cell. 14.1(2014):81-93.
Shin et al. "Lamins Regulate Cell Trafficking and Lineage Maturation of Adult Human Hematopoetic Cells." PNAS. 110. 47(2013):18892-18897.
Shin et al. "Myonsin-II Inhibition and Soft 2D Matrix Maximize Multinucleation and Cellular Projections Typical of Platelet-Producing Megakaryocytes." PNAS. 108.28(2011):11458-11463.

(56) References Cited

OTHER PUBLICATIONS

Shoichet et al. "Stability of Hydrogels Used in Cell Encapsulation: An In Vitro Comparison of Alginate and Agarose." Biotechnol. Bioeng. 50(1996):374-381.
Shortman et al. "Steady-State and Inflammatory Dendritic-Cell Development." Nat. Rev. Immunol. 7(2007):19-30.
Sick et al. "WNT and DKK Determine Hair Follicle Spacing Through a Reaction-Diffusion Mechanism." Science. 314.5804(2006):1447-1450.
Siegwart et al. "Synthesis, Characterization, and in vitro Cell Culture Viability of Degradable Poly(N-isopropylacrylamide-co-5,6-benzo-2-methylene-1,3-dioxepane)-Based Polymers and Cross-linked Gels." J. Biomed. Mater. Res. A. 87.2(2008):345-358.
Silva et al. "Effects of VEGF Temporal and Spatial Presentation on Angiogenesis." Biomaterials. 31.6(2010):1235-1241.
Silva et al. "Material-Based Deployment Enhances Efficacy of Endothelial Progenitor Cells." PNAS. 105.38(2008):14347-14352.
Silva et al. "Spatiotemporal Control of Vascular Endothelial Growth Factor Delivery From Injectable Hydrogels Enhances Angiogenesis." J. Thromb. Haemost. 5.3(2007):590-598.
Singer et al. "Cutaneous Wound Healing." N. Engl. J. Med. 341.10(1999):738-746.
Skokos et al. "CD8–DCs Induce IL-12-Independent Th1 Differentiation Through Delta 4 Notch-Like Ligand in Response to Bacterial LPS." J. Exp. Med. 204.7(2007):1525-1531.
Skuk et al. "Efficacy of Myoblast Transplantation in Nonhuman Primates Following Simple Intramuscular Cell Injections: Toward Defining Strategies Applicable to Humans." Exp. Neurol. 175.1(2002):112-126.
Skuk et al. "Myoblast Transplantation: The Current Status of a Potential Therapeutic Tool for Myopathies." J. Musc. Res. Cell. Motil. 24.4-6(2003):285-300.
Smidsrød et al. "Alginate as Immobilization Matrix for Cells." Trends Biotechnol. 8.3(1990):71-78.
Sohier et al. "Critical Factors in the Design of Growth Factor Releasing Scaffolds for Cartilage Tissue Engineering." Exp. Opin. Drug Deliv. 5.5(2008):543-566.
Solon et al. "Fibroblast Adaptation and Stiffness Matching to Soft Elastic Substrates." Biophys. J. 93.12(2007):4453-4461.
Stachowiak et al. "Inverse Opal Hydrogel-Collagen Composite Scaffolds as a Supportive Microenvironment for Immune Cell Migration." J. Biomed. Mater. Res. 85A(2008):815-828.
Steinman et al. "Taking Dendritic Cells into Medicine." Nature. 449.7161(2007):419-426.
Storrie et al. "Sustained Delivery of Plasmid DNA From Polymeric Scaffolds for Tissue Engineering." Adv. Drug Deliv. Rev. 58.4(2006):500-514.
Straub et al. "Animal Models for Muscular Dystrophy Show Different Patterns of Sarcolemmal Distruption." J. Cell Biol. 139.2(1997):375-385.
Sun et al. "Biomimetic Interpenetrating Polymer Network Hydrogels Based on Methacrylated Alginate and Collagen for 3D Pre-Osteoblast Spreading and Osteogenic Differentiation." Soft Matter. 8(2012):2398-2404.
Sun et al. "Highly Stretchable and Tough Hydrogels." Nature. 489.7414(2012):133-136.
Sun et al. "Sustained Vascular Endothelial Growth Factor Delivery Enhances Angiogenesis and Perfusion in Ischemic Hind Limb." Pharm. Res. 22.7(2005):1110-1116.
Suri et al. "Photopatterned Collagen-Hyaluronic Acid Interpenetrating Polymer Network Hydrogels." Acta Biomater. 5.7(2009):2385-2397.
Suzuki et al. A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.
Swift et al. "Nuclear Lamin-A Scales with Tissue Stiffness and Enhances Matrix-Directed Differentiation." Science. 341.6149(2013):1240104.
Syed et al. "Stem Cell Therapy Market." Nat. Rev. Drug Discov. 12.3(2013):185-186.
Tabata et al. "Enhanced Vascularization and Tissue Granulation by Basic Fibroblast Growth Factor Impregnated in Gelatin Hydrogels." J. Control. Release. 31.2(1994):189-199.
Takahashi et al. "Induction of Pluripotent Stem Cells from Adult Human Fibroblasts by Defined Factors." Cell. 131.5(2007):861-872.
Takeshita et al. "Therapeutic Angiogenesis." J. Clin. Invest. 93.2(1994):662-670.
Tamura et al. "Immunotherapy of Tumors with Autologous Tumor-Derived Heat Shock Protein Preparations." Science. 278.3(1997):117-120.
Tanaka et al. "Collapse of Gels in an Electric Field." Science. 218(1982):467-469.
Tang et al. Combining radiation and immunotherapy: a new systemic therapy for solid tumors? Cancer Immunol Res. Sep. 2014;2(9):831-8.
Tannous. "Gaussia Luciferase Reporter Assay for Monitoring Biological Processes in Culture and in vivo." Nat. Protoc. 4.4(2009):582-591.
Tatsumi et al. "HGF/SF Is Present in Normal Adult Skeletal Muscle and Is Capable of Activating Satellite Cells." Dev. Biol. 194.1(1998):114-128.
ten Dijke et al. "Growth Factors for Wound Healing." Nat. Biotechnol. 7(1989):793-798.
Thomas et al. "Intravenous Infusion of Bone Marrow in Patients Receiving Radiation and Chemotherapy." N. Engl. J. Med. 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." J. Exp. Med. 190.11(1999):1669-1678.
Thurston et al. "The Delta Paradox: DLL4 Blockade Leads to More Tumour Vessels but Less Tumour Growth." Nat. Rev. Cancer. 8.5(2007):327-331.
Tidball. "Inflammatory Cell Response to Acute Muscle Injury." Med. Sci. Sports Exerc. 27.7(1995):1022-1032.
Tomer et al. "Electrically Controlled Release of Macromolecules from Cross-Linked Hyaluronic Acid Hydrogels." J. Control. Release. 33.3(1995):405-413.
Tong et al. "Engineering Interpenetrating Network Hydrogels as Biomimetic Cell Niche with Independently Tunable Biochemical and Mechanical Properties." Biomater. 35.6(2014):1807-1815.
Tourniaire et al. "Polymer Microarrays for Cellular Adhesion." Chem. Commun. (Camb). 20(2006):2118-2120.
Trappmann et al. "Extracelluar-Matrix Tethering Regulates Stem-Cell Fate." Nat. Mater. 11.7(2012):642-649.
Trappmann et al. "How Cells Sense Extracellular Matrix Stiffness: A Material's Perspective." Curr. Opin. Biotechnol. 24.5(2013):948-953.
Tsien. "The Green Fluorescent Protein." Annu. Rev. Biochem. 67(1998):509-544.
Turing. "Discussion: Turing's Theory of Morphogenesis—It's Influence on Modelling Biological Pattern and Form." Bull. Math. Biol. 52.1-2(1990):119-159.
Turing. "The Chemical Basis of Morphogenesis." Philosophical Transactions of the Royal Society of London. Series B. 237.641(1952):37-72.
Uchida et al. "Immunization by Particle Bombardment of Antigen-Loaded poly-(DL-lactide-co-glycolide) Microspheres in Mice." Vaccine. 12(2006):2120-2130.
Ugarte et al. "Notch Signaling Enhances Osteogenic Differentiation While Inhibiting Adipogenesis in Primary Human Bone Marrow Stromal Cells." Exp. Hematol. 37(2009):867-875.
Uhlenbruck. "Action of Proteolytic Enzymes on the Human Erythrocyte Surface." Nature. 190(1961):181.
Ulrich et al. "Probing Cellular Mechanobiology in Three-Dimensional Culture with Collagen-Agarose Matrices." Biomater. 31.7(2010):1875-1884.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.

(56) References Cited

OTHER PUBLICATIONS

UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al. "Stem Cell Niches in the Adult Mouse Heart." PNAS. 103.24(2006):9226-9231.
van der Bruggen et al. "T Cell-Defined Tumor Antigens." Cancer Immunity. (2013). Http:www.cancerimmunity.org/peptide.
van Duin et al. "Triggering TLR Signaling in Vaccination." Trends Immunol. 27.1(2006):49-55.
Vandenburgh et al. "Tissue-Engineered Skeletal Muscle Organoids for Reversible Gene Therapy." Hum. Gene Ther. 17(1996):2195-2200.
Venturoni et al. "Investigations into the Polymorphism of Rat Tail Tendon Fibrils Using Atomic Force Microscopy." Biochem. Biophys. Res. Commun. 303.2(2003):508-513.
Vieira et al. "The Bulk of Endogenously Produced IgG2a is Eliminated From the Serum of Adult C57BL/6 Mice With a Half-Life of 6-8 Days." Eur. J. Immunol. 16.7(1986):871-874.
Vieira et al. "The Half-Lives of Serum Immunoglobulins in Adult Mice." Eur. J. Immunol. 18.2(1988):313-316.
Villadangos et al. "Intrinsic and Cooperative Antigen-Presenting Functions of Dendritic-Cell Subsets in vivo." Nat. Rev. Immunol. 7.7(2007):543-555.
Villadangos. "Presentation of Antigens by MHC Class II Molecules: Getting the Most Out of Them." Molec. Immunol. 38.5(2001):329-346.
Vincent et al. "Stem Cell Differentiation: Post-Degradation Forces Kick in." Nat. Mater. 12.5(2013):384-386.
Vogel et al. "Local Force and Geometry Sensing Regulate Cell Functions." Nat. Rev. Mol. Cell Biol. 7.4(2006):265-275.
von Dassow et al. "The Segment Polarity Network is a Robust Developmental Module." Nature. 406.6792(2000):188-192.
Wakim et al. "Dendritic Cell-Induced Memory T Cell Activation in Nonlymphoid Tissues." Science. 319(2008):198-202.
Waldron-Lynch et al. "Advances in Type 1 Diabetes Therapeutics: Immunomodulation and β-Cell Savage." Endocrinol. Metab. Clin. North Am. 38.2(2009):303-317.
Wan et al. "Peritoneal Macrophage Uptake, Pharmacokinetics and Biodistribution of Macrophage-Targeted PEG-fMLF (N-Formyl-Methionyl-Leucyl-Phenylalanine) Nanocarriers for Improving HIV Drug Delivery." Pharm. Res. 24.11(2007):2110-2119.
Wang et al. "Biological Activity of Bevacizumab, a Humanized Anti-VEGF Antibody in vitro." Angiogenesis. 7.4(2004):335-345.
Wang et al. "Evolution of New Nonantibody Proteins via Iterative Somatic Hypermutation." PNAS. 101.48(2004):16745-16749.
Wang et al. "Mechanotransduction at a Distance: Mechanically Coupling the Extracellular Matric with the Nucleus." Nat. Rev. Mol. Cell. Biol. 10.1(2009):75-82.
Wang et al. "Photothermal effects of supramolecularly assembled gold nanoparticles for the; targeted treatment of cancer cells." Angew Chem Int Ed Engl. May 17, 2010;49(22):3777-81.;.

Wang-Gillam et al. "A Phase I Study of IMP321 and Gemcitabine as the Front-Line Therapy in Patients with Advanced Pancreatic Adenocarcinoma." Invest. New Drugs. 31.3(2013):707-713.
Warner et al. "Cyclooxygenases: New Forms, New Inhibitors, and Lessons from the Clinic." FASEB J. 18.7(2004):790-804.
Wei et al. "Global Mapping of H3K4me3 and H3K27me3 Reveals Specificity in Plasticity in Lineage Fate Determination of Differentiating CD4+ T Cells." Immunity. 30.1(2009):155-167.
Weisenberger et al. "Comprehensive DNA Methylation Analysis on the Illumina® Infinium® Assay Platform." Illumina, Inc. Mar. 25, 2008. Web.
Weiss et al. "The Demonstration of Rupture of Cell Surfaces by an Immunological Technique." Exp. Cell Res. 30(1963):331-338.
Wen et al. "Mechanically Robust Gelatin-Alginate IPN Hydrogels by a Combination of Enzymatic and Ionic Crosslinking Approaches." Macromol. Mater. Eng. 299(2013):504-513.
Wernig et al. "Function of Skeletal Muscle Tissue Formed After Myoblast Transplantation into Irradiated Mouse Muscles." J. Physiol. 522.2(2000):333-345.
White et al. "Leukemia Inhibitory Factor Enhances Regeneration in Skeletal Muscles After Myoblast Transplantation." Musc. Nerve. 24.5(2001):695-697.
Wieland et al. "Engineering Molecular Circuits Using Synthetic Biology in Mammalian Cells." Annu. Rev. Chem. Biomol. Eng. 3(2012):209-234.
Wipff et al. "Myofibroblast Contraction Activates Latent TGF-β1 from the Extracellular Matrix." J. Cell Biol. 179.6(2007):1311-1323.
Wong et al. "Focal Adhesion Kinase Links Mechanical Force to Skin Fibrosis via Inflammatory Signaling." Nat. Med. 18.1(2011):148-152.
Wong et al. "Mechanical Force Prolongs Acute Inflammation via T-Cell-Dependent Pathways During Scar Formation." FASEB. J. 25.12(2011):4498-4510.
Wong et al. "Pushing Back: Wound Mechanotransduction in Repair and Regeneration." J. Invest. Dermatol. 131.11(2011):2186-2196.
World Health Organization. "Global Burden of Musculoskeletal Disease Revealed in new WHO Report." Bull. World Health Organ. 81.11(2003):853-854.
World Health Organization. "The World Health Report 2004: Changing History." (2004):1-169.
Wozniak et al. "Mechanotransduction in Development: A Growing Role for Contractility." Nat. Rev. Mol. Cell Biol. 10.1(2009):34-43.
Wright et al. "Muscle-Based Gene Therapy and Tissue Engineering for the Musculoskeletal System." Drug Disc. Today. 6.14(2001):728-733.
Xie et al. "Preparation and Application of Surface-Coated Superparamagnetic Nanobeads in the Isolation of Genomic DNA." J. Magn. Magnetic Mater. 277.1(2004):16-23.
Xiong et al. Transcription Factor STAT3 as a Novel Molecular Target for Cancer Prevention. Cancers (Basel). Apr. 16, 2014;6(2):926-57.
Yamazaki et al., J. Immunology. 181:6923-6933 (2008).
Yancopoulos et al. "Vascular-Specific Growth Factors and Blood Vessel Formation." Nature. 407.6801(2000):242-248.
Yang et al., "The effect of incorporating RGD adhesive peptide in polyethylene glycol diacrylate hydrogel on osteogenesis of bone marrow stromal cells." Biomaterials. 26(2005):5991-5998.
Yeung et al. "Effects of Substrate Stiffness on Cell Morphology, Cytoskeletal Structure, and Adhesion." Cell Motil. Cytoskeleton. 60.1(2005):24-34.
Yoo et al. "Bio-Inspired, Bioengineered and Biomimetic Drug Delivery Carriers." Nat. Rev. Drug Discov. 10.7(2011):521-535.
Yoon. "Hidden Markov Models and their Applications in Biological Sequene Analysis." Curr. Genomics. 10.6(2009):402-415.
Young et al. "Gelatin as a Delivery Vehicle for the Controlled Release of Bioactive Molecules." J. Control. Release. 109.1-3(2005):256-274.
Yu et al. "Induced Pluripotent Stem Cell Lines Derived from Human Somatic Cells." Science. 318.5858(2007):1917-1920.
Yuen et al. "Mimicking Nature by Codelivery of Stimulant and Inhibitor to Create Temporally Stable and Spatially Restricted Angiogenic Zones." PNAS. 107.42(2010):17933-17938.

(56) References Cited

OTHER PUBLICATIONS

Yuk et al. "Electric Current-Sensitive Drug Delivery System Using Sodium Alginate/Polyacrylic Acid Composites." Pharm. Res. 9.7(1992):955-957.
Zammit et al. "Kinetics of Myoblast Proliferation Show That Resident Satellite Cells are Competent to Fully Regenerate Skeletal Muscle Fibers." Exp. Cell Res. 281.1(2002):39-49.
Zammit et al. "Muscle Satellite Cells Adopt Divergent Fates: A Mechanism for Self-Renewal?" J. Cell Biol. 166.3(2004):347-357.
Zeltinger et al. "Effect of Pore Size and Void Fraction on Cellular Adhesion, Proliferation, and Matrix Deposition." Tissue Eng. 7.5(2001):557-572.
Zemel et al. "Optimal Matrix Rigidity for Stress Fibre Polarization in Stem Cells." Nat. Phys. 6.6(2010):468-473.
Zhang et al. "A Comparative Study of the Antigen-Specific Immune Response Induced by Co-Delivery of CpG OGN and Antigen Using Fusion Molecules or Biodegradable Microparticles." J. Pharma. Sci. 98.12(2007):3283-3292.
Zhang et al. "A Tension-Induced Mechanostransduction Pathway Promotes Epithelial Morphogenesis." Nature. 471.7336(2011):99-103.
Zhang et al. "Talin Depletion Reveals Independence of Initial Cell Spreading from Integrin Activation and Traction." Nat. Cell Biol. 10.9(2008):1062-1068.
Zhao et al. "Active Scaffolds for On-Demand Drug and Cell Delivery." PNAS. 108.1(2011):67-72.
Zhao et al. "Directed Cell Migration via Chemoattractants Released from Degradable Microspheres." Biomat. 26(2005):5048-5063.
Zhao et al. "Stress-Relaxation Behavior in Gels with Ionic and Covalent Crosslinks." J. Appl. Phys. 107.6(2010):63509.
Zhao et al. A cell-permeable Stat3 SH2 domain mimetic inhibits Stat3 activation and induces antitumor cell effects in vitro. J Biol Chem. Nov. 12, 2010;285(46):35855-65.
Zhou et al. "Microstructure and Mechanical Properties of Poly(L-lactide) Scaffolds Fabricated by Gelatin Particle Leaching Method." J. Appl. Polymer Sci. 98(2005):1373-1379.

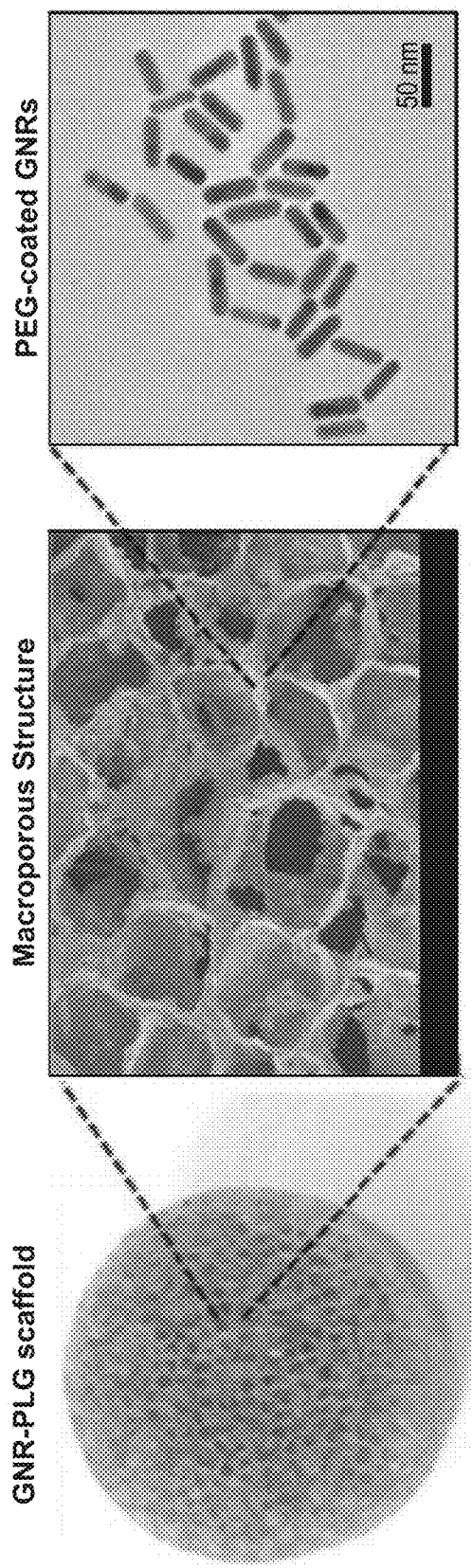

IN SITU ANTIGEN-GENERATING CANCER VACCINE

RELATED APPLICATIONS

This application is a continuation of U.S. Ser. No. 14/123,615, which is a national stage application, filed under 35 U.S.C. § 371, of PCT International Application No. PCT/US2012/040687, filed Jun. 4, 2012, which claims the benefit of priority to U.S. Provisional Application No. 61/493,398, filed Jun. 3, 2011, the contents of each of which are incorporated herein by reference in their entireties.

FIELD OF THE INVENTION

The invention relates generally to the field of cancer vaccines.

BACKGROUND OF THE INVENTION

Cancer accounts for approximately 13% of all human deaths worldwide each year. Existing dendritic cell-based therapeutic strategies are largely based on ex vivo manipulation of dendritic cells to generate large numbers of cells for activation with cancer antigen isolated from a biopsy of a patient's tumor. Because these ex vivo techniques are invasive and expensive, there is a pressing need to develop dendritic cell-based cancer vaccine strategies that are not dependent on surgical biopsies and ex vivo manipulation of cells.

SUMMARY OF THE INVENTION

The invention represents a significant breakthrough in the treatment of cancer in that tumor antigens for vaccination are generated without having to take a biopsy from the patient, process the tumor cells ex vivo, and then vaccinate the patient with processed tumor antigen. One can now achieve patient-specific cancer vaccines, without needing patient-specific manufacturing of the vaccine, via the generation of cancer antigens in situ using a scaffold that is implanted in the body. Live cancer cells are recruited to the 3-dimensional (3-D) vaccine scaffold following its placement in the patient, and the scaffold is treated to induce subsequent destruction of the recruited cancer cells. The destruction and/or lysis of the cancer cells generates antigens in situ in the scaffold.

Accordingly, the invention features a biopsy-free method for producing a processed (e.g., cell-dissociated) tumor antigen in situ. For example, the tumor antigen(s) are liberated from an intact tumor cell, associated with cell fragments, or associated with a cell that has been altered from its naturally-occurring state. First, a porous 3-dimensional scaffold is administered to a subject diagnosed with a cancer. The scaffold comprises a chemoattractant of cancer cells. Such molecules (and their amino acid (aa) and nucleic acid (na) sequences) are well known in the art. For example, the chemoattractant of cancer cells is a chemokine selected from the group consisting of chemokine (C-C motif) ligand 21 (CCL-21, GenBank Accession Number: (aa) CAG29322.1 (GI:47496599), (na) EF064765.1 (GI:117606581), incorporated herein by reference), chemokine (C-C motif) ligand 19 (CCL-19, GenBank Accession Number: (aa) CAG33149.1 (GI:48145853), (na) NM_006274.2 (GI:22165424), incorporated herein by reference), stromal cell-derived factor-1 (SDF-1, GenBank Accession Number, (aa) ABC69270.1 (GI:85067619), (na) EQ9669.1 (GI:22026296), incorporated herein by reference), vascular endothelial growth factor (e.g., VEGFA; GenBank Accession Number: (aa) AAA35789.1 (GI:181971), (na) NM_001171630.1 (GI:284172472), incorporated herein by reference), and interleukin-4 (IL-4, GenBank Accession Number: (aa) AAH70123.1 (GI:47123367), incorporated herein by reference).

The scaffold is maintained in situ for a time period sufficient to accumulate circulating cancer cells, thereby yielding a cancer cell-containing scaffold. Finally, the cell-containing scaffold is contacted with a cytotoxic or cytolytic element to produce a processed tumor antigen. A cytotoxic or cytolytic element is a composition and/or condition that causes death or lysis, respectively, of a cell. For example, the cell is a cancer cell. The patient to be treated comprises a cancer that is characterized by circulating tumor cells, e.g., metastatic tumor cells. For example, the subject is diagnosed with a metastatic cancer condition or a blood-borne cancer or cancer of the circulatory system, e.g., leukemia. The cytotoxic or cytolytic element comprises a heat-conducting composition such as gold particles and/or the application of external heat, ultrasound, laser radiation, or gamma radiation. For example, cytotoxicity or cytolysis of a cancer cell is induced by applying a condition (e.g., an energy source such as those described above) to a cell-containing scaffold that also contains a heat-conducting composition. Suitable types of laser radiation include ultraviolet or near infrared laser radiation.

Exemplary scaffold compositions are described in U.S. 2008-0044900 A1 (incorporated herein by reference). Suitable scaffolds include polylactic acid, polyglycolic acid, co-polymers of polylactic acid and polyglycolic acid (e.g., PLGA polymers), alginates and alginate derivatives, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly(uronic acids), poly (vinylpyrrolidone) and copolymers or graft copolymers of any of the above. One preferred scaffold composition includes an RGD-modified alginate.

The scaffold composition is between 0.01 mm$^3$ and 100 mm$^3$. For example, the scaffold composition is between 1 mm$^3$ and 75 mm$^3$, between 5 mm$^3$ and 50 mm$^3$, between 10 mm$^3$ and 25 mm$^3$. Preferably, the scaffold composition is between 1 mm$^3$ and 10 mm$^3$ in size.

The porosity of the scaffold influences ingress/egress of the cells from the device. Pores are nanoporous, microporous, or macroporous. The porous polymer device contains aligned and/or interconnected pores to facilitate movement of cells into and out of the device. For example, immune cells such as DCs are recruited into the device, pick up antigen, e.g., antigen that has been liberated from cancer cells that have been attracted to the device, and then migrate out of the device via the interconnected pores to leave the device and go to other sites in the body such as draining lymph nodes. For example, the diameter of nanopores are less than about 10 nm; micropores are in the range of about 100 nm-20 µm in diameter; and, macropores are greater than about 20 µm (preferably greater than about 100 µm, 200 µm, 300 µm and even greater than about 400 µm). In one example, the scaffold is macroporous with aligned or interconnected pores of about 400-500 µm in diameter.

Optionally, the scaffold further comprises a hyperthermia-inducing composition. Suitable hyperthermia-inducing compositions include a magnetic nanoparticle or a near infrared (NIR) absorbing nanoparticle. In some cases, the nanoparticle is magnetic, and the method further comprises contacting the magnetic nanoparticle with an alternative magnetic field (AMF) to induce local hyperthermia in situ, thereby altering or disrupting the cancer cell and producing a processed tumor antigen. In another example, the method further comprises contacting the NIR nanoparticle with NIR radiation to induce local hyperthermia in situ, thereby altering or disrupting the cancer cell and producing a processed tumor antigen. Hyperthermia is characterized by a local temperature of greater than 37 degrees Celsius. For example, the temperature of the device is temporarily heated to 40, 45, 50, 60, 70, 75, 80, 85, 90, 95 or more degrees.

The size of the particles is tailored to the scaffolds of the invention. For example, the nanoparticle comprises a diameter of less than 200 nm, e.g., a diameter of greater than 2 nm and less than 150 nm, e.g., a diameter of 5-100 nm, e.g., a diameter of 10-50 nm. Exemplary particles are less than 45 nm, e.g., 40 nm, or less than 15 nm, e.g., 13 nm. A suitable NIR nanoparticle includes a gold nanorod, gold nanoshell, silica nanoparticle, gold nanocage, noble metal nanoparticle, carbon nanotube, carbon nanoparticle, and graphite nanoparticle.

The methods described herein are useful in the treatment of cancer in a mammal. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

The invention also provides a tumor antigen-processing device comprising a porous polymer, a chemoattractant for cancer cells, and a cell-altering or cell-destroying (e.g., cytotoxic or cytolytic) composition or element such as a hyperthermia-inducing particle. A hyperthermia-inducing nanoparticle is one that heats the cells within the scaffold to a cell-destructive temperature upon the application of an external energy source. For example, the energy source is a form of radiation such as heat, AMF or NIR.

An exemplary device comprises an immune cell (e.g., DC) recruitment composition such as granulocyte macrophage colony-stimulating factor (GM-CSF). In one example, the chemoattractant, cytoxicity- or cytolysis-composition, and immune cell recruitment composition are interspersed throughout the porous polymer. In another example, the porous polymer comprises a first zone comprising the chemoattractant and cytoxicity-inducing or cytolysis-inducing composition and a second zone comprising the immune cell recruitment composition. In the latter example, the zones are layered or constructed with a core-shell architecture, whereby the first zone is configured as a core and the second zone is configured as a shell. Exemplary cytotoxicity-inducing (or cytolysis-inducing) compositions are described above, e.g., hyperthermia-inducing particles.

As used herein, an "isolated" or "purified" nucleotide or polypeptide (e.g., a chemoattractant, cytokine, or chemokine nucleotide or polypeptide) is substantially free of other nucleotides and polypeptides. Purified nucleotides and polypeptides are also free of cellular material or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified nucleotides and polypeptides, e.g., a chemoattractant, cytokine, or chemokine is one that is at least 90%, 91%, 92%, 93%, 94%, 95%, 98%, 99%, or 100% (w/w) of the desired oligosaccharide by weight. Purity is measured by any appropriate standard method, for example, by column chromatography, thin layer chromatography, or high-performance liquid chromatography (HPLC) analysis. The nucleotides and polypeptides are purified and used in a number of products for consumption by humans as well as animals, such as companion animals (dogs, cats) as well as livestock (bovine, equine, ovine, caprine, or porcine animals, as well as poultry). "Purified" also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

Small molecules include, but are not limited to, peptides, peptidomimetics (e.g., peptoids), amino acids, amino acid analogs, polynucleotides, polynucleotide analogs, nucleotides, nucleotide analogs, organic and inorganic compounds (including heterorganic and organometallic compounds) having a molecular weight less than about 5,000 grams per mole, organic or inorganic compounds having a molecular weight less than about 2,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

By the terms "effective amount" and "therapeutically effective amount" of a formulation or formulation component is meant a sufficient amount of the formulation or component to provide the desired effect. For example, "an effective amount" of a chemoattractant of cancer cells is an amount of a compound required to mediate an accumulation of two or more cancer cells in the scaffold device prior to application of a cell-altering or cell-destroying stimulus. Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps and permits those that do not materially affect the basic and novel characteristic(s) of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIG. 6A is a photograph of a scaffold in which gold nanorods (GNRs) were incorporated in poly(lactide and glycolide) (PLG) macroporous scaffold (GNR-PLG scaffold).

FIG. 6B is a photomicrograph illustrating a microscopic view of the macroporous scaffold structure. The bar scale in the lower left-hand corner is 200 µm.

FIG. 6C is a photomicrograph showing gold nanorods (GNRs) coated with poly(ethylene glycol) (PEG).

DETAILED DESCRIPTION

Figure 1:
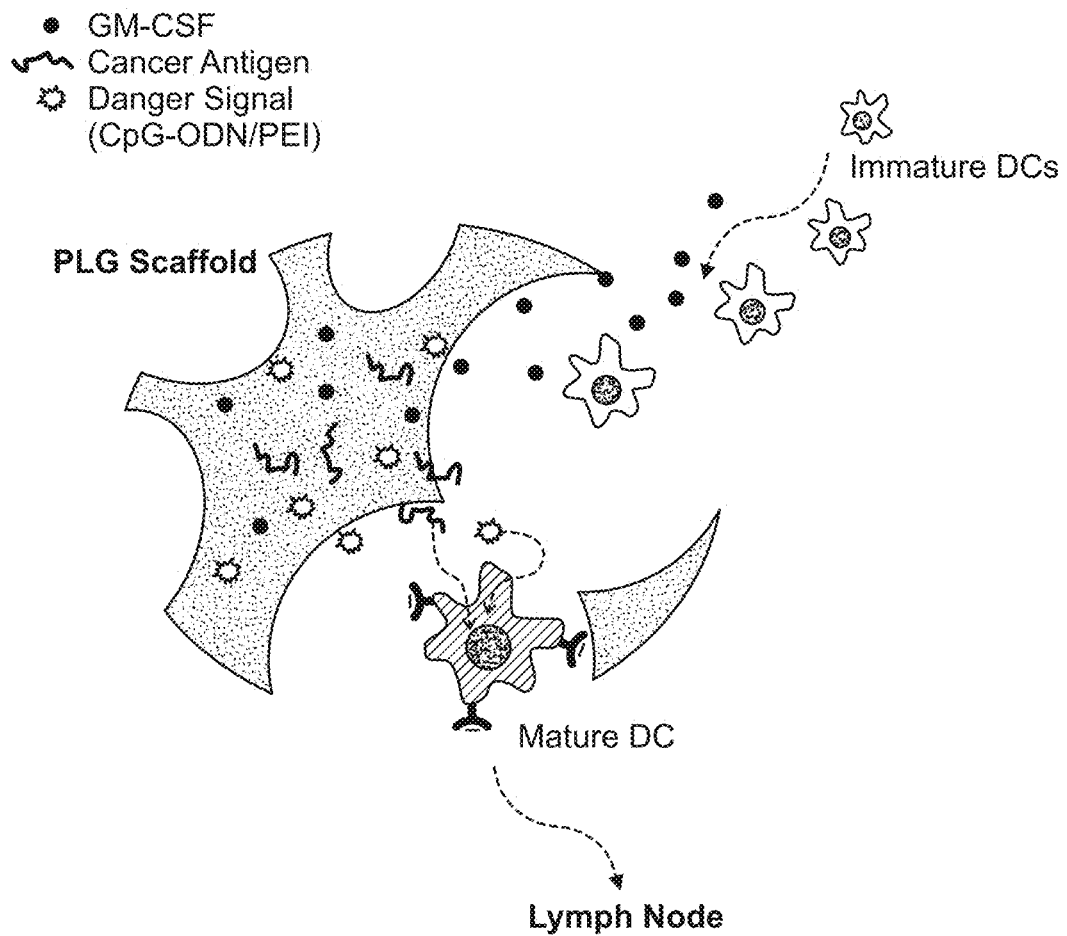
FIG. 1 is a diagram of recruitment of peripheral dendritic cells (DCs) to the scaffold, loading of recruited DCs with cancer antigen, and DC maturation (induced by danger signals) such as CpG oligodeoxynucleotides (CpG-ODN)/poly(ethyleneimine) (PEI), e.g., PEI-condensed CpG ODN.

Three dimensional (3D) scaffolds provide a temporary residence for dendritic cells (DCs) and effectively regulate host DC trafficking and activation in situ, while simultaneously preventing upregulation of the tolerizing arm of the immune system, and provide therapeutic protection against cancer. For example, in the cancer vaccine systems described herein, implantation of macroporous poly(lactide and glycolide) (PLG) scaffolds loaded with chemoattractant (GM-CSF) of DCs, cancer antigens (tumor lysates), and danger signals (CpG oligonucleotide) resulted in recruitment of peripheral DCs to the scaffold, loading of recruited DCs with cancer antigen, and their maturation by danger signals (FIG. 1). The antigen-presenting mature DCs moved to lymph nodes and generated potent cytotoxic T lymphocyte (CTL) responses. In this manner, this vaccine system triggered a strong anticancer immune response, which allowed the eradication of the cancer. One such system utilizes a tumor biopsy from the patient to be treated to generate the antigen, which requires ex vivo manipulation and processing of tumor tissue. In addition, this system requires that each vaccine be manufactured for the specific individual to be treated (using the tumor lysate from that same patient). The methods of the present invention represent an improvement of the heretofore-described system.

Figure 2:
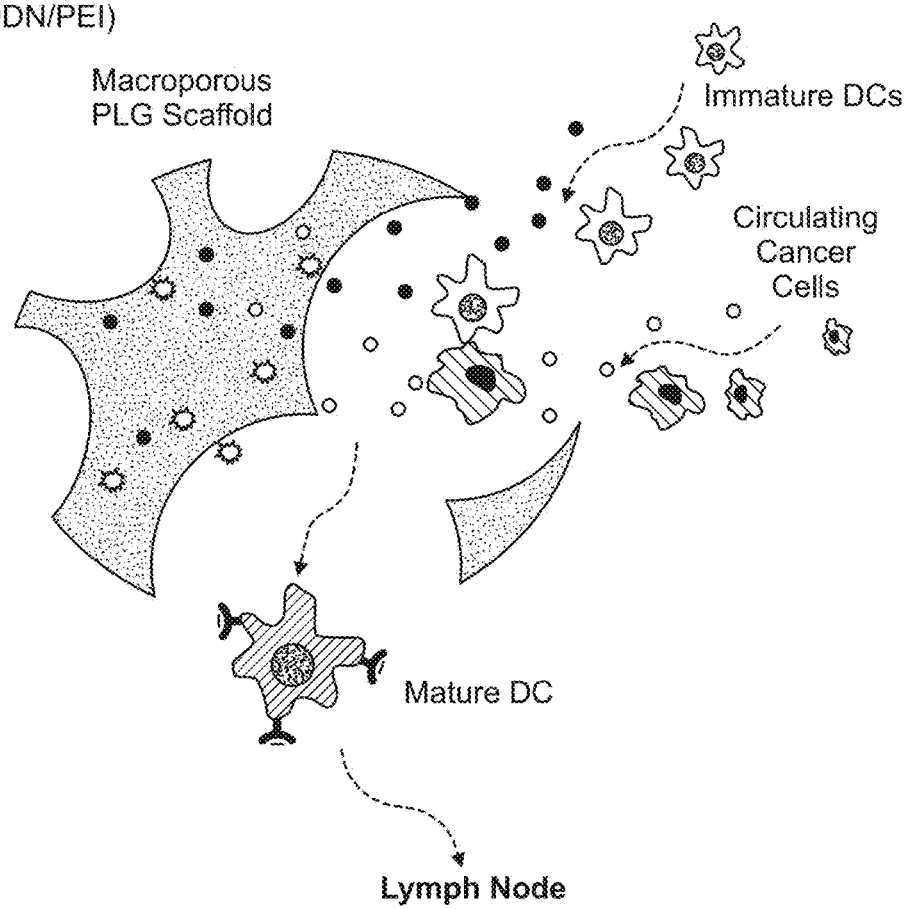
FIG. 2 is a diagram of circulating endogenous cancer cells being recruited to the vaccine scaffold following implantation in the patient, subsequent destruction of the recruited cancer cells leading to liberation of tumor antigens in situ in the scaffold, and DC activation/loading with liberated tumor antigen.

As described herein, a patient-specific anti-tumor immune response and a reduction in tumor burden is achieved, without patient-specific manufacturing of the vaccine. Instead, cancer antigens are generated in situ in a polymeric scaffold that was implanted in the body. Live cancer cells present in the circulatory system of the subject are recruited to the vaccine scaffold following its placement in the patient, and the subsequent destruction of the recruited cancer cells generates antigens in situ in the scaffold (FIG. 2).

Recruitment of Circulating Cancer Cells to scaffolds

Suitable cancers to be treated in this manner are those in which there are circulating primary or metastatic cancer cells in the blood stream. These cells are characterized by migratory properties in response to gradients of specific chemokines. Thus, circulating cancer cells are recruited to implanted scaffolds in which specific chemokines have been incorporated.

Circulating cancer cells: metastatic cancer cells in various cancers, leukemic cells.

Chemoattractant of cancer cells: various chemokines depending on cancer type. (e.g., CCL-21, CCL-19, SDF-1, VEGF, IL-4 etc.).

3D scaffolds: various types of 3D scaffolds designed to have pores and to load chemokines including biodegradable porous polymer, porous inorganic materials, assembled nanoparticles, nanotubes, nanorods, etc.

Destruction of the Recruited Cancer Cells by External Stimuli on Scaffolds

As described below, in addition to recruitment of cancer cells to scaffolds, various external stimuli are used to kill the cancer cells after they are recruited in order to generate lysates containing cancer antigens in situ. External stimuli applicable to implanted scaffolds to kill the recruited cancer cells.

External Heating

Ultrasound

Laser irradiation: UV, Near infrared laser

Gamma irradiation

Nanoparticle (NP)-mediated hyperthermia

Alternative magnetic field (AMF) for scaffold loaded with magnetic nanoparticles.

Near infrared (NIR) irradiation for scaffold loaded with NIR absorbing nanoparticles (e.g., gold nanorods, gold nanoshells, gold nanocages, other noble metal nanoparticles, carbon nanotubes, carbon nanoparticles, graphite, etc.)

Separating the Manipulation of Recruited DCs and Cancer Cells

Sometimes it is desirable to separate the recruited DCs and cancer cells so the signals used to kill the cancer cells do not negatively impact the DC functions. As described below, this segregation is accomplished via control over the temporal order of recruitment of each cell type, or a spatial segregation of the cells that allows application of external stimuli to a specific region of scaffold.

Temporal Control of the Order of Cell Recruitment

Rather than recruiting all cells simultaneously, cancer cells are first recruited and destroyed to generate a lysate. Subsequently, cancer cells recruit DCs to the site of the cancer antigens without damaging DCs by external stimuli. For this purpose, it is possible to control of the release profiles from scaffolds of different chemoattractants to DCs and cancer cells. For example, different composition of polymers with different degradation profiles and/or different molecular affinities to each chemokine are used in the preparation of a polymer vaccine scaffold to control release profiles.

Spatial Control of Scaffolds to Allow Applying External Stimuli to Specific Region of Scaffold Scaffolds are also compartmentalized such that only certain compartments are affected by the external stimuli to specifically kill the cancer cells residing in those compartments, thereby allowing for the maintenance of intact and functional DCs in other compartments. For this purpose, various structural modifications of scaffolds are utilized. In the case of nanoparticle (NP)-mediated hyperthermia for killing of cancer cells, NPs are incorporated in specific regions of the scaffolds, which allows specific hyperthermia in the NP-region and has a trivial hyperthermic effect to other regions where DCs are recruited.

In Situ Antigen-Generating Cancer Vaccine

Immunotherapy with protein drugs (e.g., cytokines and monoclonal antibodies) is one approach for cancer management. Therapeutic cancer vaccines, another form of immunotherapy, represent another approach to treat cancer. Cancer vaccines are designed to invoke strong anti-tumor immune activity, and the induction of antigen-specific cytotoxic (CD8+) T lymphocytes (CTLs) is a critical aspect of their function. Activated CD8+ T cells kill tumor cells upon recognition of specific labels (antigens) present on tumor cells, and this recognition is dependent on binding of the label to a T cell receptor (TCR) specific to that antigen. Dendritic cells (DCs) are the most important antigen presenting cells (APCs), and play a key role in initiating CTL responses.

Prior to the invention described herein, the first DC-based therapeutic cancer vaccine, known as Provenge, was approved by the Food and Drug Administration. This breakthrough in cancer therapy demonstrated that the stimulation of a patient's own immune system to fight cancer. However, this therapy is based on ex vivo manipulation of DCs in order to generate large numbers of these cells, and to activate the cells with cancer antigen, and thus suffers from a high cost and significant regulatory burden. In addition, tumors were not eradicated with this therapy, and the increase in patient survival time has been limited to 4 months. While this breakthrough may have a major impact on cancer treatment, it also highlights the need to make further progress on the DC-based cancer vaccine strategy, and to bypass its dependency on ex vivo manipulation.

Developments in material science have led to new biomaterials and the applications of materials in a wide range of biomedical applications, including diagnostics, cancer therapy, and tissue regeneration. In particular, nanoparticles and macroscopic, three-dimensional biomaterials have significant potential in many clinical applications. As described herein, because of their nanosize and easy surface modification, targeting of nanoparticles to various tissues, including tumors and lymph nodes is exploited to deliver imaging or therapeutic modalities. 3-D macroscale biomaterials, especially porous scaffolds, have been extensively explored for applications involving the controlled release of growth factors, cell delivery, and tissue regeneration. These materials create microenvironments that allow the fate of resident cells to be modulated, typically via control over the physical properties and presentation of cell signaling molecules from the walls of the materials. These 3-D macroscale materials and nanoparticles are useful in the development of vaccines in the context of cancer, particularly via the targeting and programming of specific immune cell populations.

As described in the examples below, porous polymer matrices that provide a temporary residence for DCs effectively regulate host DC trafficking and activation in situ, while simultaneously preventing upregulation of the tolerizing arm of the immune system, and provide therapeutic protection against cancer. Macroporous PLG scaffolds incorporating i) GM-CSF to recruit DCs, ii) CpG/PEI complex to mature the DCs, and iii) tumor lysate to provide a mixture of cancer antigens were developed for this purpose. Upon subcutaneous implantation, GM-CSF was released and established a gradient in the surrounding tissue to recruit significant numbers of host DCs. The presentation of CpG/PEI complex from the polymer to the recruited DCs increased the maturation of DCs in the scaffolds and their LN-homing. These scaffolds induced strong specific CTL responses to melanoma in a prophylactic model, with a 90% survival rate as well as in therapeutic models of melanoma and glioblastoma with over a 50% survival rate after vaccinations. This system recruited various DC subsets, including significant numbers of plasmacytoid DCs (pDCs) and CD8+ DCs, which are very important in antigen cross presentation, and the numbers of these DC subsets strongly correlated with the vaccine efficacy. This vaccine also diminished the local concentrations of tolerogenic cytokines (e.g., IL-10, TGF-β), and numbers of T regulatory cells, suggesting that a key aspect of its success related to its ability to down-regulate tolerance. These effects were only found when the polymer had the physical form of a macroporous scaffold, as the vaccine effectiveness was significantly diminished when polymer microspheres were used instead to provide a sustained, localized release of the bioactive agents, without providing a residence for the recruited cells. This result indicates that creating a microenvironment in which host environmental cues are minimized, and exogenous maturation factors are highly concentrated, is a key to reprogram immune responses in situations such as cancer where there exist significant, pathology-associated tolerizing cues.

However, a limitation in this system is that it requires a tumor biopsy from patients and ex vivo manipulation and processing to generate cancer antigens. A system to generate cancer antigens in situ in the scaffold implanted in the body without biopsy or any ex vivo manipulation of cells represents an improvement over earlier systems. To make a patient-specific cancer vaccine, an improved scaffold system was developed in which cancer cells are recruited to a 3D vaccine scaffold and the alteration or destruction of those recruited cancer cells generates cell lysates in situ in the scaffold.

Figure 3:
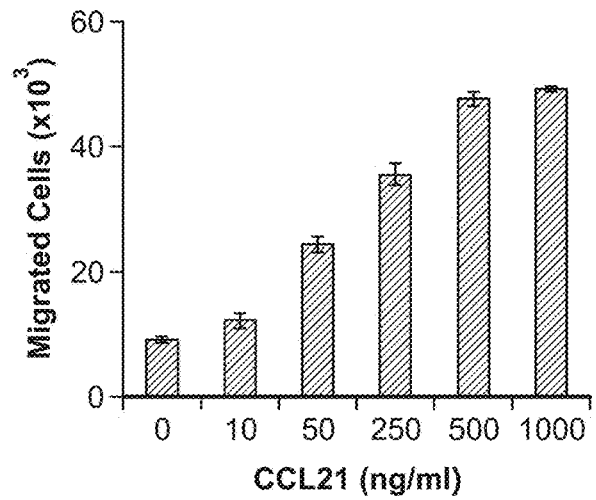
FIG. 3 is a bar graph showing migration of leukemia cells in response to a gradient of CCL-21.

Example 1: In Situ Antigen-Generating Cancer Vaccine by Recruiting Cancer Cells and Subsequent Destruction of the Recruited Cancer Cells by External Stimuli Described below are examples of gold nanorod-loaded cancer vaccine scaffolds to recruit leukemic cells and their subsequent destruction via NIR irradiation-mediated hyperthermia to generate cancer antigen coupled with heat shock protein. To demonstrate the scaffolds are capable of recruiting cancer cells, mouse leukemic cells (C1498) were tested in transwell assay using CCL-21 as the chemoattractant. C1498 showed strong migration to the gradients of CCL-21 (FIG. 3).

Example 2: In Vivo Recruitment of Leukemic Cells

Figure 4:
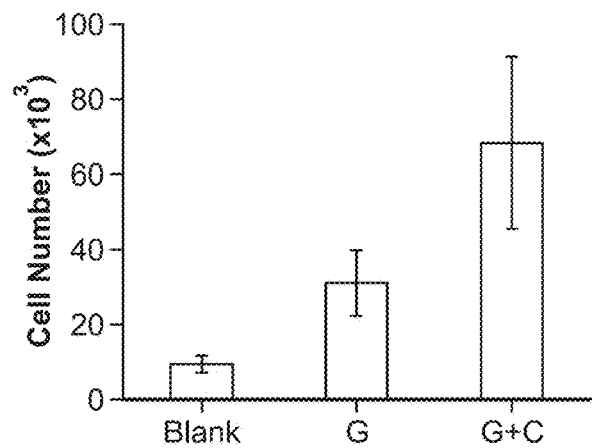
FIG. 4 is a bar graph showing in vivo recruitment of leukemic cells to blank and loaded scaffolds.
Figure 5:
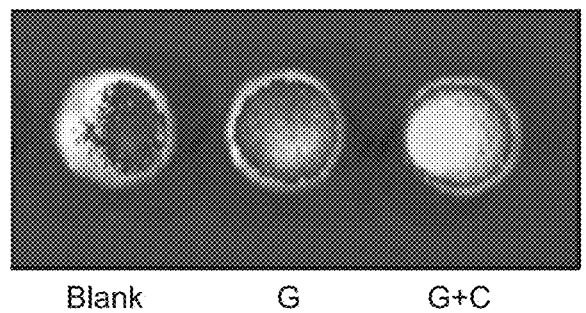
FIG. 5 is a photograph of explanted scaffolds retrieved from mice showing fluorescent-nano particle (NP)-labeled leukemic cells that were recruited into the scaffold by CCL-21.

In vivo recruitment of leukemic cells was characterized using GFP-expressing leukemic cells. PLG scaffolds without any chemokines (Blank), loaded with GM-CSF (G), and loaded with GM-CSF and CCL-21(G+C) were implanted to C57BL/6J mice subcutaneously and GFP-leukemic cells were injected into blood via tail vein injection at Day 4. The scaffolds were retrieved at Day 6 and the cells in scaffolds were isolated and analyzed in FACS (FIG. 4). In addition, the scaffolds retrieved from mice injected with fluorescent-NP-labeled leukemic cells were imaged under fluorescent imaging instrument (Xenogel) (FIG. 5). Both results presented that CCL-21 released from scaffold increased the recruitment of leukemic cells in the animal.

Example 3: Hyperthermia-Mediated Antigen Generation

To achieve hyperthermia-mediated antigen generation from recruited cancer cells, gold nanorods (GNRs) were incorporated in PLG macroporous scaffold (GNR-PLG scaffold) during the fabrication step (FIG. 6). GNR-PLG scaffold had 250-440 μm pores and GNRs were incorporated over the whole scaffold, resulting in dark color in the resulting PLG scaffold. The surface of GNRs were modified with poly(ethylene glycol) (PEG) to remove the toxicity from original surfactants (cetyltrimethylammonium bromide) used in GNR-fabrication step which is known as toxic agents to the cells.

Figure 7A:
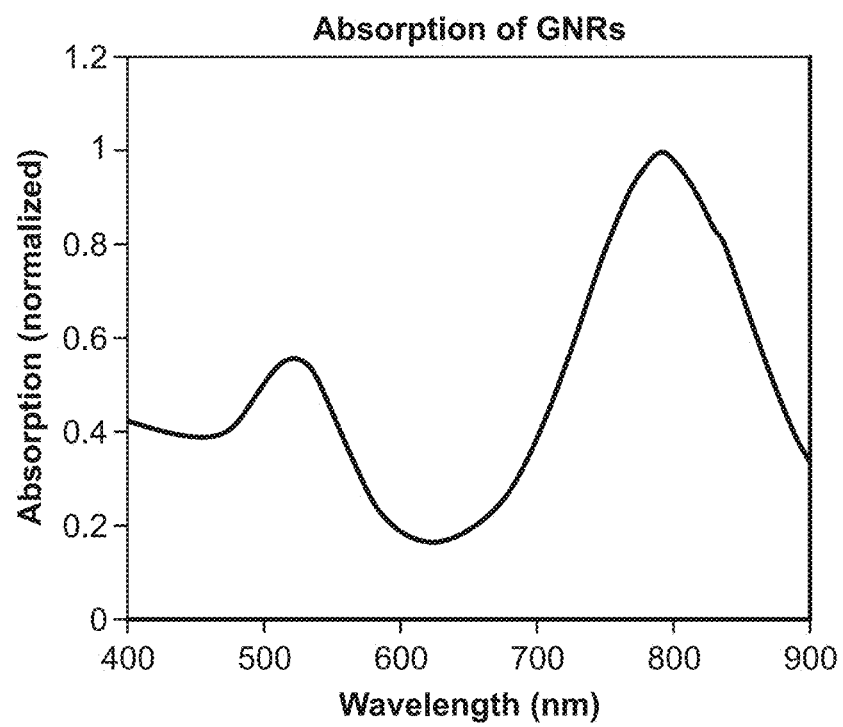
FIG. 7A is a line graph showing the intrinsic maximum absorption of GNRs incorporated in the PLG scaffold.
Figure 7B:
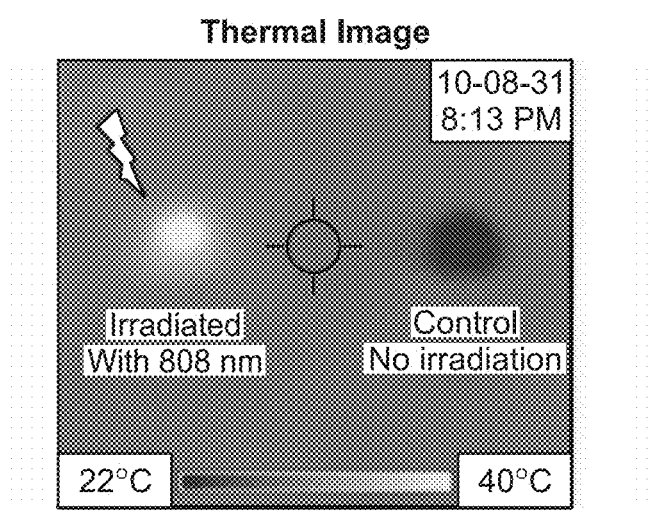
FIG. 7B is a photomicrograph of a thermal image of a GNR-PLG scaffold after irradiation with 808 nm continuous diode laser.

GNRs incorporated in PLG scaffold showed intrinsic maximum absorption at ~810 nm with maximum intensity, which is desirable for in vivo irradiation due to minimum absorption by tissue and water in that range of wavelength (FIG. 7A). Upon irradiation with 808 nm continuous diode laser, the temperature of GNR-PLG scaffold was increased to 40° C. (FIG. 7B) from room temperature.

Figure 8A:
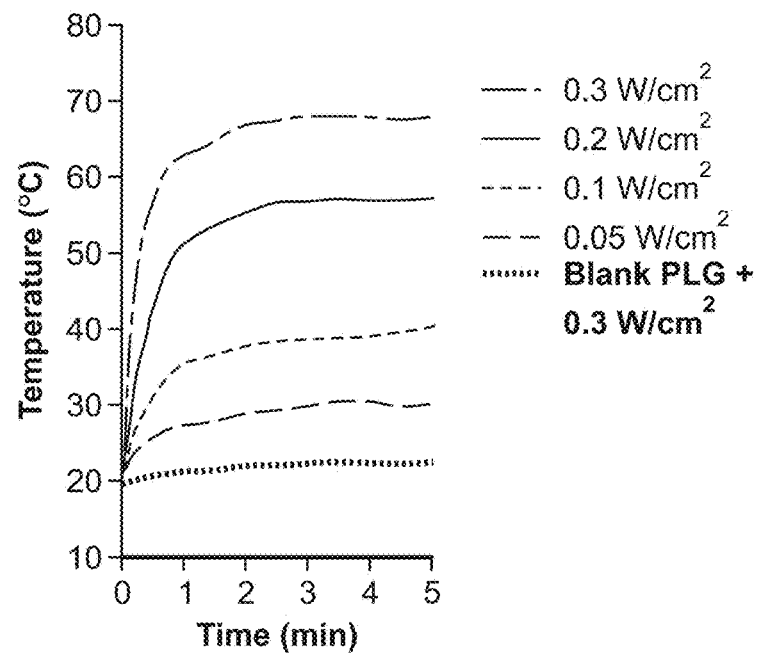
FIG. 8A is a line graph demonstrating the temperature of GNR-PLG scaffolds after application of a different laser power.
Figure 8B:
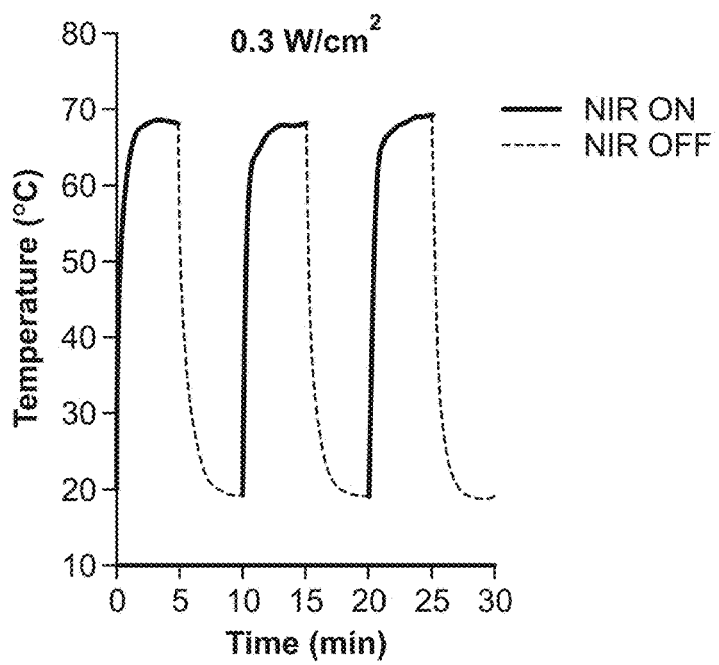
FIG. 8B is a line graph demonstrating that repetitive near infrared (NIR) irradiation allowed multiple hyperthermia in the same GNR-PLG scaffold.

As described below, the temperature of GNR-PLG scaffolds were controlled in the range from room temperature up to ~70° C. by applying different power of laser (FIG. 8A). By contrast, blank scaffold without incorporation of GNRs showed insignificant change in temperature upon irradiation with even highest power that was applied to GNR-PLG scaffold, representing the NIR-mediated hyperthermia could be induced specifically in GNR-incorporated scaffold. Optionally, multiple antigen generation is used to elicit a strong immune activation. The repetitive NIR irradiation allowed multiple hyperthermia in same GNR-PLG scaffold without decrease of the targeting temperature by using same laser power (FIG. 8B).

Example 4: GNR Absorption of NIR Light

Figure 9:
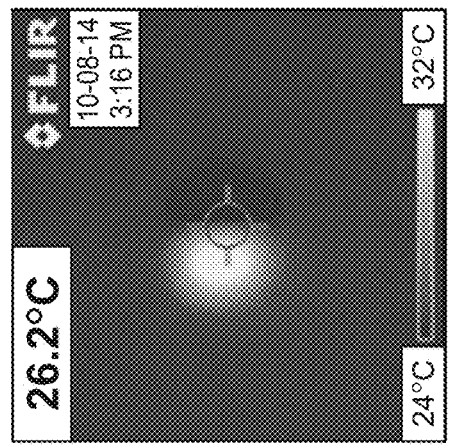
FIG. 9 is a photomicrograph of a thermal image of a GNR-PLG scaffold physically attached to a half blank PLG scaffold and irradiated with 808 nm laser.

Local hyperthermia for GNR-incorporated region of PLG scaffold was possible due to the absorption of NIR light by GNRs in specific area of PLG scaffold. A half GNR-PLG scaffold and a half blank PLG scaffold were physically attached and irradiated with 808 nm laser with large beam size to cover whole scaffold, resulting in specific heating in only GNR-PLG scaffold side (FIG. 9). This configuration represents a scaffold with different compartments, i.e., one for cancer cells and one for DCs that can be implanted. Only the compartment for cancer cells is heated, while the one for DCs remains intact (unheated) to allow normal DC function.

Example 5: A PLG Scaffold with a GNR-Incorporated Core and a Normal Shell

Figure 10C:
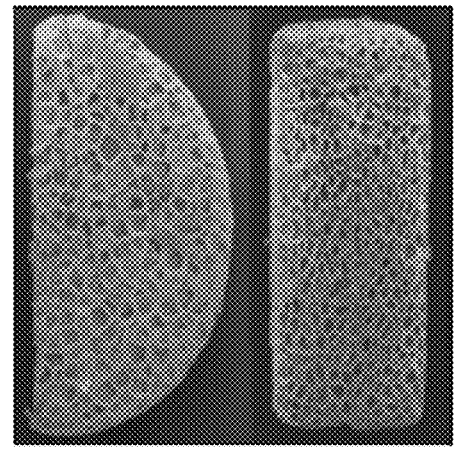
FIG. 10C is a photomicrograph showing the well-interconnected pore structure of a PLG scaffold.
Figure 10B:
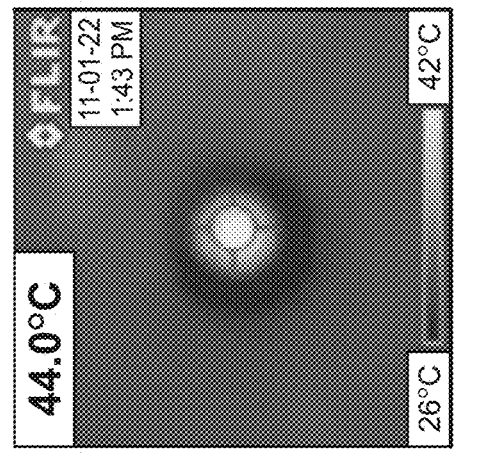
FIG. 10B is a photograph of a thermal image of a single PLG scaffold composed of a GNR-incorporated core.
Figure 10A:
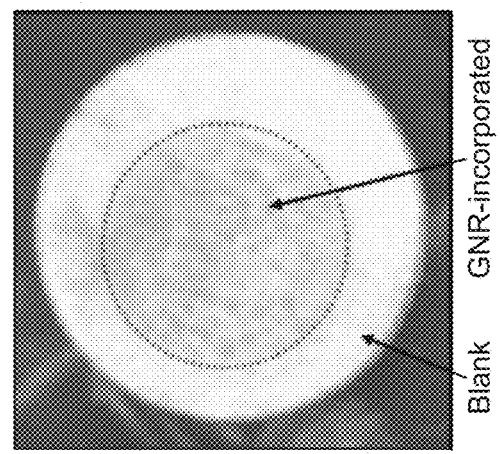
FIG. 10A is a photograph of a single PLG scaffold composed of a GNR-incorporated core.

A single PLG scaffold composed of GNR-incorporated core part and normal shell part (FIG. 10A) was fabricated for cancer-specific heating (FIG. 10B). This single PLG scaffold with different compartment and well-interconnected pore structure (FIG. 10C) allows the efficient cancer antigen uptake by DC after hyperthermia (FIG. 10C).

Example 6: Heat-Shocked Cancer Cells

Figure 11A:
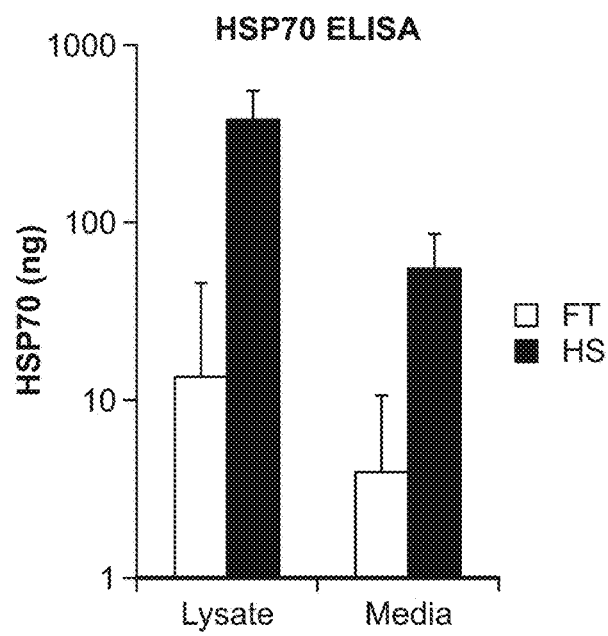
FIG. 11A is a bar chart illustrating heat shock protein (HSP) levels of cancer cell cultures after heat shock in 43° C.
Figure 11B:
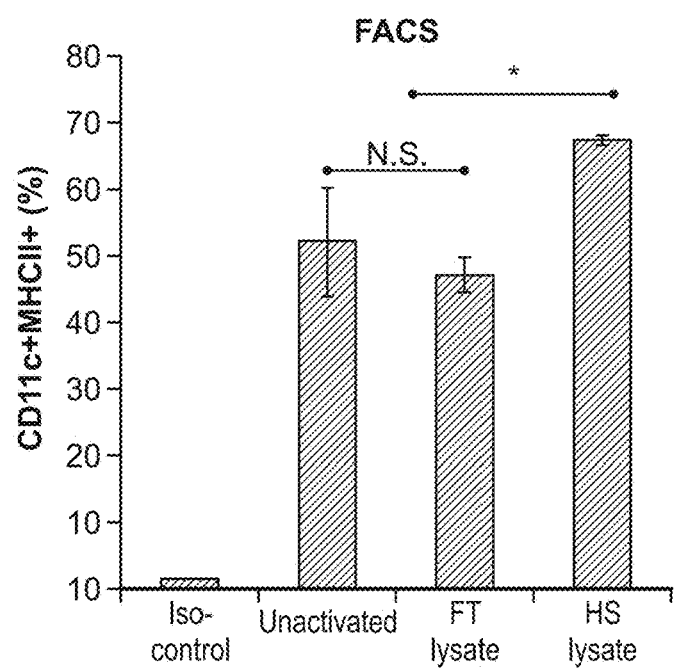
FIG. 11B is a bar chart demonstrating in vitro DC activation by heat-shocked lysate and freeze-thaw lysate.

To test if heat-shock can induce more immunogenic antigens due to adjuvant effect of HSP produced from heat-shocked cancer cells, HSP levels of cancer cell cultures were analyzed after heat shock in 43° C. water bath (FIG. 11A). Higher HSP70, a representative HSP, were obtained both the cell lysate and cell culture media in heat-shocked condition compared with freeze-thaw method, the common lysate generating method. In vitro DC-activation by heat-shocked lysate and freeze-thaw lysate showed that heat-shocked lysate have higher DC-activating property due to higher HSPs (FIG. 11B).

Example 7: NIR-Irradiation to Induce HSPs from Cancer Cells

Figure 12A:
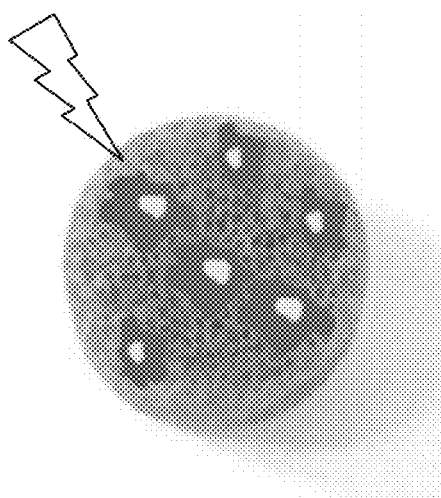
FIG. 12A is an illustration of cells (leukemic cells) in a GNR-PLG scaffold and irradiated with a laser (808 nm).
Figure 12B:
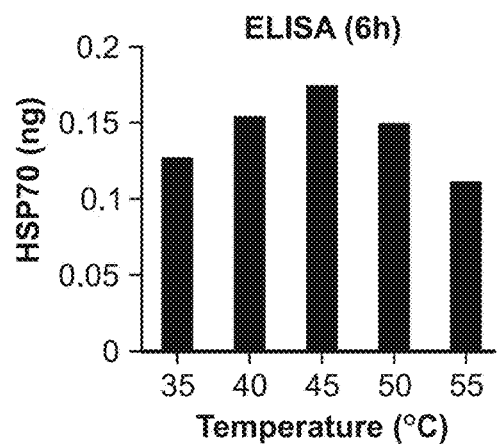
FIG. 12B is a bar chart showing the level of HSP70 in cancer cells after exposure to various temperatures.
Figure 12C:
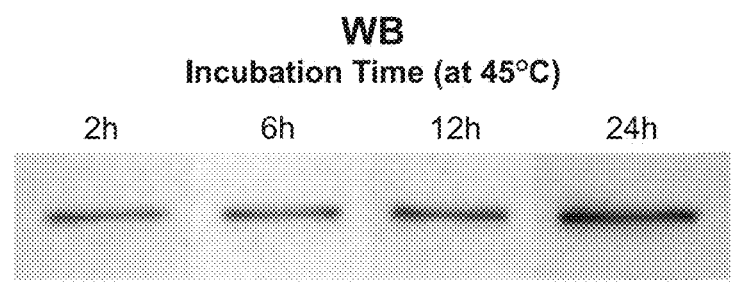
FIG. 12C is a photograph of a western blot showing that 24 hour incubation after irradiation at 45° C. generated the highest HSP levels.

To test if NIR-irradiation on GNR-PLG scaffold can induce HSPs from cancer cells residing in scaffold, leukemic cells were seeded in GNR-PLG scaffold and subsequently irradiated with 808 nm laser (FIG. 12A). The various temperatures by irradiation were tested for to evaluate HSP70 levels, representing that irradiating to 45° C. resulted maximum HSP70 level (FIG. 12B). In addition, Western blot data showed that 24 hour incubation after irradiation at 45° C. generated highest HSPs.

Example 8: Activation of Dendritic Cells

Figure 13:
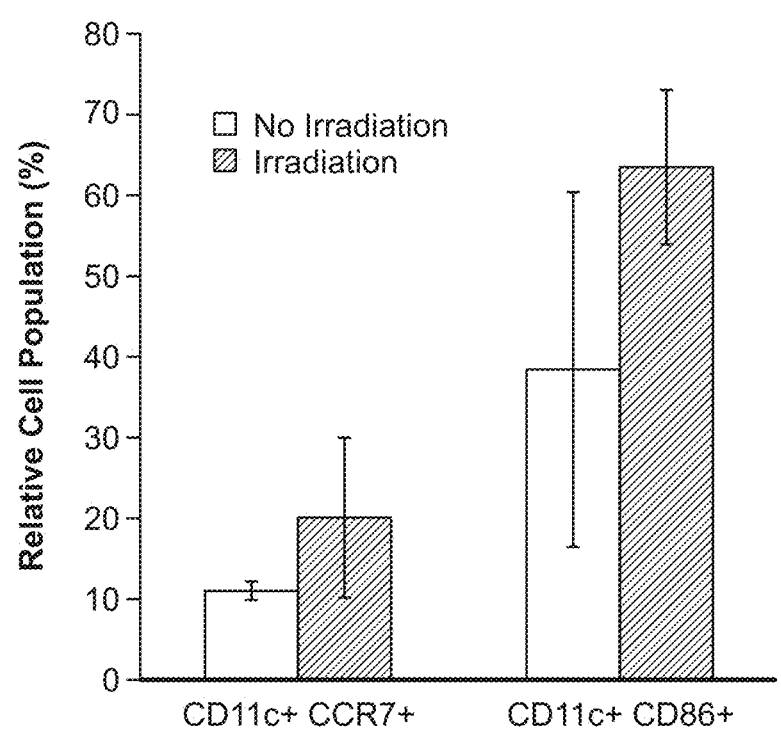
FIG. 13 is a bar chart representing the relative cell population in a GNR-PLG scaffold with activated DC cell surface markers after NIR irradiation at 45° C.

In vitro DC, e.g., bone-marrow derived dendritic cells (BMDC), activation with cell lysates from GNR-PLG scaffold after NIR irradiation at 45° C. resulted in higher activation of DCs compared with non-irradiated cell lysates in terms of CCR7 and CD86, the representative cell surface markers of activated DCs (FIG. 13), representing NIR irradiation leads to in situ generation of highly immunogenic cancer antigens from cancer cells residing in GNR-PLG scaffold.

Example 9: Cancer Cell Viability after NIR Irradiation In Vitro

Figure 14A:
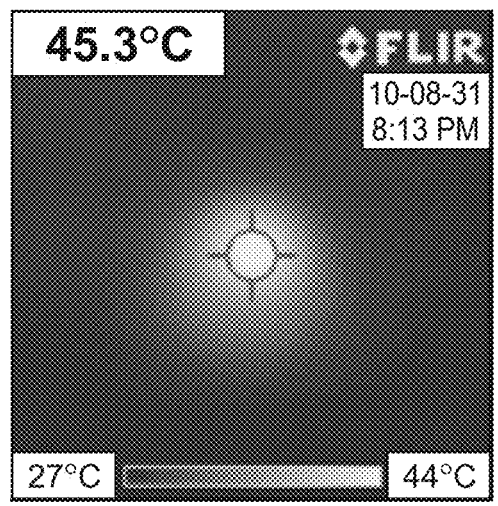
FIG. 14A is a photograph of a thermal image of an NIR irradiated GNR-PLG scaffold seeded with leukemic cells.
Figure 14B:
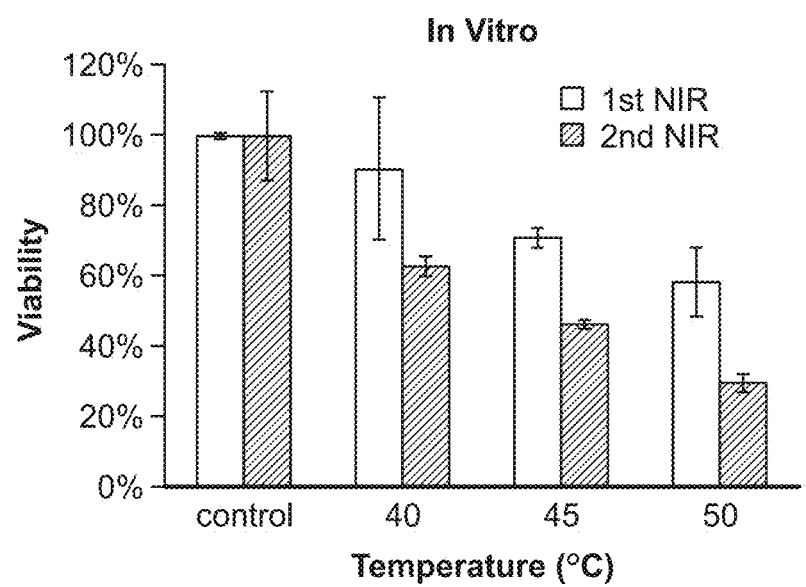
FIG. 14B is a bar chart showing leukemic cell viability in a GNR-PLG scaffold after application of NIR irradiation.

In vitro cancer cell viability in GNR-PLG scaffold after NIR irradiation was evaluated. Leukemic cells were seeded in GNR-PLG scaffold and NIR irradiation was applied to increase temperature to 40, 45, and 50° C., and the viability of cells was checked with Alamar blue assay (FIG. 14). Lower cell viability resulted from higher temperature. In addition, a second irradiation resulted in even lower viability in all conditions. These data indicate that the cancer cells were dying due to hyperthermia caused by NIR irradiation in GNR-PLG scaffold.

Example 10: Cancer Cell Viability after NIR Irradiation in Vivo

Figure 15A:
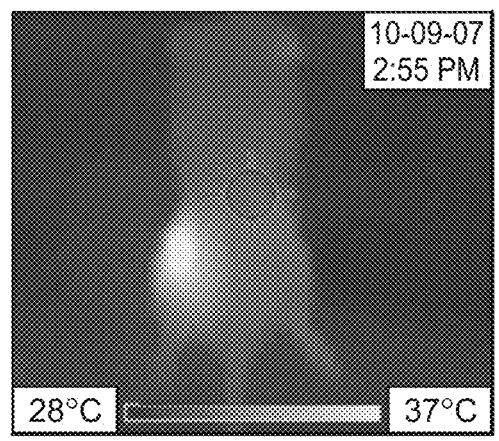
FIG. 15A is a photograph of a thermal image of an NIR irradiated GNR-PLG scaffold seeded with leukemic cells subcutaneously implanted in a C57BL/6J mouse.
Figure 15B:
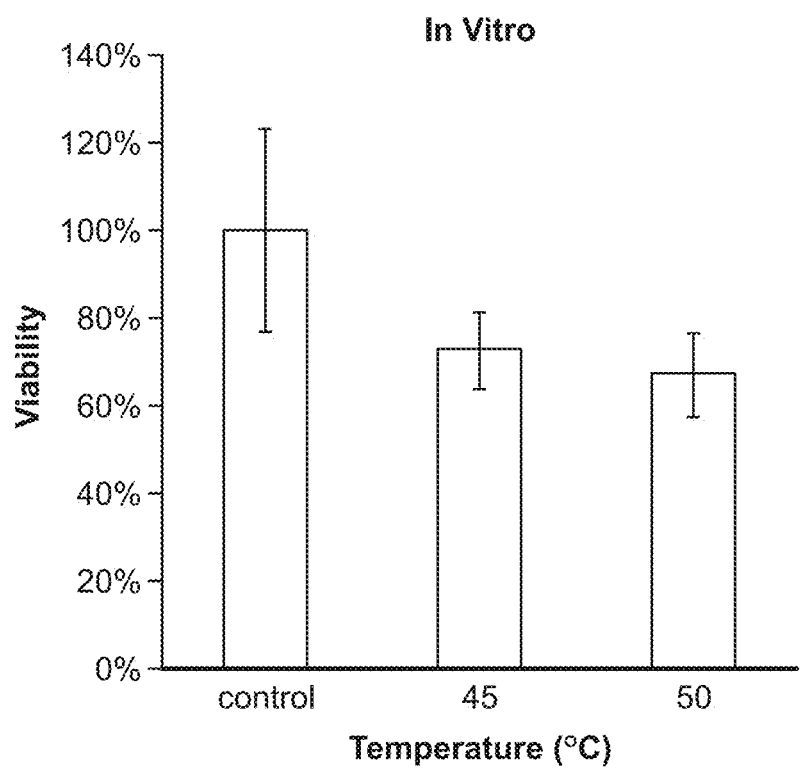
FIG. 15B is a bar graph of a bar chart showing in vivo leukemic cell viability in a GNR-PLG scaffold after application of NIR irradiation.

To mimic in vivo recruitment, the GNR-PLG scaffold seeded with leukemic cells were implanted into the tissues of C57BL/6J mice subcutaneously, and the scaffolds were irradiated with NIR laser to 45 and 50° C. Similar to the in vitro experiments, the cell viability was decreased in conditions of higher temperatures (FIG. 15), indicating that the NIR-irradiation induced heat-shock to the recruited cancer cells in GNR-PLG scaffold. Recruitment of circulating cancer cells into the implanted scaffold device, alteration or destruction of the cancer cells by application of an external force, e.g., radiation, leads to increased availability of tumor antigens in the device. The increased availability of tumor antigens in the device for cancer leads to an increase in DC activation and to a more effective cancer vaccine.

Figure 16A:
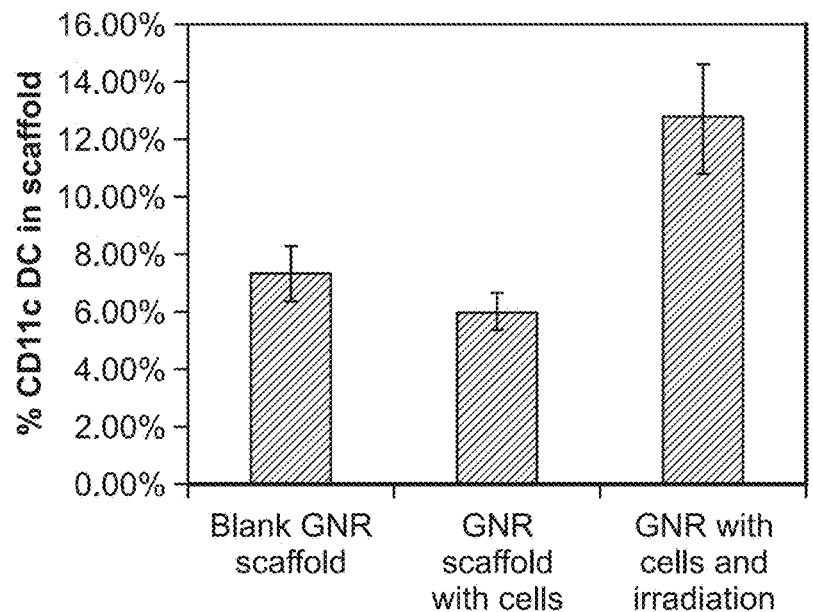
FIGS. 16A-B are bar graphs showing DC recruitment and activation.
Figure 16B:
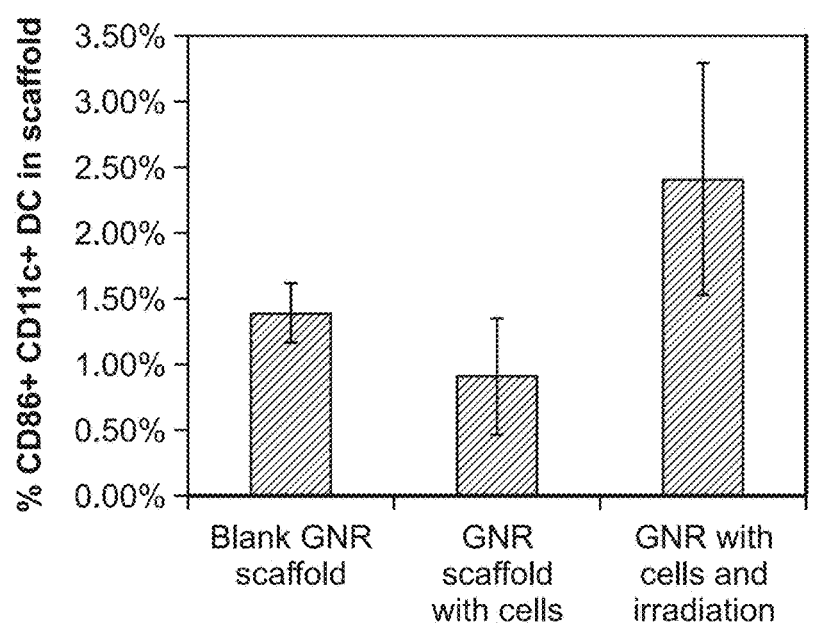

Example 11: In Vivo Irradiation of Implanted Device Leads to Increase in DC Activation and Number of Recruited DC's In vivo dendritic cell recruitment and activation using laser irradiation were evaluated. $10^6$ EG7.Ova lymphoma cells were loaded into GNR-PLG scaffolds with GM-CSF. The scaffolds were implanted subcutaneously in C57BL/6J mouse. On day 3 post implantation the scaffold site was irradiated with 808 nm NIR laser to 45° C. for 5 minutes. On day 7 post implantation, the scaffolds were retrieved, digested, and the cells were analyzed for the dendritic marker (CD11c), and the activation marker (CD86). FIGS. 16A-B show that laser irradiation significantly (n=3, p<0.05) increases the percentage of recruited dendritic cells (A) activates them in the scaffold (B).

Figure 17A:
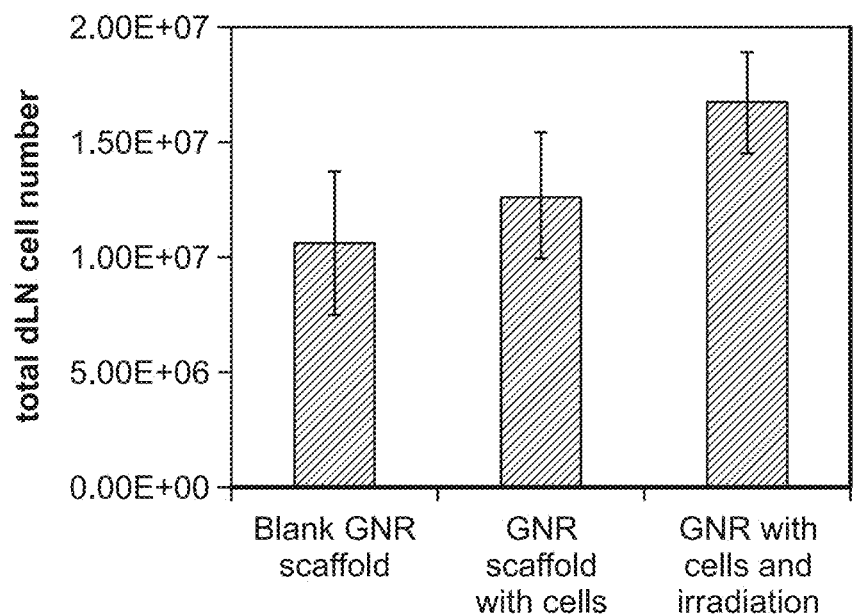
FIGS. 17A-B are bar graphs showing draining lymph node cell number and DC activation in draining lymph node tissue.
Figure 17B:
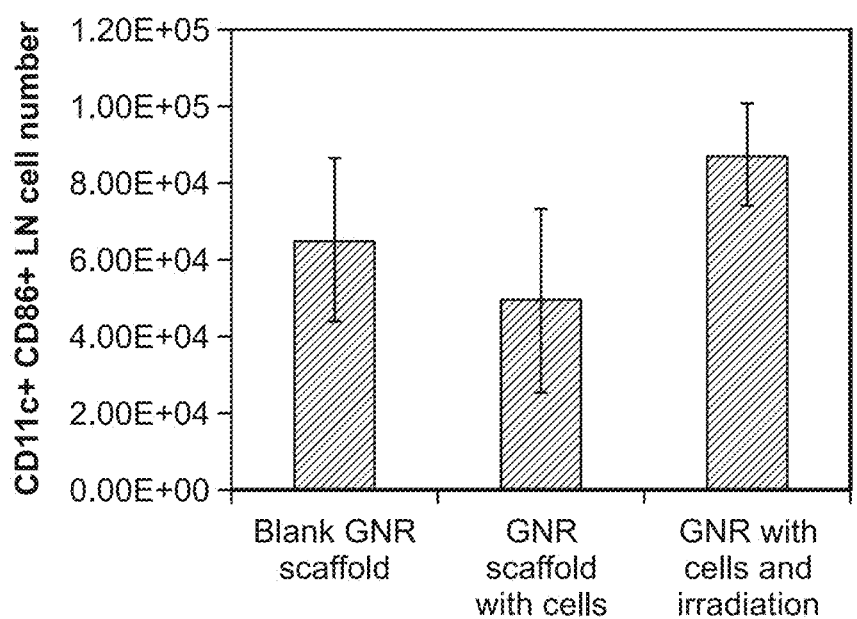
Figure 18A:
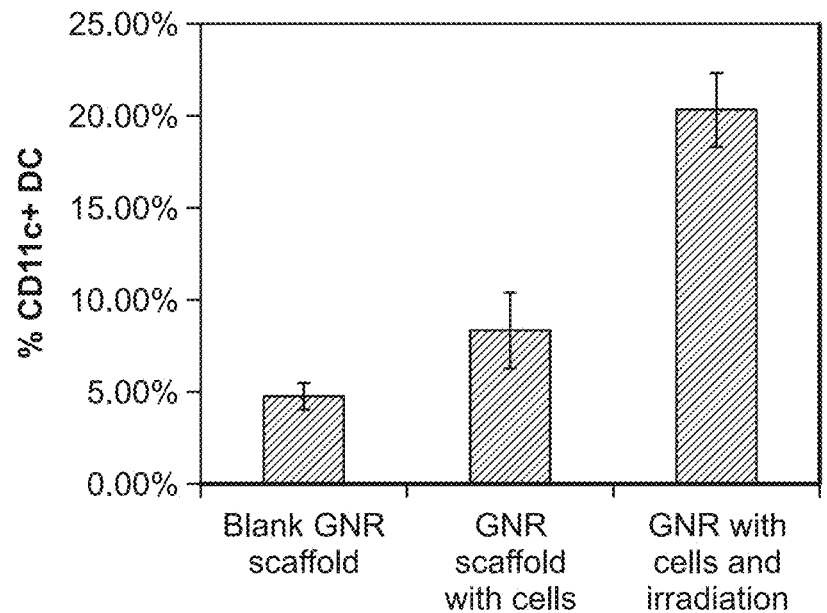
FIGS. 18A-D are bar graphs showing DC recruitment and activation in PLG vaccine using laser irradiation.
Figure 18B:
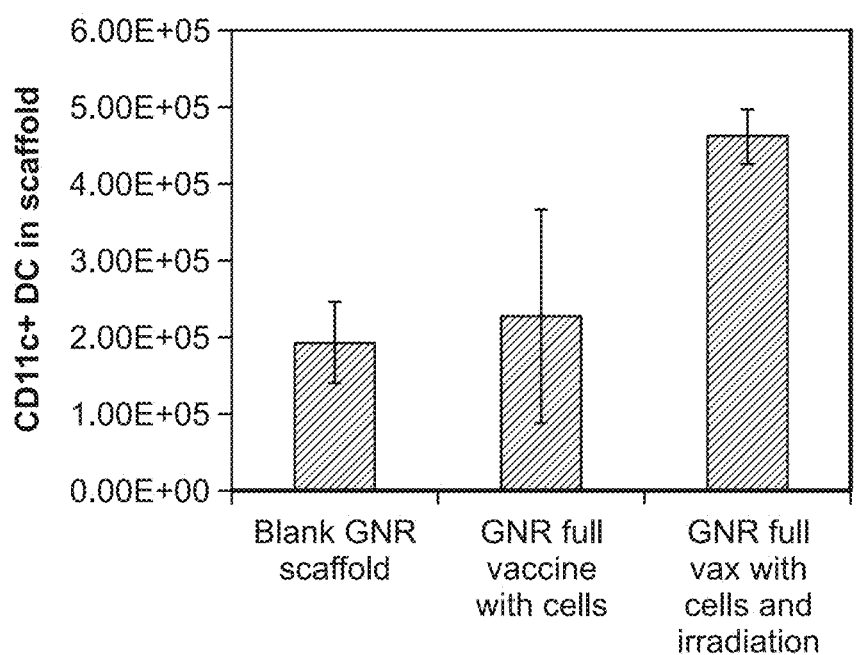
Figure 18C:
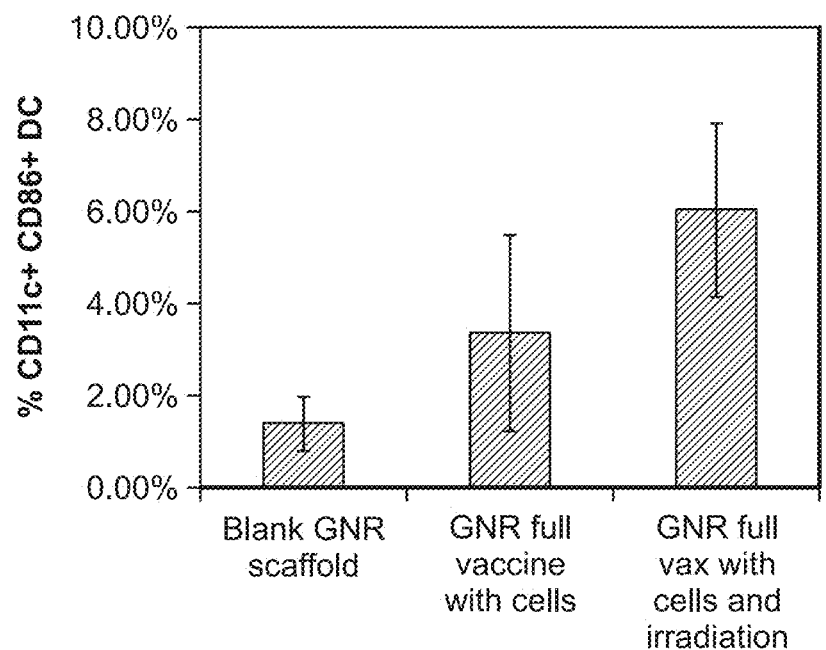
Figure 18D:
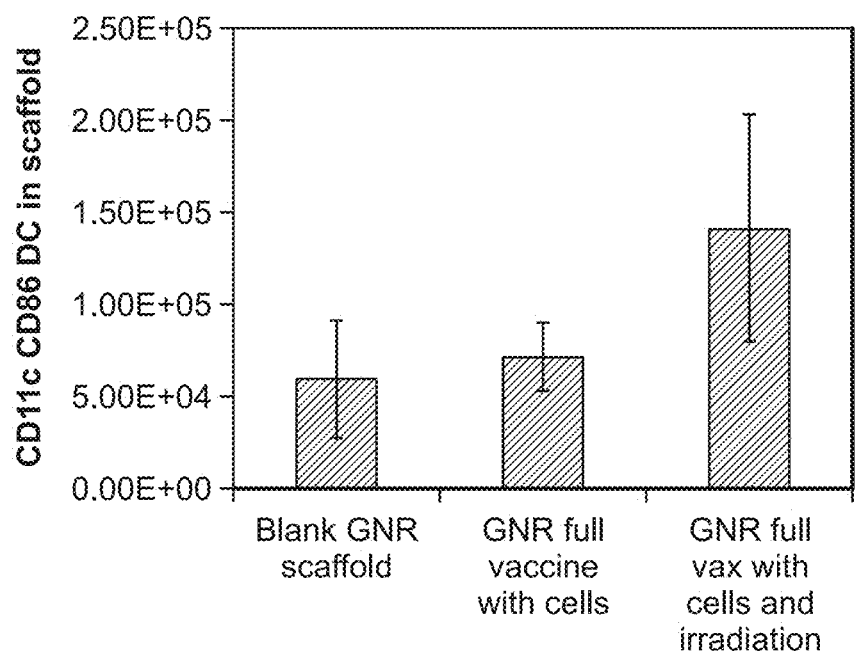

Example 12: In Vivo Irradiation of Implanted Device Leads to Increase in DC Activation and Number of Activated DCs in Draining Lymph Node In vivo dendritic cell activation in the draining lymph node using laser irradiation was evaluated. $10^6$ EG7.Ova lymphoma cells were loaded into GNR-PLG scaffolds with GM-CSF. The scaffolds were implanted subcutaneously in the back of a C57BL/6J mouse. On day 3 post implantation the scaffold site was irradiated with 808 nm NIR laser to 45° C. for 5 minutes. On day 7 post implantation, the draining lymph nodes (inguinal lymph nodes) were retrieved, digested, and the cells were analyzed for the dendritic marker (CD11c), and the activation marker (CD86). FIGS. 17A-B show that laser irradiation significantly (n=3, p<0.05) enlarges the draining lymph node (A), which is a response after inflammation, and increases the number of activated dendritic cells (B) in the lymph node. These data indicate that recruited DCs leave the scaffold device and migrate/relocated to draining lymph nodes (i.e., an anatomical site different from the location of the implanted device).

Example 13: Irradiation as an Additional Danger Signal for Immune Cell Activation In vivo dendritic cell recruitment and activation in the full PLG vaccine using laser irradiation were evaluated. $10^6$ EG7.Ova lymphoma cells were loaded into GNR-PLG scaffolds with GM-CSF and condensed CpG-ODN, which serves as the danger signal to activate DCs. The scaffolds were implanted subcutaneously in C57BL/6J mouse. On day 3 post implantation the scaffold site was irradiated to 45° C. for 5 minutes with 808 nm NIR laser. On day 7 post implantation, the scaffolds were retrieved, digested, and the cells were analyzed for the dendritic marker (CD11c), and the activation marker (CD86). FIGS. 18A-D show that laser irradiation further increases (n=3, p<0.05) the percentage (A) and total number (B) of recruited DCs, and activates them at the scaffold site (C-D). This data indicate indicates that laser irradiation serves as an additional danger signal for immune cell activation.

Example 14: Hyperthermic Treatment of Cancer Cells

Figure 19:
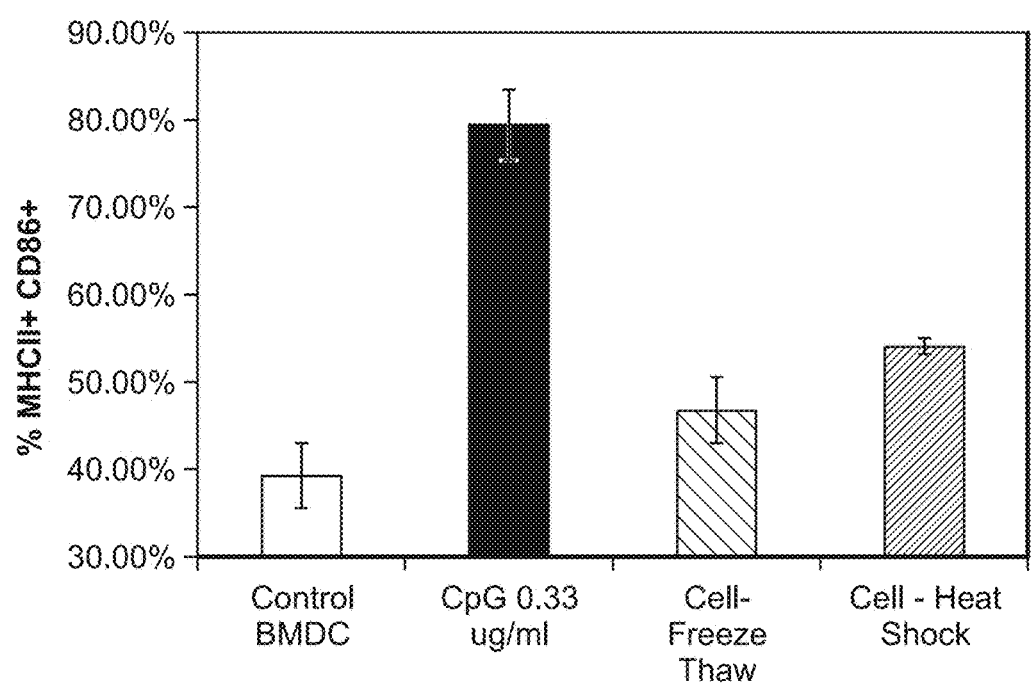
FIG. 19 is a bar graph showing DC activation with heat-shocked cancer cell lysate compared to freeze/thaw cancer cell lysate.
Figure 20A:
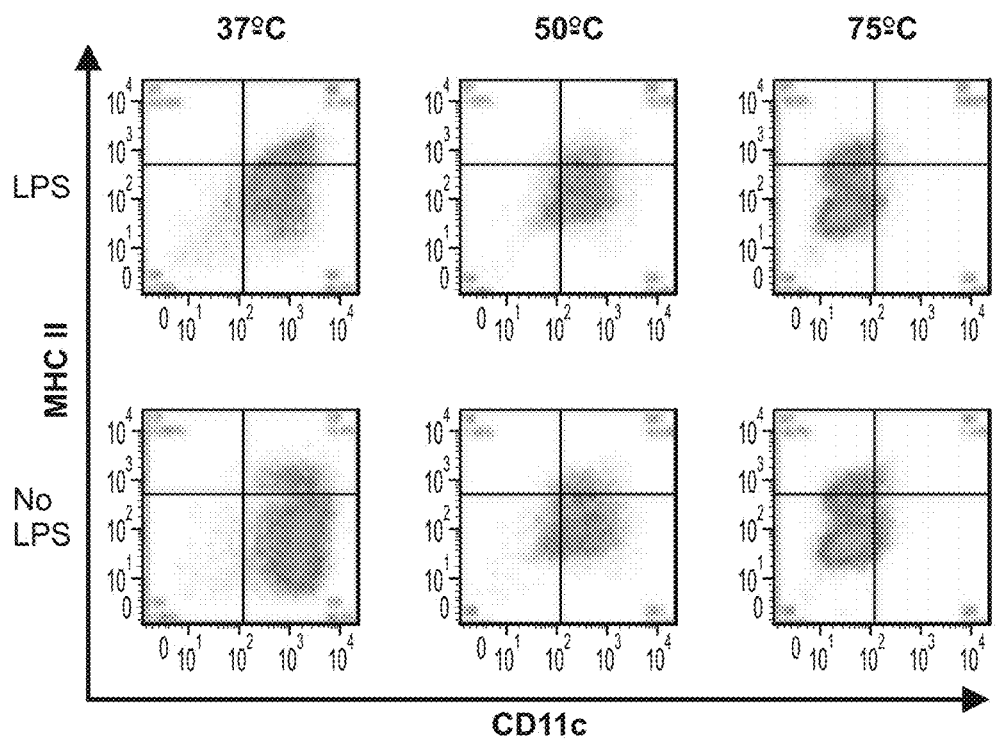
FIGS. 20A-B are scatter plots.
Figure 20B:
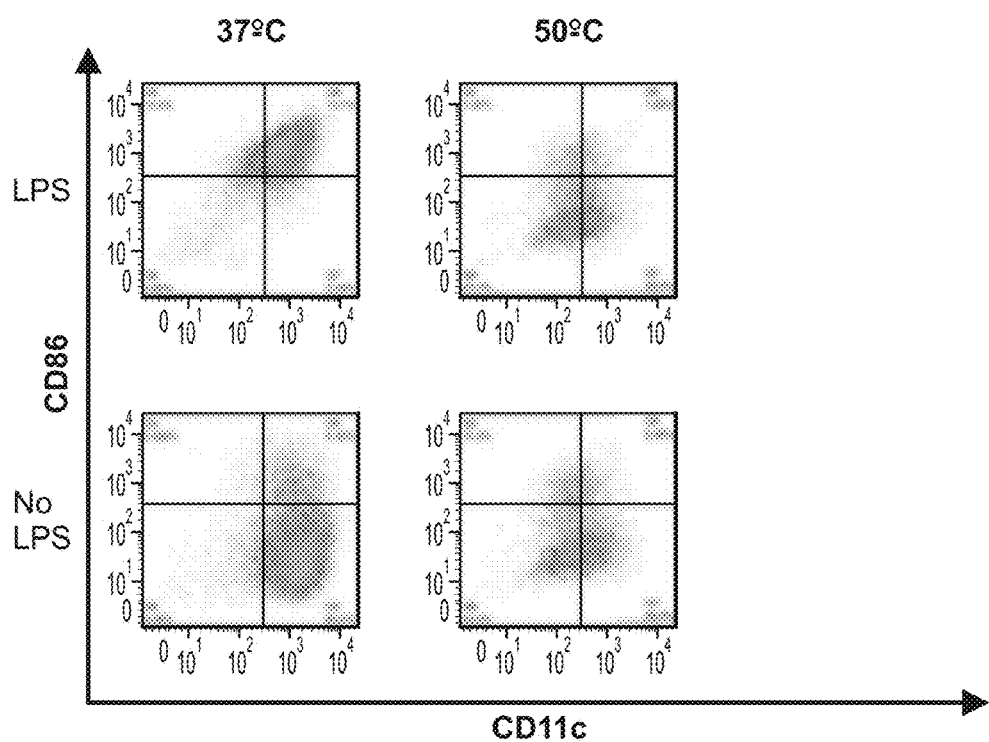
Figure 20C:
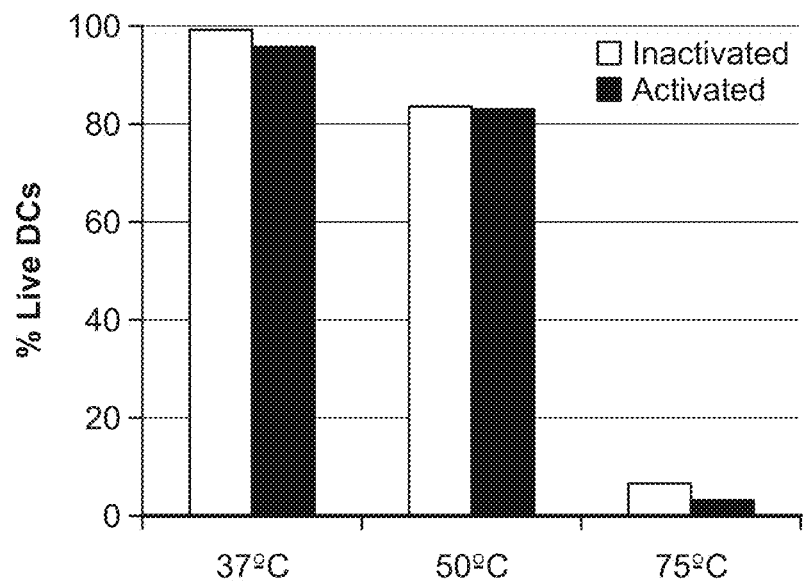
FIGS. 20C-D are bar graphs showing DC responsiveness to lipopolysaccharide (LPS).
Figure 20D:
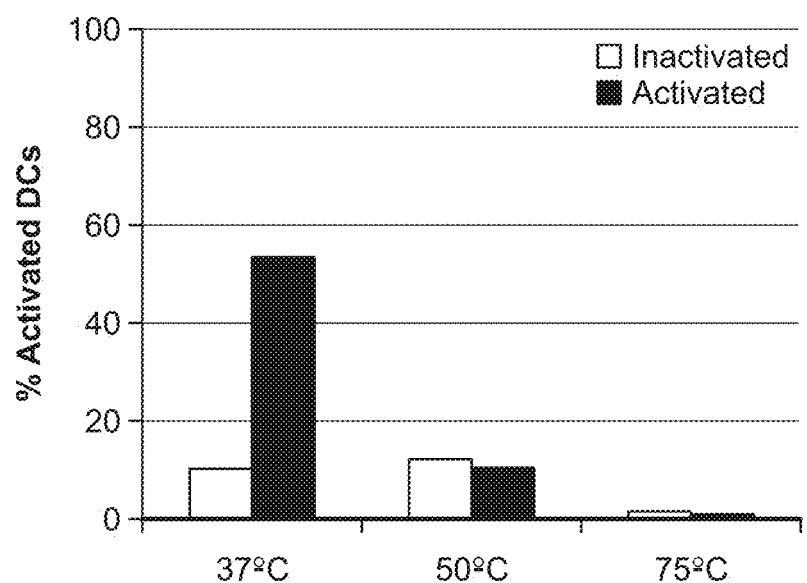

In vitro BMDC activation with heat shock B16 cell lysate was evaluated. $10 \times 10^6$ B16 melanoma cells were heat shocked at 45° C. for 5 minutes in pre-warmed water bath to prepare heat-shocked cell lysate. Conventional cell lysate was generated using 3 cycles of freeze-thaw procedure. The prepared lysate was incubated with $10^6$ BMDCs for 18 hours. BMDC activation markers, MHCII and CD86, were analyzed using flow cytometry. Cells were gated on CD11c+ DCs. FIG. 19 shows that the lysate generated from heat shocked cells serves as a danger signal to activate DCs, because it is capable of generating more (p<0.05) activated DCs than conventional cell lysates.

Example 15: Effect of Temperature on LPS Responsiveness

High temperature induces reduced responsiveness to LPS in BMDC in vitro. $10^6$/well BMDCs were heat shocked at 50° C. for 5 minutes. They were then incubated with or without LPS, an immune adjuvant capable of upregulating immune cell activation. Activation markers, CD86 and MHC-II, were analyzed in flow cytometry. FIGS. 20 A-D show that heat shock can abrogate the BMDCs' capability to respond to LPS stimulation. Thus, an alternative scaffold structure was developed to protect recruited DCs from irradiation.

Example 16: Device with Core-Shell Architecture

Figure 21A:
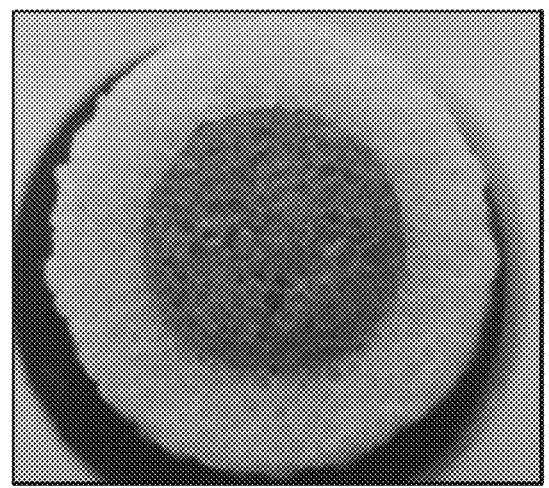
FIG. 21A is a photograph of an antigen-generating cancer vaccine device with a core-shell architecture.
Figure 21B:
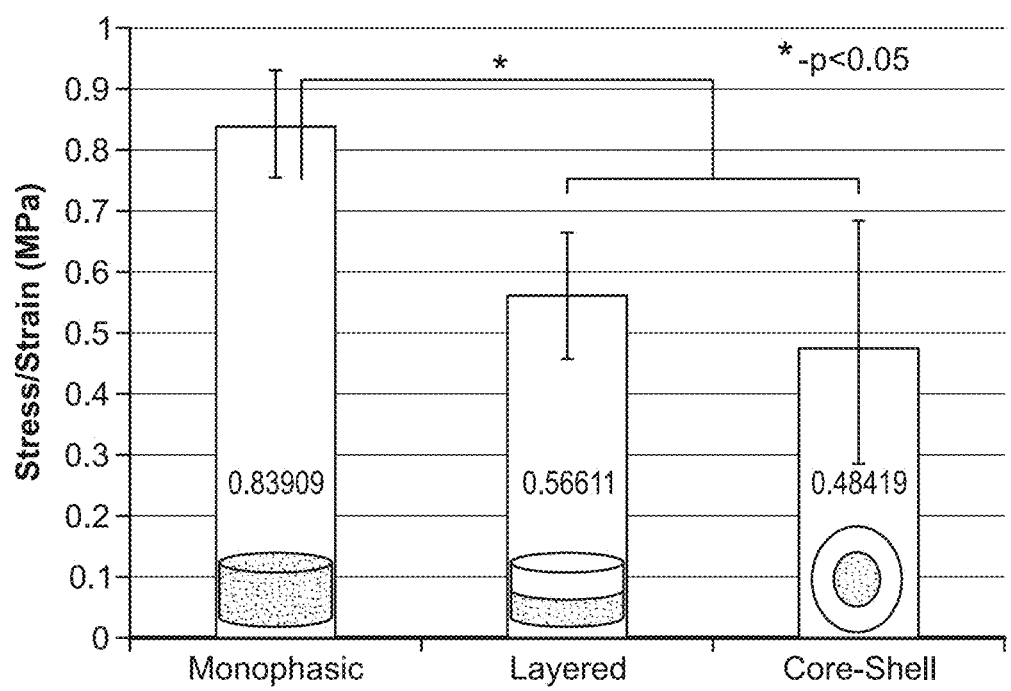
FIG. 21B is a bar graph showing the Young's modulus characteristics of an antigen-generating cancer vaccine with monophasic, layered, and core-shell architecture.
Figure 21C:
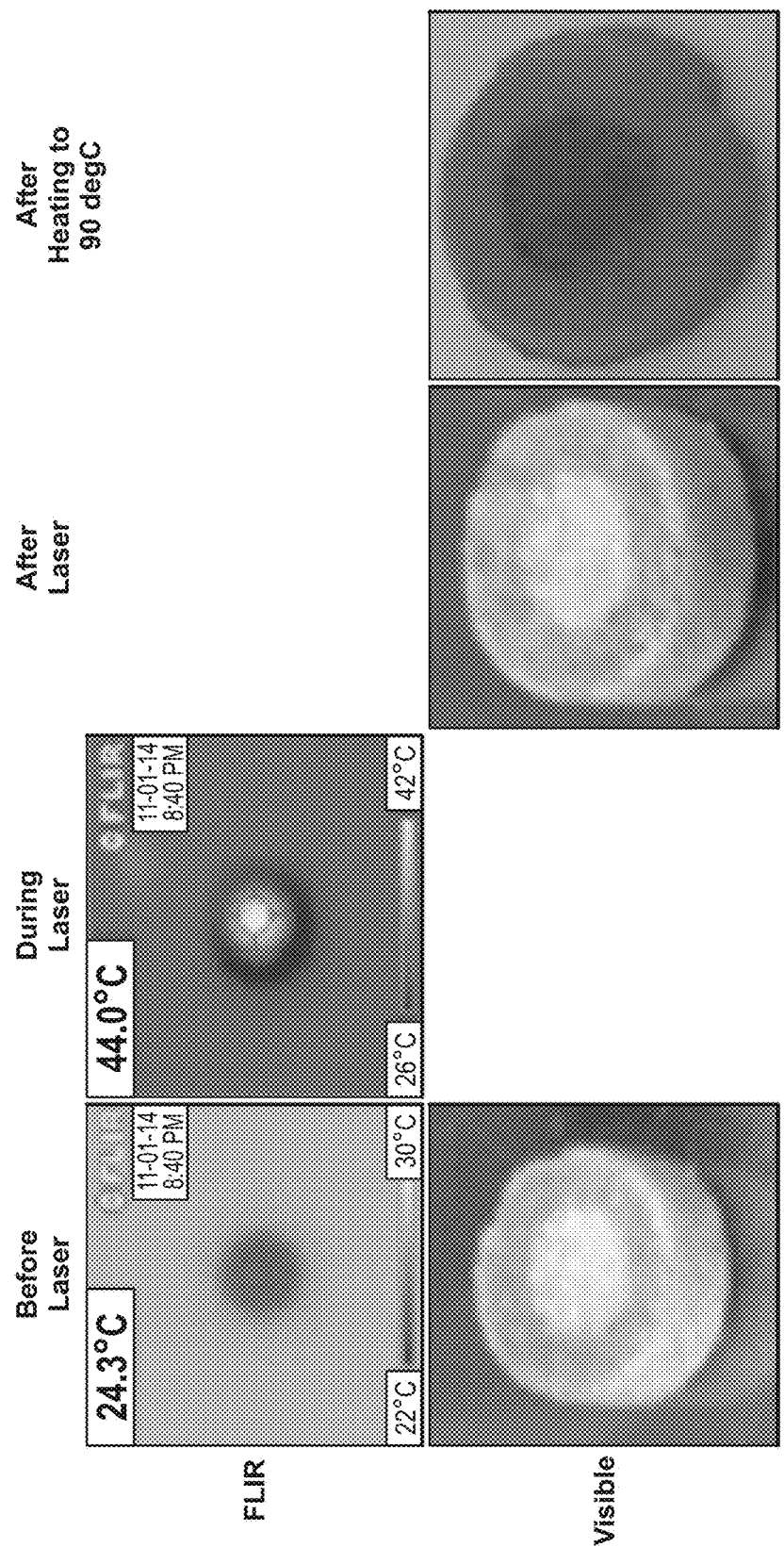
FIG. 21C is a series of photographs of an antigen-generating cancer vaccine scaffold device. The top panel shows the results of FLIR thermal imaging (thermography) of the device, and the bottom panel shows the results of visible imaging (photography).

An alternative structure of GNR scaffold, a core-shell type scaffold, was engineered to avoid the direct killing of recruited BMDCs but to allow for the heat shock of recruited cancer cells. The inner core scaffold is designed to load cancer recruiting chemokine and GNR (the color is dark due to loaded GNR); the outer shell scaffold is loaded with only GM-CSF to recruit DCs. Compressive testing demonstrates that this scaffold scheme has a lower Young's modulus than the conventional scaffold scheme (FIGS. 21A-C). In this design, only the cancer cells that are recruited to the inner core scaffold are subjected to heat shock from laser irradiation and the recruited DCs in outer shell scaffold avoid heat shock.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A biopsy-free method for producing a processed tumor antigen in situ comprising
   administering to a subject having a cancer comprising circulating tumor cells a porous 3-dimensional scaffold that does not comprise a tumor antigen before the scaffold is administered to the subject, said scaffold comprising
   (a) a chemoattractant for a cancer cell, wherein the chemoattractant for the cancer cell is released from the scaffold with a first release profile; and
   (b) an immune cell recruitment composition, wherein the immune cell recruitment composition is released from the scaffold with a second release profile, such that cancer cells are recruited to the scaffold prior to recruitment of immune cells;
   maintaining the scaffold in situ for a period of time sufficient to accumulate circulating cancer cells, to yield a cancer cell-containing scaffold; and
   contacting said cancer cell-containing scaffold with a cytotoxic or cytolytic element to produce a processed tumor antigen, wherein the scaffold recruits an immune cell to the site of the processed tumor antigen after the processed tumor antigen is produced.

2. The method of claim 1, wherein said cytotoxic element comprises application of external heat, ultrasound, laser radiation, or gamma radiation to said cell-containing scaffold.

3. The method of claim 1, wherein said scaffold further comprises a hyperthermia-inducing composition.

4. A polymer vaccine scaffold device that first recruits a cancer cell that is destroyed to generate a lysate, and subsequently recruits a dendritic cell, wherein the device comprises
   (a) a cytotoxicity-inducing composition,
   (b) a chemoattractant for a cancer cell, wherein the chemoattractant for the cancer cell is released from the scaffold with a first release profile; and
   (c) an immune cell recruitment composition, wherein the immune cell recruitment composition is released from the scaffold with a second release profile, such that cancer cells are recruited to the scaffold prior to recruitment of immune cells following administration of the device to a subject;
   wherein said device does not comprise a tumor antigen before said device is administered to the subject.

5. A biopsy-free method for producing a processed tumor antigen in situ comprising administering to a subject diagnosed with a cancer the device of claim 4, thereby producing a processed tumor antigen in situ in the subject.

6. A method of treating cancer in a subject in need thereof, comprising administering the device of claim 4 to the subject, thereby treating cancer in the subject.

7. A method of activating an immune cell in a subject in need thereof, comprising administering the device of claim 4 to the subject and, after a period of time sufficient for the device to accumulate circulating cancer cells, irradiating the site of administration with a laser.

8. The method of claim 7, wherein said immune cell comprises a dendritic cell.

9. The method of claim 7, wherein the device is administered by implantation into said subject.

10. The method of claim 9, wherein said implantation comprises subcutaneous implantation.

11. The method of claim 1, wherein the immune cell comprises a dendritic cell.

12. The method of claim 1, wherein the chemoattractant for a cancer cell is a chemokine.

13. The method of claim 12, wherein the chemoattractant for a cancer cell is selected from the group consisting of CCL-21, CCL-19, SDF-1, VEGF, and IL-4.

14. The method of claim 12, wherein the chemoattractant for a cancer cell is CCL-21.

15. The method of claim 1, wherein the immune cell recruitment composition comprises GM-CSF.

16. The method of claim 1, wherein the scaffold further comprises CpG oligodeoxynucleotides (CpG-ODN).

17. The method of claim 3, wherein the hyperthermia-inducing composition comprises a magnetic nanoparticle or a near infrared (NIR) absorbing nanoparticle.

18. The method of claim 17, wherein the hyperthermia-inducing composition comprises a magnetic nanoparticle, and wherein said cytotoxic or cytolytic element comprises an alternative magnetic field.

19. The method of claim 17, wherein the hyperthermia-inducing composition comprises a NIR absorbing nanoparticle, and wherein said cytotoxic or cytolytic element comprises NIR radiation.

20. The method of claim 17, wherein the hyperthermia-inducing composition comprises a NIR absorbing nanoparticle selected from the group consisting of a gold nanorod, a gold nanoshell, a gold nanocage, a noble metal nanoparticle, a carbon nanotube, a carbon nanoparticle, and a graphite nanoparticle.

21. The method of claim 20, wherein the hyperthermia-inducing composition comprises a gold nanorod or a gold nanoshell.

22. The method of claim 1, wherein the scaffold comprises a first polymer comprising the chemoattractant, and a second polymer comprising the immune cell recruitment composition.

23. The method of claim 22, wherein the first polymer has a different degradation profile than the second polymer.

24. The method of claim 1, wherein the cancer comprises metastatic cancer cells.

25. The method of claim 1, wherein the cancer is a blood-borne cancer.

26. The method of claim 25, wherein the cancer is leukemia.

27. The method of claim 1, wherein the subject is a human subject.

28. The device of claim 4, wherein the chemoattractant for a cancer cell is a chemokine.

29. The device of claim 4, wherein the chemoattractant for a cancer cell is selected from the group consisting of CCL-21, CCL-19, SDF-1, VEGF, and IL-4.

30. The device of claim 4, wherein the chemoattractant for a cancer cell is CCL-21.

31. The device of claim 4, wherein the immune cell recruitment composition comprises GM-CSF.

32. The device of claim 4, wherein the second polymer composition further comprises CpG oligodeoxynucleotides (CpG-ODN).

33. The device of claim 4, wherein the cytotoxicity-inducing composition comprises a hyperthermia-inducing particle.

34. The device of claim 33, wherein the wherein the hyperthermia-inducing particle comprises a magnetic nanoparticle or a near infrared (NIR) absorbing nanoparticle.

35. The device of claim 33, wherein the hyperthermia-inducing particle comprises a NIR absorbing nanoparticle selected from the group consisting of a gold nanorod, a gold nanoshell, a gold nanocage, a noble metal nanoparticle, a carbon nanotube, a carbon nanoparticle, and a graphite nanoparticle.

36. The device of claim 33, wherein the hyperthermia-inducing particle comprises a gold nanoparticle or a gold nanorod.

37. The device of claim 4, wherein the device comprises a first polymer comprising the chemoattractant, and a second polymer comprising the immune cell recruitment composition.

38. The device of claim 37, wherein the first polymer has a different degradation profile than the second polymer.

* * * * *

UNITED STATES PATENT AND TRADEMARK OFFICE
CERTIFICATE OF CORRECTION

PATENT NO. : 10,406,216 B2
APPLICATION NO. : 15/345131
DATED : September 10, 2019
INVENTOR(S) : Jaeyun Kim et al.

It is certified that error appears in the above-identified patent and that said Letters Patent is hereby corrected as shown below:

In the Claims

In Claim 32 (Column 16, Line numbers 17-19), delete "The device of claim 4, wherein the second polymer composition further comprises CpG oligodeoxynucleotides (CpG-ODN)" and replace it with "The device of claim 4, wherein the cytotoxicity-inducing composition comprises a hyperthermia-inducing particle".

In Claim 33 (Column 16, Line numbers 20-22), delete "The device of claim 4, wherein the cytotoxicity-inducing composition comprises a hyperthermia-inducing particle" and replace it with "The device of claim 32, wherein the hyperthermia-inducing particle comprises a magnetic nanoparticle or a near infrared (NIR) absorbing nanoparticle".

In Claim 34 (Column 16, Line numbers 23-25), delete "The device of claim 33, wherein the wherein the hyperthermia-inducing particle comprises a magnetic nanoparticle or a near infrared (NIR) absorbing nanoparticle" and replace it with "The device of claim 32, wherein the hyperthermia-inducing particle comprises a NIR absorbing nanoparticle selected from the group consisting of a gold nanorod, a gold nanoshell, a gold nanocage, a noble metal nanoparticle, a carbon nanotube, a carbon nanoparticle, and a graphite nanoparticle".

In Claim 35 (Column 16, Line numbers 26-31), delete "The device of claim 33, wherein the hyperthermia-inducing particle comprises a NIR absorbing nanoparticle selected from the group consisting of a gold nanorod, a gold nanoshell, a gold nanocage, a noble metal nanoparticle, a carbon nanotube, a carbon nanoparticle, and a graphite nanoparticle" and replace it with "The device of claim 32, wherein the hyperthermia-inducing particle comprises a gold nanoparticle or a gold nanorod".

In Claim 36 (Column 16, Line numbers 32-34), delete "The device of claim 33, wherein the hyperthermia-inducing particle comprises a gold nanoparticle or a gold nanorod" and replace it with "The device of claim 4, wherein the device comprises a first polymer comprising the chemoattractant, and a second polymer comprising the immune cell recruitment composition".

Signed and Sealed this
Eighteenth Day of February, 2020

Andrei Iancu
*Director of the United States Patent and Trademark Office*

CERTIFICATE OF CORRECTION (continued)
U.S. Pat. No. 10,406,216 B2

In Claim 37 (Column 16, Line numbers 35-38), delete "The device of claim 4, wherein the device comprises a first polymer comprising the chemoattractant, and a second polymer comprising the immune cell recruitment composition" and replace it with "The device of claim 36, wherein the first polymer has a different degradation profile than the second polymer".

In Claim 38 (Column 16, Line numbers 39-40), delete "The device of claim 37, wherein the first polymer has a different degradation profile than the second polymer." and replace it with "The device of claim 36, wherein the second polymer further comprises CpG oligodeoxynucleotides (CpG-ODN)".